(12) United States Patent
Kim et al.

(10) Patent No.: US 9,815,900 B2
(45) Date of Patent: Nov. 14, 2017

(54) MONOCLONAL ANTIBODY WHICH IS SPECIFICALLY BOUND TO TM4SF5 PROTEIN AND USE THEREOF

(71) Applicants: Korea Research Institute of Bioscience and Biotechnology, Daejeon (KR); SNU R&DB Foundation, Seoul (KR)

(72) Inventors: Se Mi Kim, Daejeon (KR); Sang Jick Kim, Daejeon (KR); Hye Jin Min, Daejeon (KR); Jin Myeong Song, Daejeon (KR); Jung Weon Lee, Seoul (KR); Hye Jin Kim, Ulsan (KR); HyeMi Ahn, Daejeon (KR); InPyo Choi, Daejeon (KR); JiHye Ryu, Gyeongsangnam-do (KR)

(73) Assignees: Korea Research Institute of Bioscience and Biotechnology, Daejeon (KR); SNU R&DB Foundation, Seoul (KR)

( * ) Notice: Subject to any disclaimer, the term of this patent is extended or adjusted under 35 U.S.C. 154(b) by 121 days.

(21) Appl. No.: 14/613,014

(22) Filed: Feb. 3, 2015

(65) Prior Publication Data
US 2015/0239975 A1 Aug. 27, 2015

Related U.S. Application Data

(63) Continuation-in-part of application No. PCT/KR2013/007033, filed on Aug. 5, 2013.

(30) Foreign Application Priority Data

Aug. 3, 2012 (KR) .......... 10-2012-0085436
Aug. 3, 2012 (KR) .......... 10-2012-0085437

(51) Int. Cl.
| | | |
|---|---|---|
| *A61K 38/00* | (2006.01) | |
| *G01N 33/574* | (2006.01) | |
| *C07K 16/28* | (2006.01) | |
| *C07K 16/30* | (2006.01) | |
| *G01N 33/577* | (2006.01) | |

(52) U.S. Cl.
CPC .......... *C07K 16/2863* (2013.01); *C07K 16/28* (2013.01); *C07K 16/30* (2013.01); *C07K 16/303* (2013.01); *G01N 33/577* (2013.01); *G01N 33/57419* (2013.01); *G01N 33/57438* (2013.01); *G01N 33/57446* (2013.01); *C07K 2317/56* (2013.01); *C07K 2317/565* (2013.01); *C07K 2317/76* (2013.01); *G01N 2333/4703* (2013.01)

(58) Field of Classification Search
None
See application file for complete search history.

(56) References Cited

U.S. PATENT DOCUMENTS

2013/0178533 A1 7/2013 Lee et al.

FOREIGN PATENT DOCUMENTS

| KR | 10-0934706 B1 | 12/2009 |
|---|---|---|
| KR | 10-2010-0019670 A | 2/2010 |
| KR | 10-2012-0023524 A | 3/2012 |

OTHER PUBLICATIONS

Ahn et al. Anti-cancer Activity of Novel TM4SF5-Targeting Antibodies through TM4SF5 Neutralization and Immune Cell-Mediated Cytotoxicity. Theranostics. 2017; 7(3): 594-613.*
Kwon et al. Monoclonal antibody targeting of the cell surface molecule TM4SF5 inhibits the growth of hepatocellular carcinoma.. Cancer Res. Jul. 15, 2014;74(14):3844-56.*
Kim et al. Therapeutic effect of a TM4SF5-specific monoclonal antibody against colon cancer in a mouse model. Oncotarget. Sep. 2014; 5(18): 8402-8415.*
Cell atlas—TM4SF5—The Human Protein Atlas. http://www.proteinatlas.org/ENSG00000142484-TM4SF5/cell. pp. 1-3, Feb. 3, 2017.*
Extended European Search Report issued in related European Patent Application No. 13824875.2 dated Feb. 18, 2016.
Lee et al., "Modulation of signaling between TM4SF5 and integrins in tumor microenvironment," Frontiers in Bioscience, 16: 1752-1758 (2011).
Lee et al., "Transmembrane 4 L Six Family Member 5 (TM4SF5) Enhances Migration and Invasion of Hepatocytes for Effective Metastasis," Journal of Cellular Biochemistry, 111: 59-66 (2010).
Tiller et al., "Efficient generation of monoclonal antibodies from single human B cells by single cell RT-PCR and expression vector cloning," Journal of Immunological Methods, 329: 112-124 (2008).
Kwon et al., "Prophylactic effect of a peptide vaccine targeting TM4SF5 against colon cancer in a mouse model," Biochemical and Biophysical Research Communications, 435: 134-139 (2013).
Lee et al., "Tetraspanin TM4SF5 mediates loss of contact inhibition through epithelial-mesenchymal transition in human hepatocarcinoma," Journal of Clinical Investigation, 118: 1354-1366 (2008).

(Continued)

*Primary Examiner* — Maher Haddad
(74) *Attorney, Agent, or Firm* — Morgan, Lewis & Bockius LLP

(57) ABSTRACT

The present invention relates to a novel monoclonal antibody which is specifically bound to a transmembrane 4 L six family member 5 (TM4SF5) protein. More particularly, the present invention relates to a monoclonal antibody which is specifically bound to a human TM4SF5 protein, to polynucleotides coding for the monoclonal antibody, to an expression vector comprising the nucleotides, to a transformant with the vector introduced thereto, to a method for preparing the monoclonal antibody, to a composition comprising the monoclonal antibody, to a method for treating liver fibrosis using the monoclonal antibody, to a method for treating cancer using the monoclonal antibody, to a method for inhibiting metastasis of cancer, to a method for diagnosing cancer using the monoclonal antibody and to a cancer diagnosis kit comprising the monoclonal antibody.

16 Claims, 47 Drawing Sheets

(56) References Cited

OTHER PUBLICATIONS

Kang et al., "Cross-talk between TGFβ1 and EGFR signalling pathways induces TM4SF5 expression and epithelial-mesenchymal transition," Biochemical Journal, 443: 691-700 (2012).
Kim et al., "TM4SF5 accelerates G1/S phase progression via cytosolic p27Kip1 expression and RhoA activity," Biochemica et Biophysical Acta, 1803: 975-982 (2010).
International Search Report issued in corresponding International Patent Application No. PCT/KR2013/007033 dated Nov. 19, 2013.
Office Action issued in Korean Patent Application No. 201380052088.5 dated Mar. 1, 2017.

\* cited by examiner

Fusion protein construct

TM4SF5 EC2: TM4SF5 amino acid residues 113 to 157
TCS: Thrombin cleavage site

FIG. 3

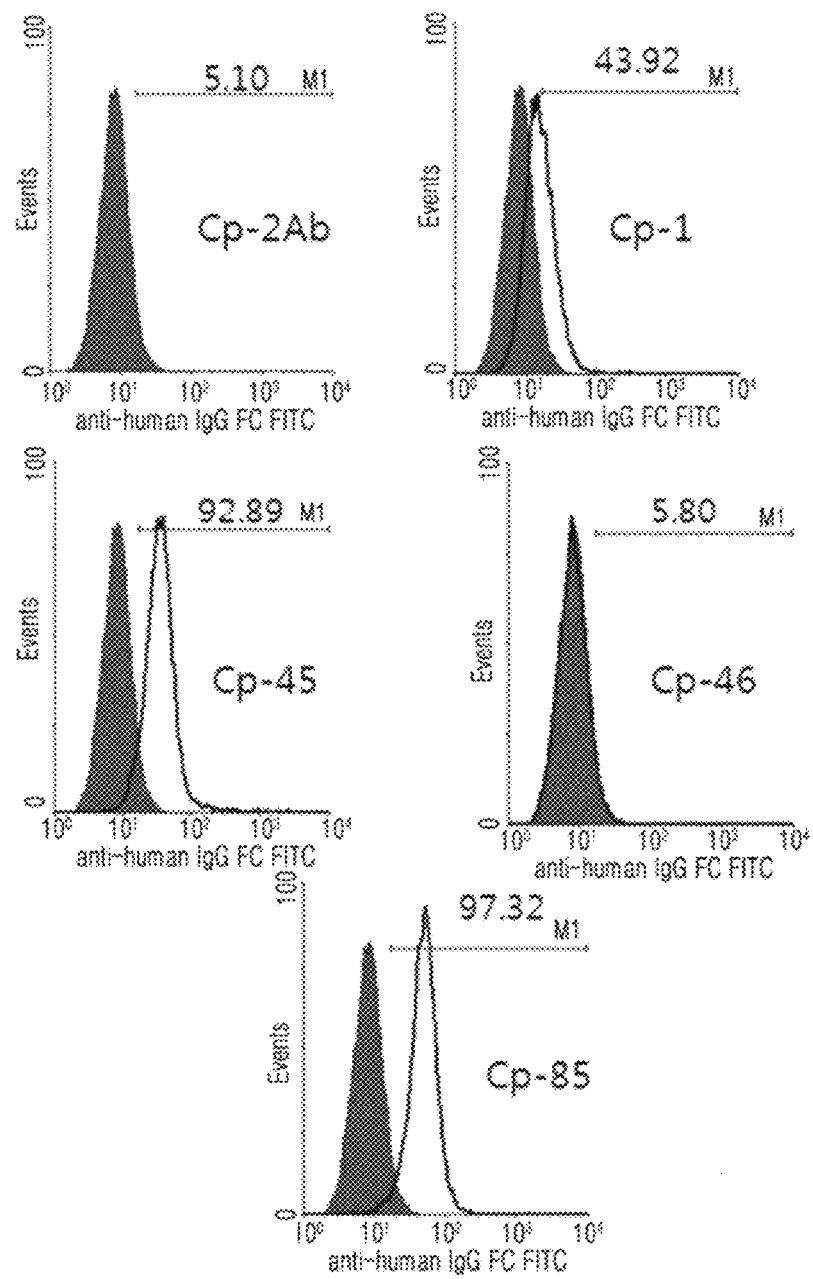

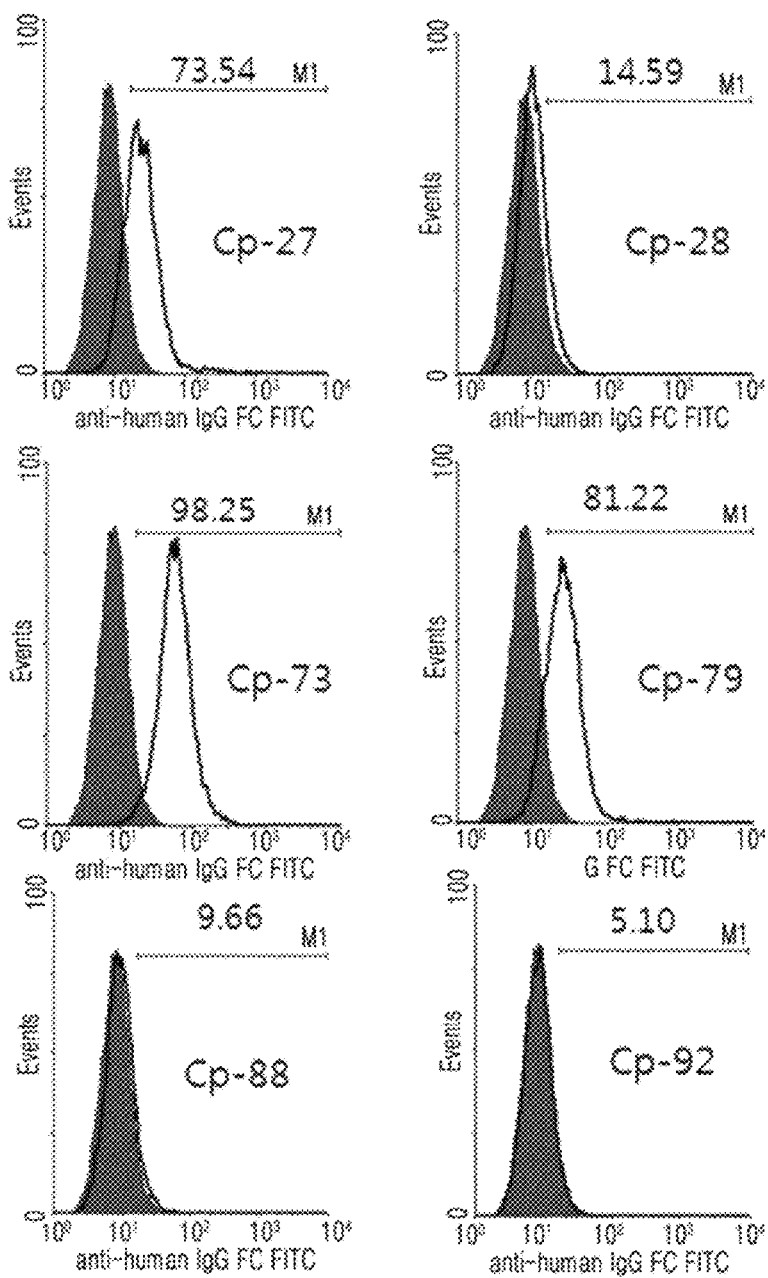

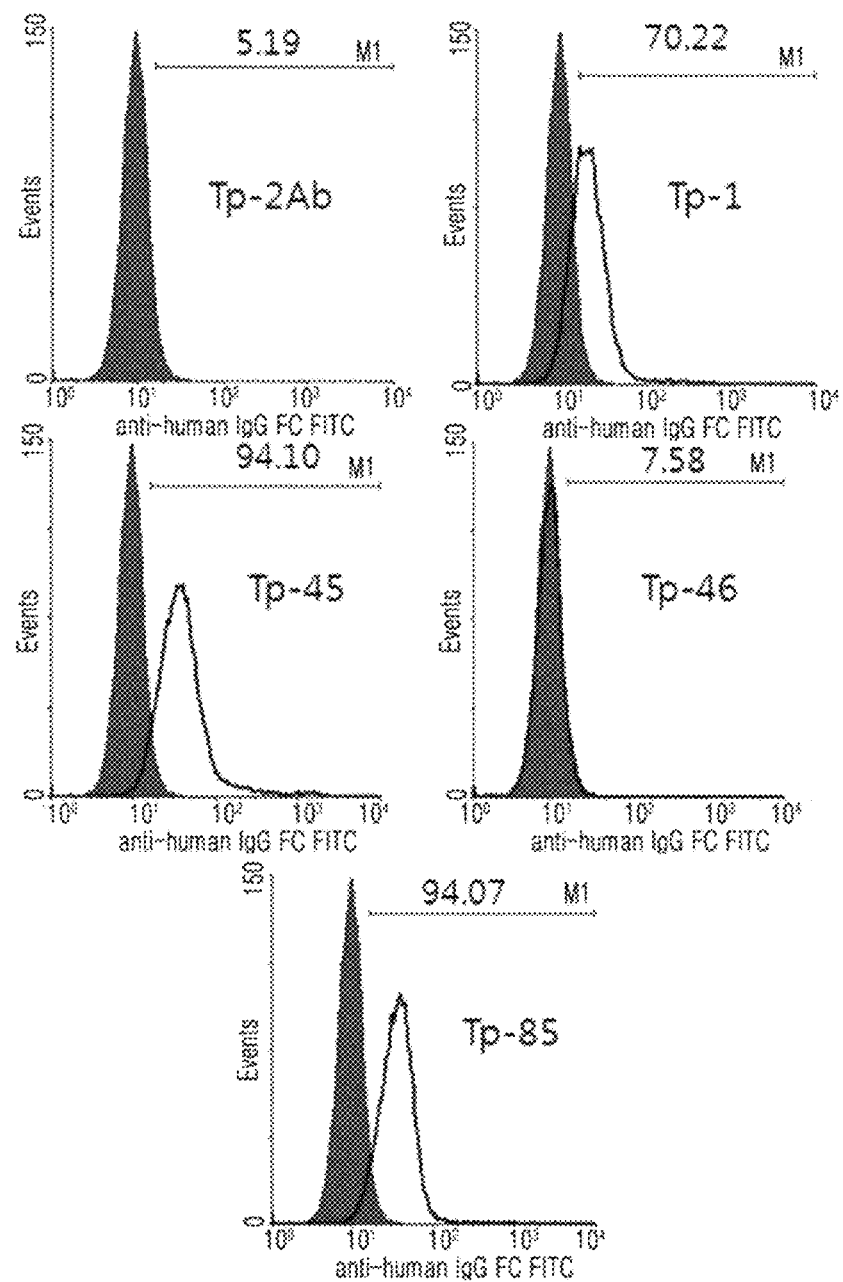

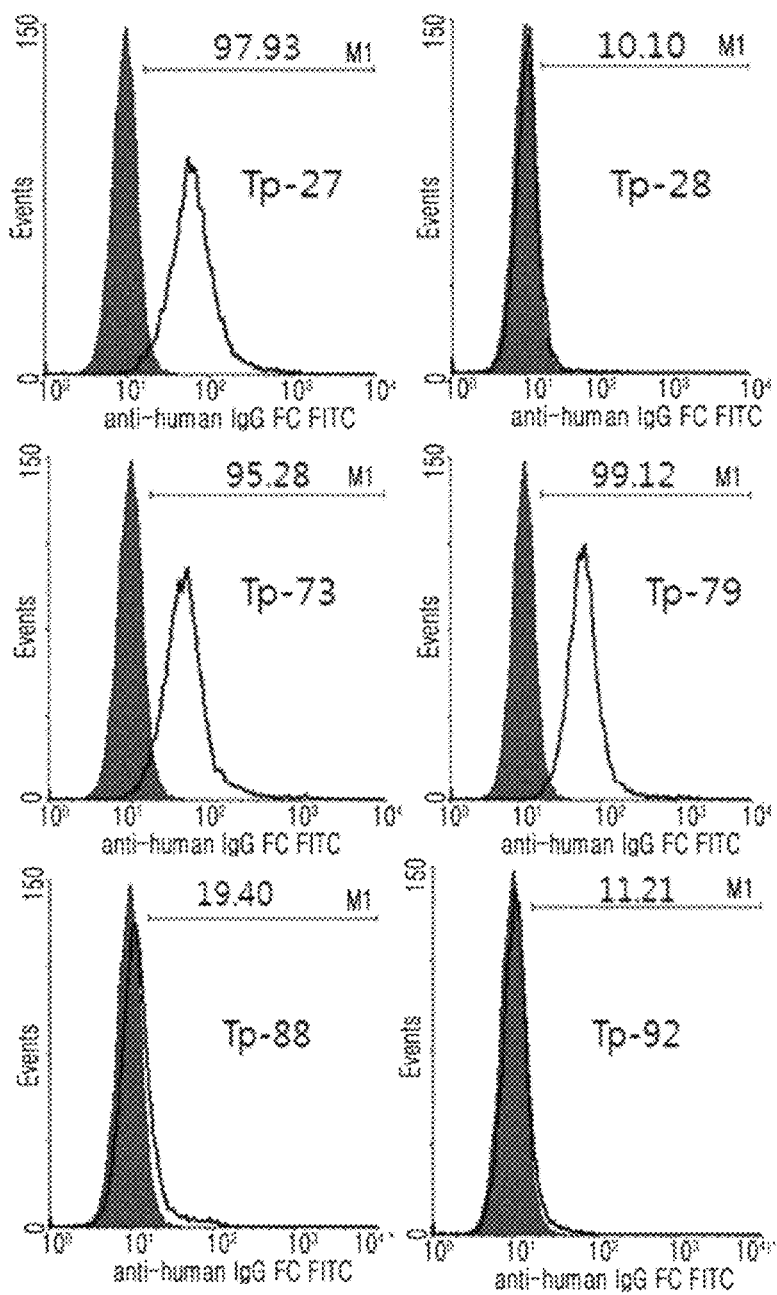

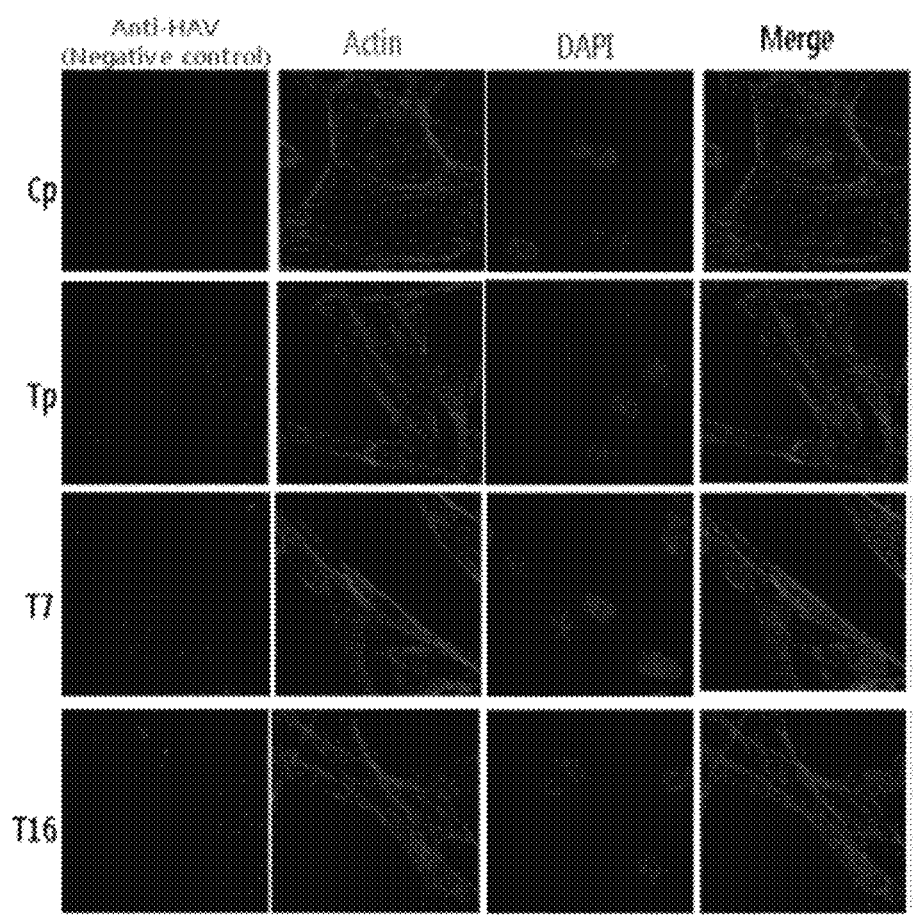

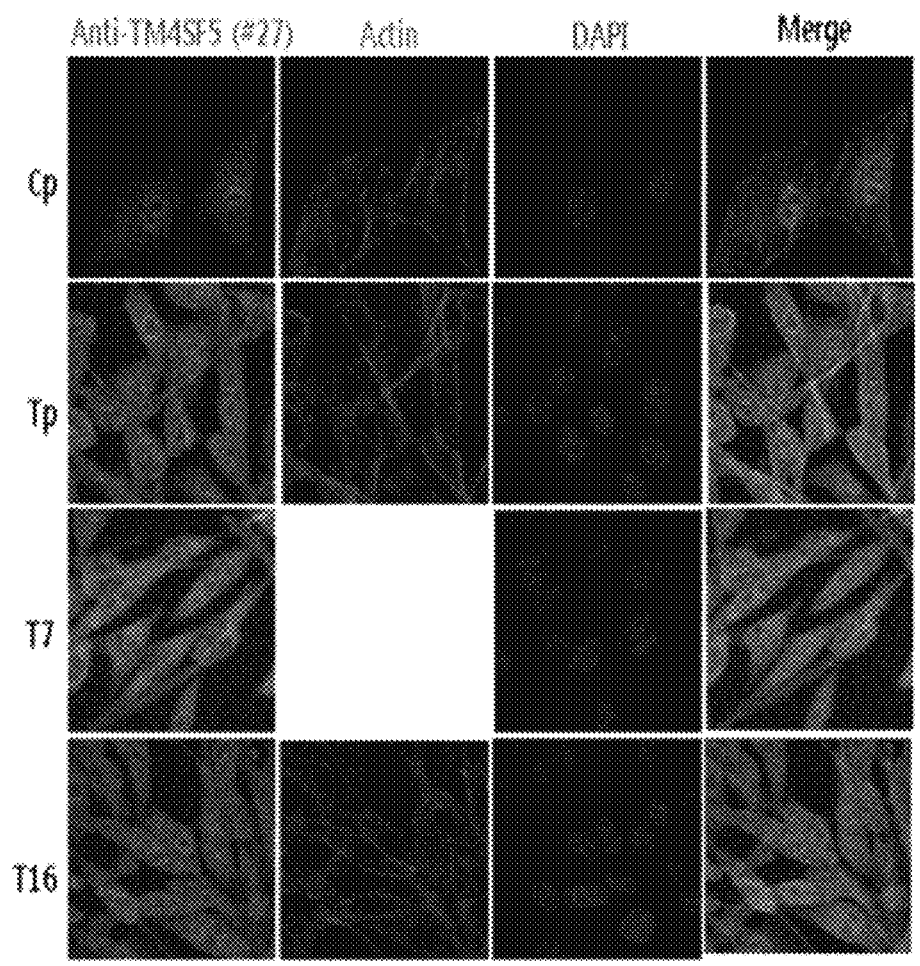

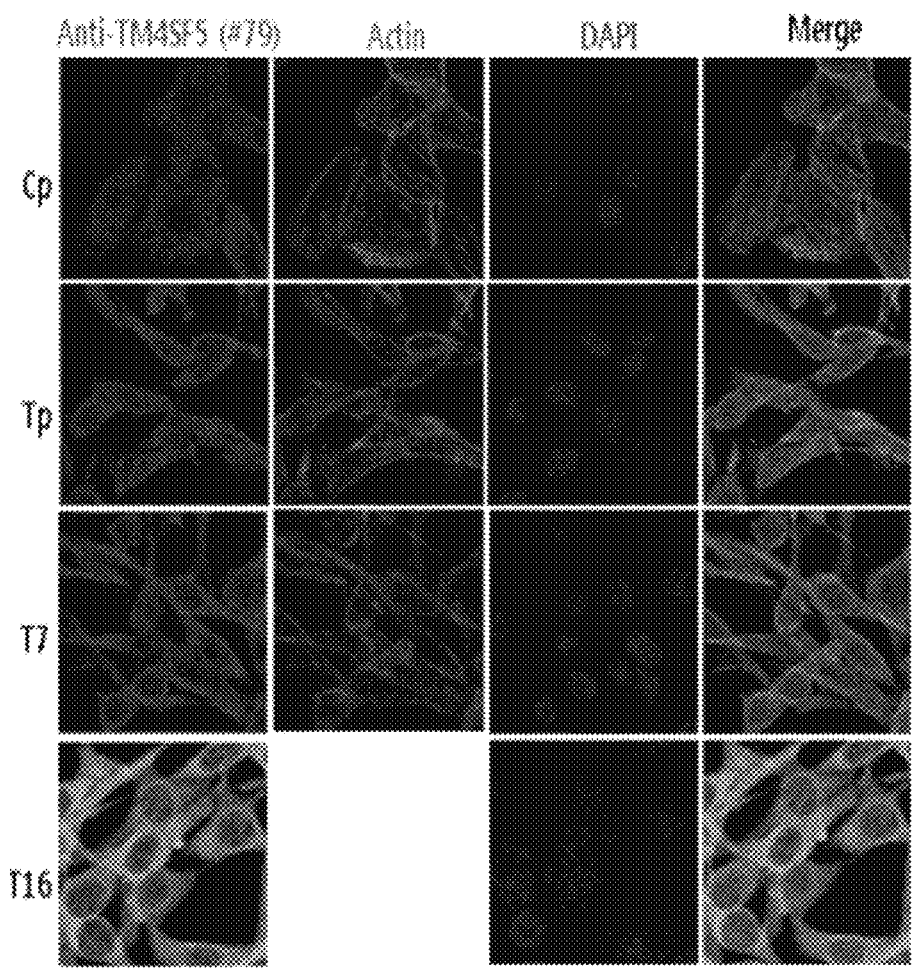

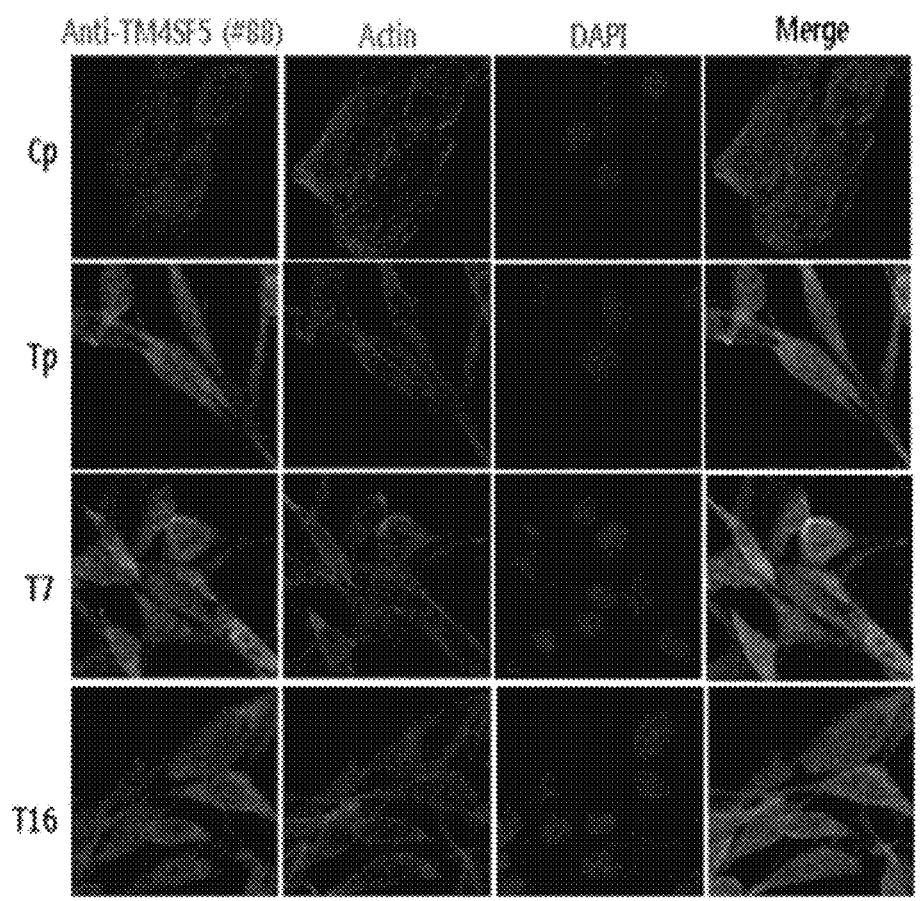

FIG. 10B
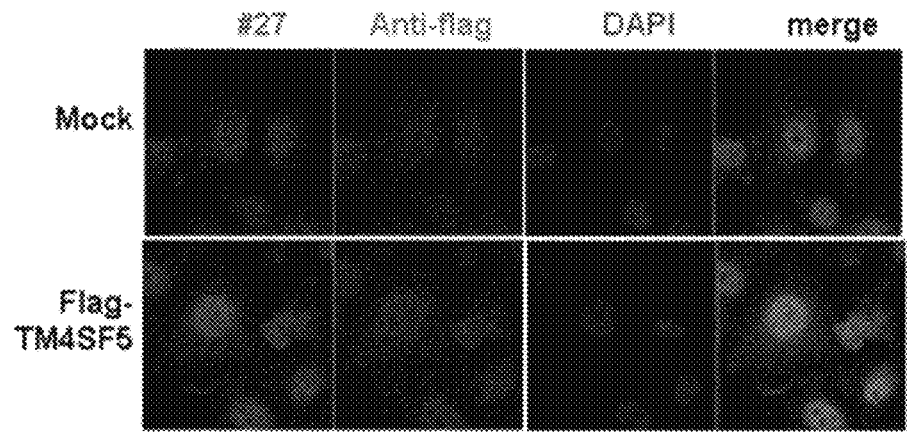
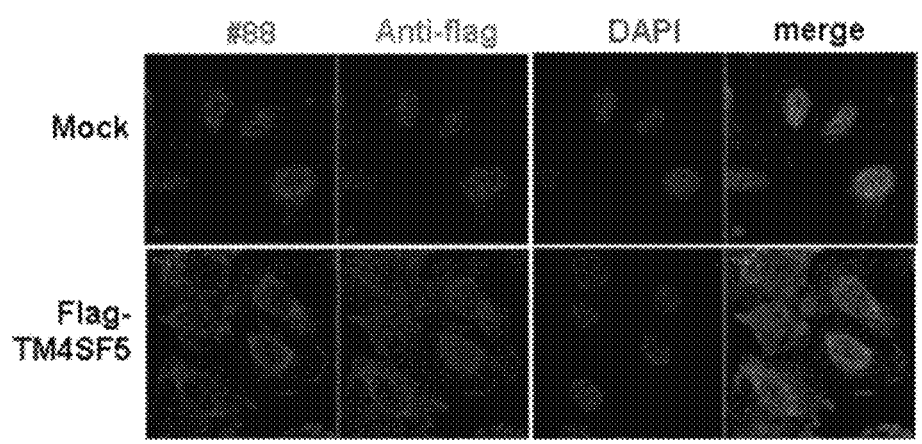
FIG. 10C
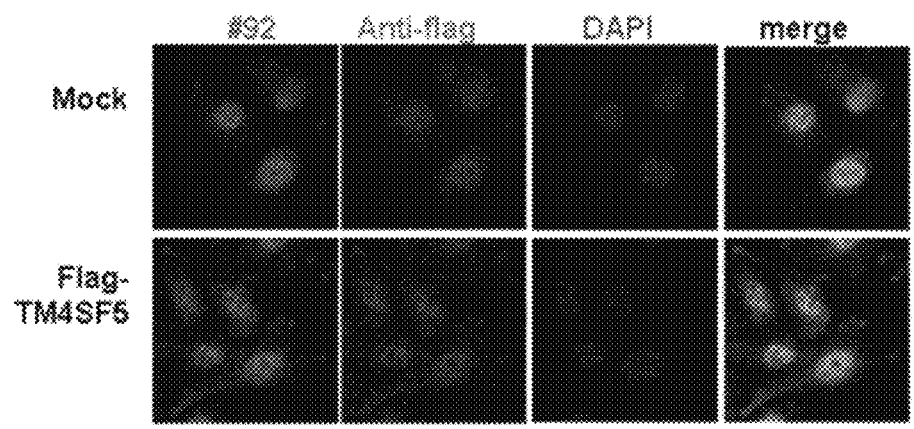

FIG. 11A
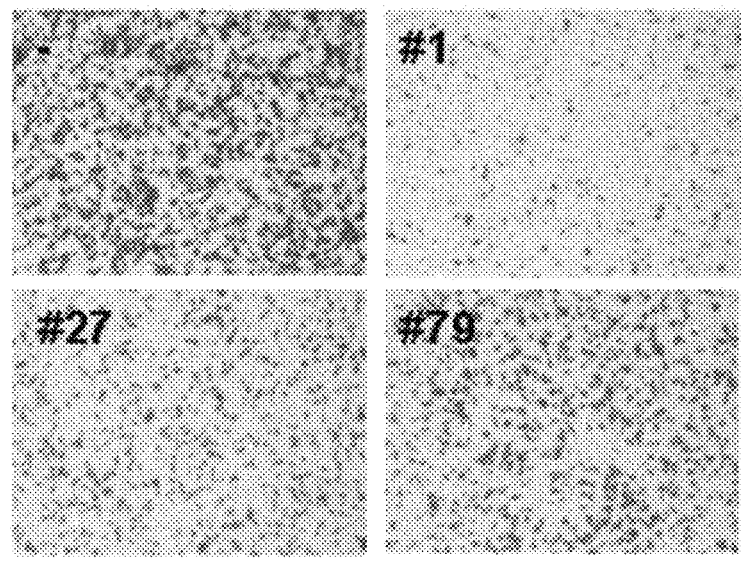
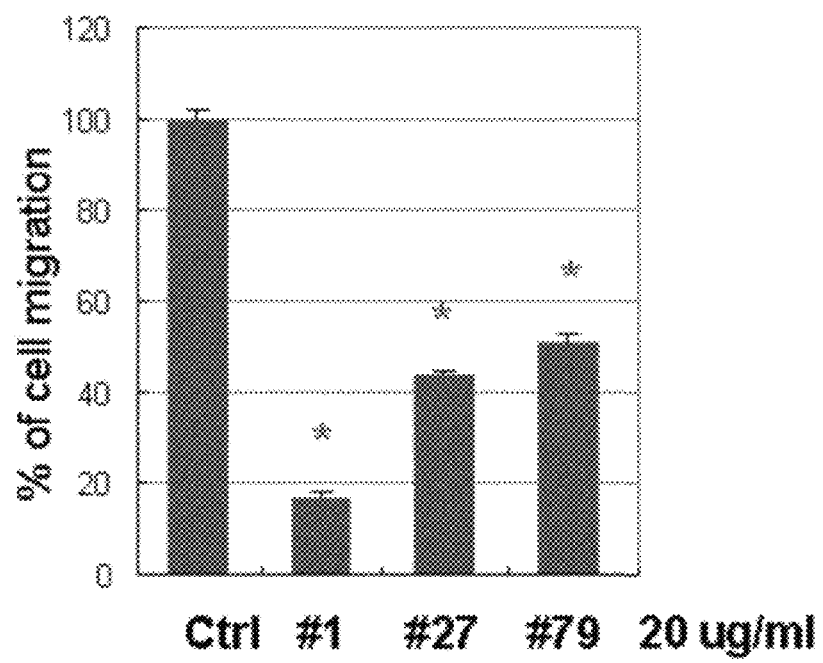

FIG. 11B
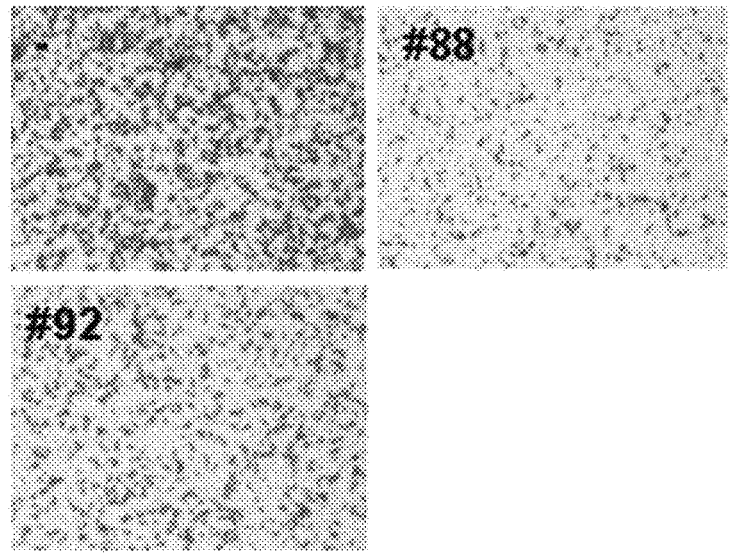
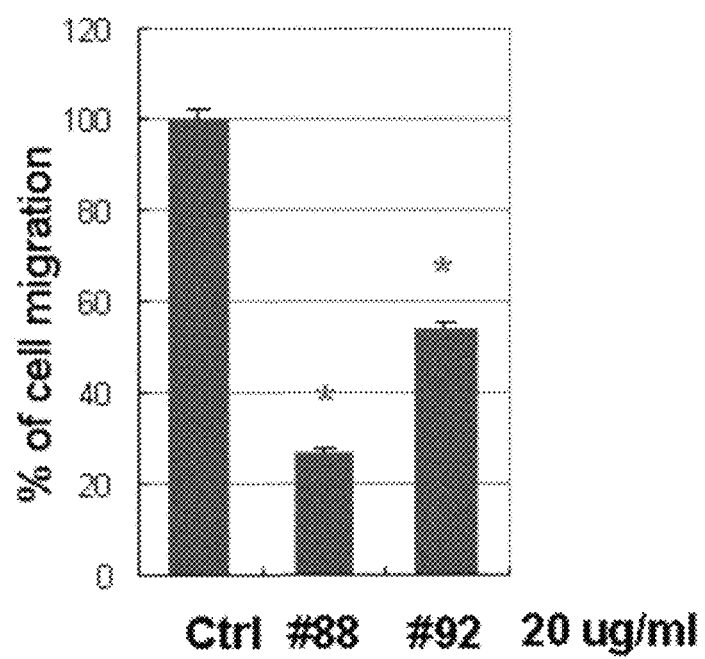

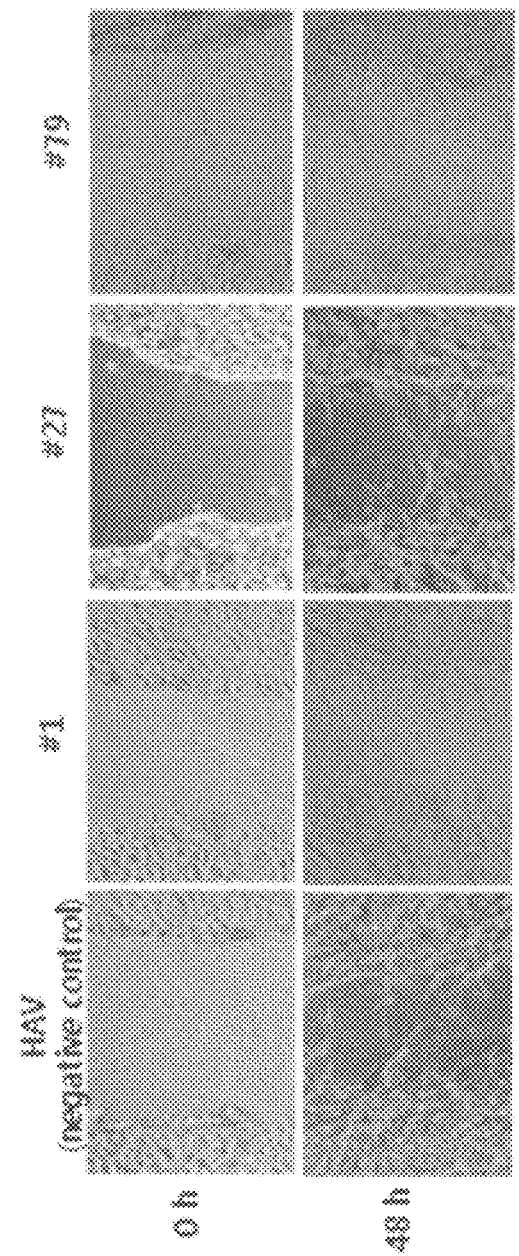

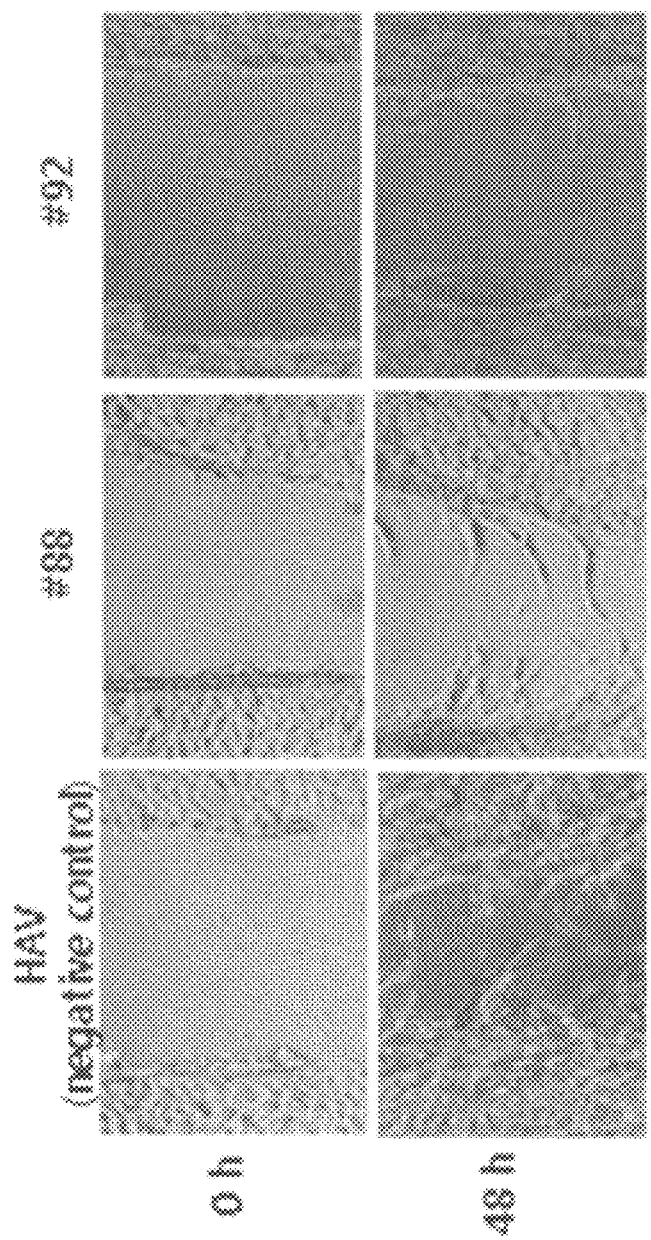

FIG. 14A
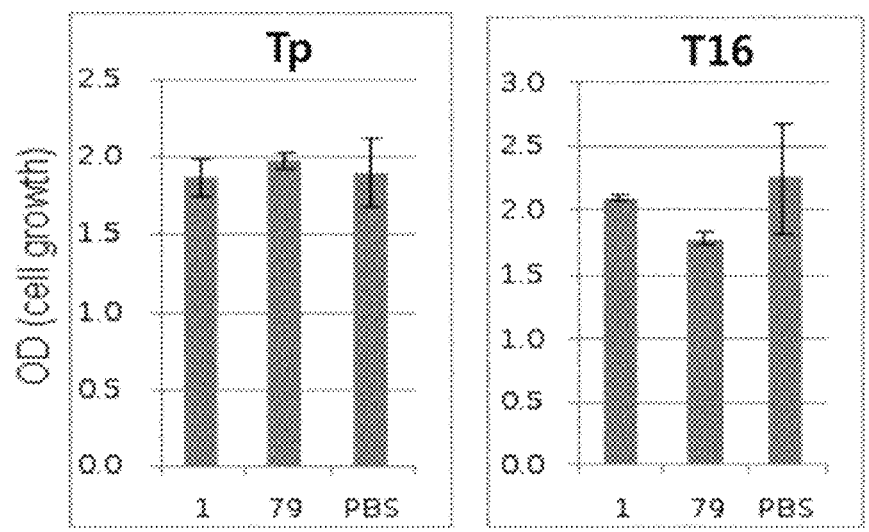
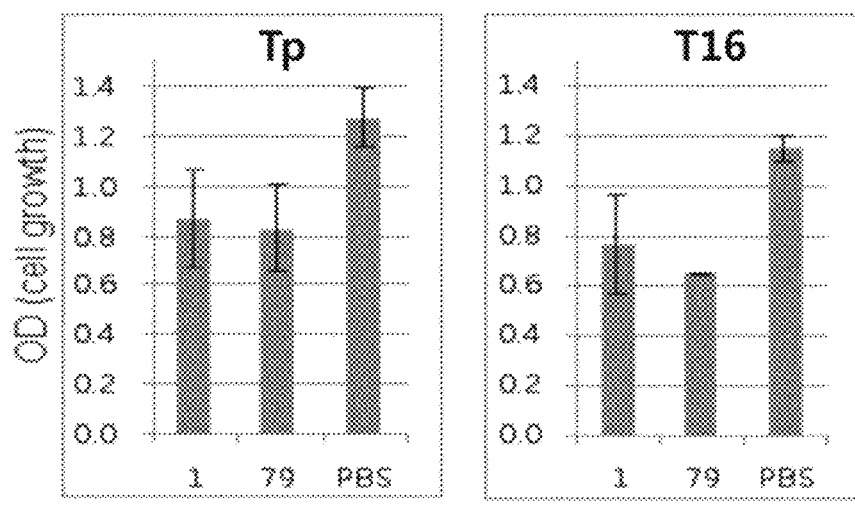

FIG. 14B
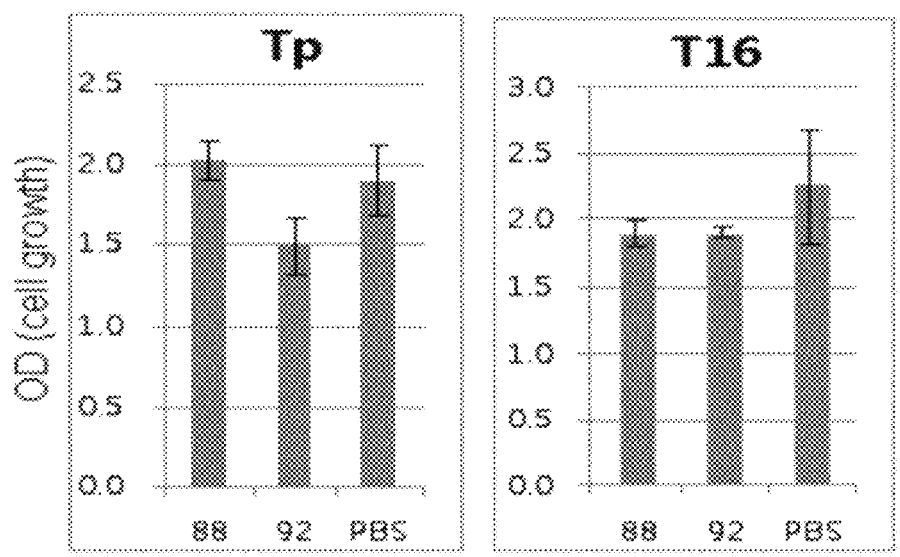
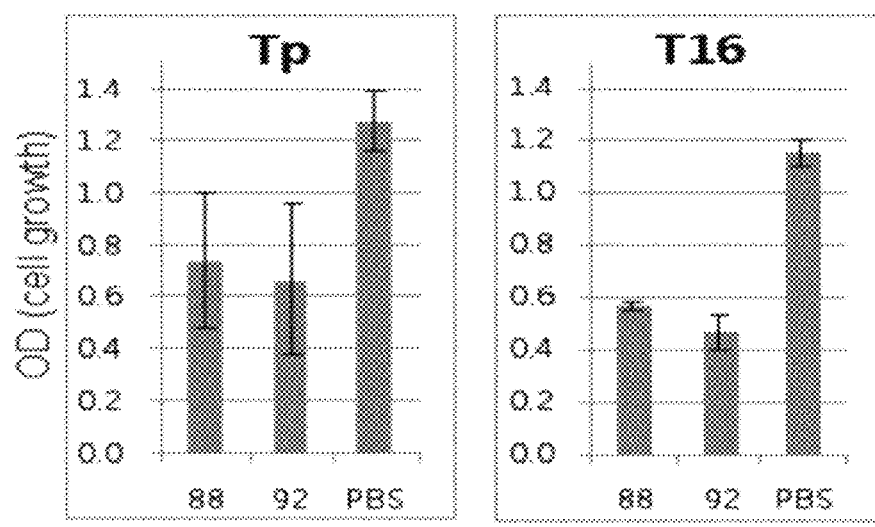

FIG. 15A
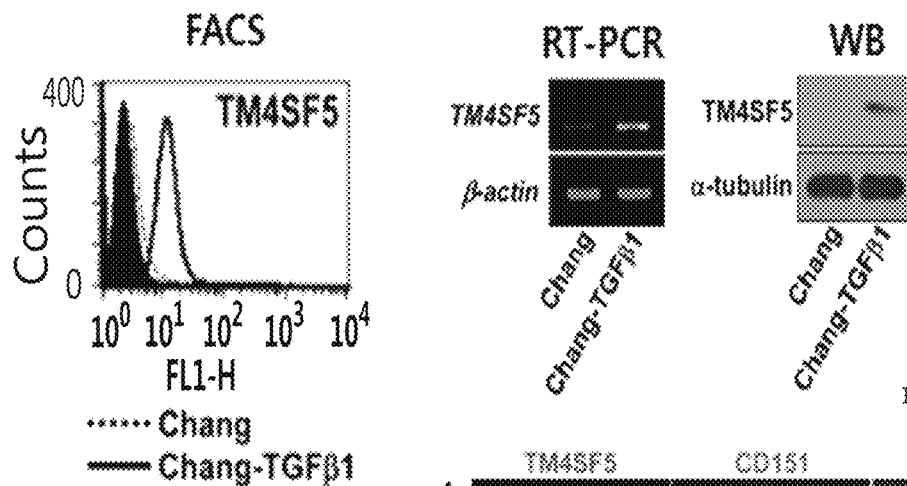
FIG. 15B
FIG. 15C
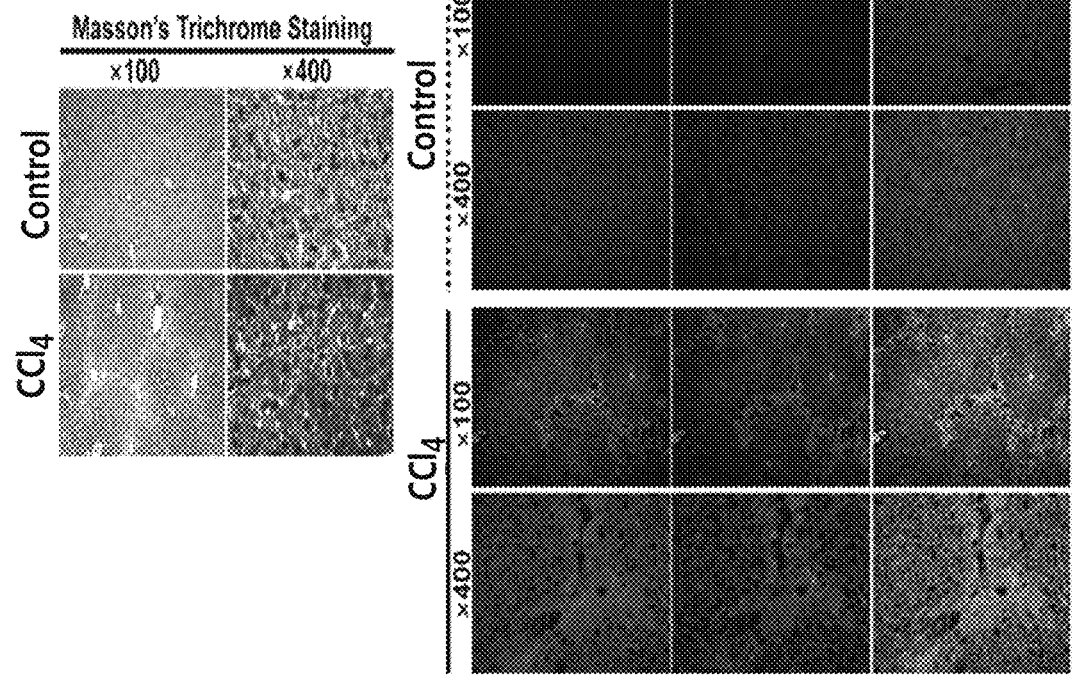

MONOCLONAL ANTIBODY WHICH IS SPECIFICALLY BOUND TO TM4SF5 PROTEIN AND USE THEREOF

BACKGROUND OF THE INVENTION

1. Field of the Invention

The present invention relates to a novel monoclonal antibody that binds specifically to a transmembrane 4 L six family member 5 (TM4SF5) protein, and more particularly, to a monoclonal antibody that binds specifically to a human TM4SF5 protein, a polynucleotide encoding the monoclonal antibody, an expression vector containing the polynucleotide, a transformant having the expression vector introduced therein, a method for preparing the monoclonal antibody, a composition containing the monoclonal antibody, a method for treating cancer or liver fibrosis using the monoclonal antibody, a method for inhibiting metastasis of cancer using the monoclonal antibody, a method for diagnosing cancer or liver fibrosis using the monoclonal antibody, a cancer diagnostic kit including the monoclonal antibody, and a liver fibrosis diagnostic kit including the monoclonal antibody.

2. Description of the Related Art

Generally, transmembrane 4 superfamily (TM4SF) proteins are a group of hydrophobic proteins having a molecular weight of about 25-50 kDa including four transmembrane domains, two extracellular loops, and two short cytoplasmic tail regions, also called tetraspanin or tetraspan. The TM4SF proteins form a complex on the cell membrane along with cell adhesion molecule such as integrin, thereby establishing a gigantic tetraspanin-enriched microdomain (TERM) and contributing to various biological functions such as cell adhesion, proliferation, and migration.

TM4SF5 (transmembrane 4 L six family member 5 or four-transmembrane L6 superfamily member 5) is a member of tetraspanin, and has a structure including four domains of non-soluble proteins which penetrate through cell membranes, two loops present extracellularly, one loop and two tails present in the cytoplasm. TM4SF5 is a homologue of the tumor-associated antigen L6 (TM4SF1), and mRNA of TM4SF5 is known highly overexpressed in the cells of pancreatic cancer, stomach cancer, colorectal cancer, soft tissue sarcoma, etc. Additionally, it was disclosed that an artificial expression of the TM4SF5 protein in COS7 cells could cause actin reorganization and focal adhesion turnover thus suggesting its involvement in cell migration (Lee S A et al., J Clin Invest 2008, 118(4):1354-66). Additionally, the TM4SF5 protein has a high amino acid sequence homology with L6, a cancer-related gene, and thus allegedly suspected as a cancer-associated gene, and also has been reported to be closely associated with the development and progress of cancer. TM4SF5 is involved in cell proliferation by promoting the progress of G1/S cycle through the intracellular p27Kip1 expression and activity of RhoA GTPase (Kim H et al., Biochim Biophys Acta 2010 1803(8):975-82), and the cross-talk in the signaling pathway between transforming growth factor-β1 (TGF-β1) and epidermal growth factor receptor (EGFR), the major factors involved in epithelial-mesenchymal transition (EMT), is known to induce the expression of TM4SF5, thereby bringing about the EMT (Kang M et al., Biochem J 2012 443(3):691-700).

As described above, with the emergence of TM4SF5 as a specific protein and anticancer target for a new cancer diagnosis, studies have been focused on diagnosing cancer having the TM4SF as a target. Additionally, for cancer treatment with the TM4SF as a target, studies have been focused on the inhibition of the biological activities of TM4SF5 in various fields. In particular, there have been studies on the compounds which can inhibit the activities of TM4SF5. For example, among chalcone compounds, sulfonamide- or sulfonate-substituted chalcone derivatives have been reported to inhibit the biological activities of TM4SF5 (KR Patent No. 10-0934706). In addition to the compounds which inhibit the biological activities of TM4SF5, the importance of the studies on the monoclonal antibodies that specifically bind to TM4SF5 has been emphasized. In particular, for clinical studies, there has been raised a need for the development of monoclonal antibodies that can be used for the prevention and treatment of cancer by specifically binding to TM4SF5 and thereby inhibiting the biological activities of TM4SF5.

The present inventors, while endeavoring to find a monoclonal antibody which can specifically bind to human TM4SF5 protein and effectively inhibit biological activities of TM4SF5 proteins such as cancer metastasis, developed monoclonal antibodies that binds specifically to a human TM4SF5 and confirmed that the antibodies can effectively inhibit the biological activities of TM4SF5, thereby completing the present invention.

SUMMARY OF THE INVENTION

One objective of the present invention is to provide a monoclonal antibody which binds specifically to transmembrane 4 L six family member 5 (TM4SF5) protein.

Another objective of the present invention is to provide a method of preparing the monoclonal antibody.

Still another objective of the present invention is to provide a polynucleotide encoding the monoclonal antibody, an expression vector containing the polynucleotide, and a transformant including the expression vector introduced therein.

Still another objective of the present invention is to provide a composition containing the monoclonal antibody.

Still another objective of the present invention is to provide a kit for diagnosing cancer or liver fibrosis containing the monoclonal antibody.

Still another objective of the present invention is to provide a method for treating cancer using the monoclonal antibody.

Still another objective of the present invention is to provide a method for inhibiting metastasis of cancer, the method comprising administering the monoclonal antibody to a subject suspected of having cancer.

Still another objective of the present invention is to provide a method for diagnosing cancer, the method comprising detecting TM4SF5 protein in a biological sample isolated from a subject suspected of having cancer through an antigen-antibody reaction using the monoclonal antibody.

Still another objective of the present invention is to provide a method for treating liver fibrosis, using the antibody.

Still another objective of the present invention is to provide diagnosing liver fibrosis, the method comprising detecting TM4SF5 protein in a biological sample isolated from a subject suspected of having liver fibrosis through an antigen-antibody reaction using the monoclonal antibody.

Advantageous Effects

The TM4SF5-specific monoclonal antibody according to the present invention exhibits a strong affinity for the human TM4SF5 protein and effectively inhibits the biological activities of TM4SF5 such as induction of metastasis of cancer by binding to EC2 region of the TM4SF5. Accordingly, the TM4SF5-specific monoclonal antibody of the present invention can be effectively used for the diagnosis and treatment of TM4SF5-mediated diseases such as liver cancer or liver fibrosis.

DESCRIPTION OF DRAWINGS

FIG. 3 shows the results of sequence analysis of the selected clones and the usage type of human germline immunoglobulins in the variable region of an antibody.

FIGS. 5A to 5E shows the analysis results of the antigen binding affinities of the anti-TM4SF5 antibodies of the present invention. FIG. 5A and FIG. 5B show results of FACS analysis on the control cell line (Cp); and FIG. 5C and FIG. 5D show the results of FACS analysis on TM4SF5-expressing cell line (Tp). Additionally, FIG. 5E shows the results of western blot analysis.

FIGS. 8A to 8F show the images of immunocytochemical analysis using the anti-TM4SF5 antibodies of the present invention and one kind of negative control antibodies (HAV). FIG. 8A shows the results of immunocytochemical analysis using the negative control antibodies (HAV); FIG. 8B shows the results of immunocytochemical analysis using the anti-TM4SF5 antibodies #1; FIG. 8C shows the results of immunocytochemical analysis using the anti-TM4SF5 antibodies #27; FIG. 8D shows the results of immunocytochemical analysis using the anti-TM4SF5 antibodies #79; FIG. 8E shows the results of immunocytochemical analysis using the anti-TM4SF5 antibodies #88; and FIG. 8F shows the results of immunocytochemical analysis using the anti-TM4SF5 antibodies #92, wherein Tp, T7 and T16 represent TM4SF5-overexpressing cells, and Cp represent the control cells.

FIGS. 10A to 10C show the results of co-immunocytochemical analysis using the anti-TM4SF5 antibodies of the present invention and the anti-Flag antibodies, the control antibodies, in the Flag-tagged TM4SF5 (Flag-TM4SF5)-overexpressing cell line.

FIGS. 11A to 11B show the effect of the anti-TM4SF5 antibodies of the present invention on the invasion of the TM4SF5-overexpressing cell line (Tp).

FIGS. 13A to 13B show the results of wound healing assay confirming the effect of the anti-TM4SF5 antibodies of the present invention on cell migration.

FIGS. 14A to 14B show the results confirming the effect of the anti-TM4SF5 antibodies of the present invention on cell growth.

FIGS. 15A to 15C show characterization of anti-TM4SF5 antibody #27 in mouse model, wherein FIG. 15A shows Human Chang hepatocyte activation by TGF-β and TM4SF5 upregulation, FIG. 15B shows CCl4-induced liver fibrosis model (Blue staining: collagen deposition), and FIG. 15C shows liver fibrosis tissue staining of TM4SF5 using Ab#27 (collaboration with SNU).

FIGS. 16A to 16D show characterization of TM4SF5-binding antibodies #27 and #79, wherein FIG. 16A shows the TM4SF5 expression in various cell lines, FIGS. 16B and 16C shows the result of FACS analysis with antibodies #27 and #79, and FIG. 16D shows the result of Internalization assay.

FIGS. 18A to 18C show the results of function-blocking effects of antibodies #27(G) and #79(G), which are TM4SF5-specific antibodies, wherein FIG. 18A shows the result of a proliferation assay, FIG. 18B shows the result of an invasion/migration assay of HCT116, and FIG. 18c shows an invasion/migration assay of Colo205.

FIGS. 19A to 19D show the results of ADCC effects analysis of TM4SF5-specific antibodies, wherein FIG. 19A shows the result of CD16 expression analysis in NK-92 cells, FIG. 19B shows the analysis result of ADCC effect by #27(G) antibody in Tp cells, FIG. 19C shows the analysis result of ADCC effects by #27(G) antibody in Cp, Tp, SNU-398, and HEK293E cells, and FIG. 19D shows the result of ADCC effects analysis by #27(G) antibody in various cancer cell lines.

DETAILS OF THE INVENTION

Figure 1A:
FIG. 1A is a diagram illustrating the structure of the fusion protein construct used in the preparation of an anti-TM4SF5 antibody of the present invention, i.e., the antigen protein construct, which consists of an amino acid region spanning from the $113^{th}$ to $157^{th}$ residues of EC2 (extracellular loop 2) of TM4SF5, His-tag, thrombin cleavage site (TCS), immunoglobulin Fc fragment and Myc-tag.

A better understanding of the present invention may be obtained through the following examples which are set forth to illustrate, but are not to be construed as the limit of the present invention.

In an aspect, the present invention provides a monoclonal antibody which specifically binds to transmembrane 4 L six family member 5 (TM4SF5).

As used herein, the term "antibody" refers to a protein molecule acting as a receptor that specifically recognizes an antigen, including an immunoglobulin molecule immunologically reactive with a specific antigen, and also polyclonal antibodies, monoclonal antibody, whole antibodies and antibody fragments. Additionally, the term also includes chimeric antibodies, humanized antibodies, bivalents or bispecific molecules (e.g., bispecific antibodies), diabodies, triabodies, and tetrabodies. The whole antibodies have two full-length light chains and two full-length heavy chains, and each of the light chains is linked to a heavy chain by a disulfide bond. The whole antibodies include IgA, IgD, IgE, IgM and IgG, and IgG has subtypes of IgG1, IgG2, IgG3 and IgG4. The antibody fragments refer to fragments having a function of binding to antigens including Fab, Fab', F(ab')$_2$, Fv, etc. Fab has a structure consisting of a light chain, a heavy chain variable region, a light chain constant region, and a first heavy chain constant region (CH1 domain) and it includes one antigen-binding site. Fab' differs from Fab in that it has a hinge region including at least one cysteine residue in the C-terminus of the heavy chain CH1 domain. F(ab')$_2$ antibody is formed by a disulfide bond between cysteine residues in the hinge region of Fab'. Fv(variable fragment) refers to a minimum antibody fragment having only a heavy chain variable region and a light chain variable region. A double-chain Fv (dsFv) has a structure where a heavy chain variable region is linked to a light chain variable region by a disulfide bond, and a single-chain Fv (scFv) has a structure where a heavy chain variable region is covalently linked to a light chain variable region by a peptide linker. These antibody fragments can be obtained using a protease (e.g., Fab fragments can be obtained by cleaving the whole antibody with papain, whereas F(ab')$_2$ fragments can be obtained by cleaving the whole antibody with pepsin), and preferably by genetic recombination technology, but is not limited thereto.

As used herein, the term "monoclonal antibody" refers to an antibody molecule that has been obtained from a substantially identical antibody clone, which shows single-binding specificity and affinity for a specific epitope.

Typically, an immunoglobulin has heavy chains and light chains, and each of the heavy chains and the light chains includes a constant region and a variable region (the 'region' is also called 'domain'). The light chain and heavy chain variable regions include three complementarity-determining regions (hereinafter, "CDR") and four framework regions (FR). The CDRs primarily serve to bind to the epitope of an antigen. The CDRs of each chain are typically called CDR1, CDR2, and CDR3 sequentially from the N-terminus, and are also distinguished by the chain where a particular CDR is located.

Meanwhile, the monoclonal antibody, for the purpose of its application in humans, may be in the form of a chimeric or humanized antibody with a reduced antigenicity, as described above.

As used herein, the term "chimeric antibody" refers to an antibody in the form of a recombination obtained by DNA recombination technology between a variable region of a mouse antibody and a constant region of a human antibody. The chimeric antibody has a significantly improved immune response compared to that of the mouse antibodies and thus can be clinically used.

As used herein, the term "humanized antibody" refers to an antibody prepared in such a form, where part or entirety of a CDR sequence of a mouse monoclonal antibody is grafted to a human antibody. For example, the humanized antibody may be obtained by first preparing a humanized variable region by recombination between the CDRs of a mouse monoclonal antibody and human antibody-derived FRs, followed by recombination between the resultant and the constant region of a suitable human antibody, but is not limited thereto. Additionally, considering that the transplantation of only the mouse-derived CDRs would lower the affinity of the humanized antibody, FR amino acid residues that can affect the three-dimensional structure of CDR may be replaced with the amino acids of the mouse antibody to improve the affinity of the humanized antibody, but is not limited thereto.

As used herein, the term "monoclonal antibody that binds specifically to transmembrane 4 L six family member 5 (TM4SF5) protein" refers to an antibody which can bind to a TM4SF5 protein and inhibit the biological activities of the TM4SF5 protein, and may be interchangeably used with the term "anti-TM4SF5 antibody" in the present invention. The monoclonal antibody that binds specifically to the TM4SF5 protein includes without limitation any monoclonal antibodies that can bind to TM4SF5 and thereby inhibit the biological activities of the TM4SF5 protein. Additionally, as described above, the form of the monoclonal antibody may include both the whole antibodies and the antibody fragments, and may be chimeric or humanized antibodies, but is not limited thereto. The monoclonal antibody of the present invention can specifically bind to the extracellular loop 2 or extracellular domain 2 (EC2) of TM4SF5 and inhibit the signaling by TM4SF5 and subsequently inhibit its biological activities such as EMT induction, and thus can be effectively used in the prevention and treatment of diseases such as TM4SF5-mediated cancer or liver fibrosis. Additionally, the overexpression of TM4SF5 has been reported as a specific phenomenon in cancer or liver fibrosis, and thus the antibody of the present invention which can bind specifically to TM4SF5 provides high sensitivity and specificity in diagnosing cancer or liver fibrosis, and thus can be effectively used in cancer or liver fibrosis diagnosis.

Figure 1B:
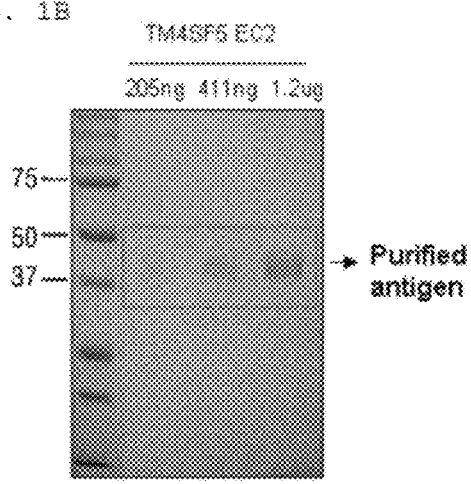
FIG. 1B shows the antigen protein confirmed by SDS-PAGE after its expression and purification.

In an embodiment of the present invention, the monoclonal antibody which binds specifically to TM4SF5 of the present invention was constructed using a fusion protein including the TM4SF5 EC2 region, i.e., the amino acid region spanning from the 113$^{th}$ to 157$^{th}$ residues of TM4SF5, as an antigen protein (FIG. 1).

The monoclonal antibody which binds specifically to TM4SF5 protein may be a monoclonal antibody including:

(a) a heavy chain variable region comprising
a heavy chain CDR1 represented by SEQ ID NO: 2; a heavy chain CDR2 represented by SEQ ID NO: 3; and a heavy chain CDR3 represented by SEQ ID NO: 4, 12, 20, or 26;
and a light chain variable region comprising a light chain CDR1 represented by SEQ ID NO: 6 or 14; a light chain CDR2 represented by SEQ ID NO: 7 or 15; and a light chain CDR3 represented by SEQ ID NO: 8, 16, 22, or 28; or (b) a heavy chain variable region comprising
a heavy chain CDR1 represented by SEQ ID NO: 32; a heavy chain CDR2 represented by SEQ ID NO: 33; and a heavy chain CDR3 represented by SEQ ID NO: 34; and
a light chain variable region comprising a light chain CDR1 represented by SEQ ID NO: 36; a light chain CDR2 represented by SEQ ID NO: 15; and a light chain CDR3 represented by SEQ ID NO: 37.

The monoclonal antibody which binds specifically to TM4SF5 protein may be preferably a monoclonal antibody including:

a heavy chain variable region including a heavy chain CDR1 represented by SEQ ID NO: 2, a heavy chain CDR2 represented by SEQ ID NO: 3, and a heavy chain CDR3 represented by SEQ ID NO: 4; and a light chain variable region including a light chain CDR1 represented by SEQ ID NO: 6, a light chain CDR2 represented by SEQ ID NO: 7, and a light chain CDR3 represented by SEQ ID NO: 8, and more preferably, a monoclonal antibody including a heavy chain variable region represented by SEQ ID NO: 1, and a light chain variable region represented by SEQ ID NO: 5, but is not limited thereto.

In an embodiment of the present invention, the monoclonal antibody including the heavy chain variable region represented by SEQ ID NO: 1; and the light chain variable region represented by SEQ ID NO: 5 was assigned as monoclonal antibody #1.

A polynucleotide encoding the monoclonal antibody may include a polynucleotide sequence encoding a heavy chain variable region represented by SEQ ID NO: 9, and a polynucleotide sequence encoding a light chain variable region represented by SEQ ID NO: 10, but is not limited thereto.

The monoclonal antibody which binds specifically to TM4SF5 protein may be preferably a monoclonal antibody including: a heavy chain variable region including a heavy chain CDR1 represented by SEQ ID NO: 2, a heavy chain CDR2 represented by SEQ ID NO: 3, and a heavy chain CDR3 represented by SEQ ID NO: 12; and a light chain variable region including a light chain CDR1 represented by SEQ ID NO: 14, a light chain CDR2 represented by SEQ ID NO: 15, and a light chain CDR3 represented by SEQ ID NO: 16, and more preferably, a monoclonal antibody including a heavy chain variable region represented by SEQ ID NO: 11, and a light chain variable region represented by SEQ ID NO: 13, but is not limited thereto.

In an embodiment of the present invention, the monoclonal antibody including the heavy chain variable region represented by SEQ ID NO: 11; and the light chain variable region represented by SEQ ID NO: 13 was assigned as monoclonal antibody #27.

A polynucleotide encoding the monoclonal antibody may include a polynucleotide sequence encoding a heavy chain variable region represented by SEQ ID NO: 17, and a polynucleotide sequence encoding a light chain variable region represented by SEQ ID NO: 18, but is not limited thereto.

Additionally, the monoclonal antibody which binds specifically to TM4SF5 protein may be preferably a monoclonal antibody including: a heavy chain variable region including a heavy chain CDR1 represented by SEQ ID NO: 2, a heavy chain CDR2 represented by SEQ ID NO: 3, and a heavy chain CDR3 represented by SEQ ID NO: 20; and a light chain variable region including a light chain CDR1 represented by SEQ ID NO: 14, a light chain CDR2 represented by SEQ ID NO: 15, and a light chain CDR3 represented by SEQ ID NO: 22, and more preferably, a monoclonal antibody including a heavy chain variable region represented by SEQ ID NO: 19, and a light chain variable region represented by SEQ ID NO: 21, but is not limited thereto.

In an embodiment of the present invention, the monoclonal antibody including the heavy chain variable region represented by SEQ ID NO: 19; and the light chain variable region represented by SEQ ID NO: 21 was assigned as monoclonal antibody #79.

A polynucleotide encoding the monoclonal antibody may include a polynucleotide sequence encoding a heavy chain variable region represented by SEQ ID NO: 23, and a polynucleotide sequence encoding a light chain variable region represented by SEQ ID NO: 24, but is not limited thereto.

Additionally, the monoclonal antibody which binds specifically to TM4SF5 protein may be preferably a monoclonal antibody including: a heavy chain variable region including a heavy chain CDR1 represented by SEQ ID NO: 2; a heavy chain CDR2 represented by SEQ ID NO: 3; and a heavy chain CDR3 represented by SEQ ID NO: 26; and a light chain variable region including a light chain CDR1 represented by SEQ ID NO: 14; a light chain CDR2 represented by SEQ ID NO: 15; and a light chain CDR3 represented by SEQ ID NO: 28, and more preferably, a monoclonal antibody including a heavy chain variable region represented by SEQ ID NO: 25; and a light chain variable region represented by SEQ ID NO: 27, but is not limited thereto.

In an embodiment of the present invention, the monoclonal antibody including the heavy chain variable region represented by SEQ ID NO: 25; and the light chain variable region represented by SEQ ID NO: 27 was assigned as monoclonal antibody #88.

A polynucleotide encoding the monoclonal antibody may include a polynucleotide sequence encoding a heavy chain variable region represented by SEQ ID NO: 29, and a polynucleotide sequence encoding a light chain variable region represented by SEQ ID NO: 30, but is not limited thereto.

Additionally, the monoclonal antibody which binds specifically to TM4SF5 protein may be preferably a monoclonal antibody including: a heavy chain variable region including a heavy chain CDR1 represented by SEQ ID NO: 32, a heavy chain CDR2 represented by SEQ ID NO: 33, and a heavy chain CDR3 represented by SEQ ID NO: 34; and a light chain variable region including a light chain CDR1 represented by SEQ ID NO: 36, a light chain CDR2 represented by SEQ ID NO: 15, and a light chain CDR3 represented by SEQ ID NO: 37, and more preferably, a monoclonal antibody including a heavy chain variable region represented by SEQ ID NO: 31; and a light chain variable region represented by SEQ ID NO: 35, but is not limited thereto.

In an embodiment of the present invention, the monoclonal antibody including the heavy chain variable region represented by SEQ ID NO: 31; and the light chain variable region represented by SEQ ID NO: 35 was assigned as monoclonal antibody #92.

A polynucleotide encoding the monoclonal antibody may include a polynucleotide sequence encoding a heavy chain variable region represented by SEQ ID NO: 38, and a polynucleotide sequence encoding a light chain variable region represented by SEQ ID NO: 39, but is not limited thereto.

Additionally, when the monoclonal antibody of the present invention includes a constant region, the monoclonal antibody may include IgG-, IgA-, IgD-, IgE-, and IgM-derived constant regions, combinations thereof or hybrids thereof.

As used herein, the term "combination" refers to forming a linkage between a polypeptide encoding a single-chain immunoglobulin constant region of the same origin and a single-chain polypeptide of a different origin to form a dimer or multimer. For example, the dimer or multimer may be formed from two or more constant regions selected from the group consisting of IgG, IgA, IgD, IgE and IgM constant regions.

As used herein, the term "hybrid" refers to the presence of sequences encoding two or more immunoglobulin heavy chain constant regions of different origins in a single-chain immunoglobulin heavy chain constant region. For example, domain hybrids may be composed of one to four domains selected from CH1, CH2, CH3 and CH4 of IgG, IgA, IgD, IgE and IgM.

Meanwhile, combinations or hybrids of $IgG_1$, $IgG_2$, $IgG_3$, and $IgG_4$ heavy chain constant regions, i.e., subtypes of IgG, are also possible. The combinations and hybrids are the same as described above.

Additionally, when the monoclonal antibody that binds specifically to TM4SF5 includes a light chain constant region, the light chain constant region may be of lambda ($\lambda$) or kappa ($\kappa$) light chain origin, but is not limited thereto.

As used herein, the term "transmembrane 4 L six family member 5 (TM4SF5) protein" refers to a protein, being a kind belonging to transmembrane 4 superfamily (TM4SF) which is a membrane receptor group penetrating through cell membranes four times, which mediates signaling pathways associated with the regulation of cell development, activation, growth and migration. The TM4SF5 protein has a structure consisting of four transmembrane domains which penetrate through membranes, two extracellular loops, one intracellular cytoplasmic loop, and two tail regions, wherein, of the two extracellular loops, the second external loop (extracellular loop 2; EC2) is longer than the first external loop (extracellular loop 1; EC1), and the major amino acid residues involved in the interactions with other molecules are present in EC2. The kind of TM4SF5 proteins is not particularly limited, but preferably the human TM4SF5 protein. Additionally, TM4SF5 proteins include both wild-type and mutant TM4SF5 proteins, but are not limited thereto. The natural-type TM4SF5 protein generally refers to a polypeptide including the amino acid sequence of the wild-type TM4SF5 protein, and the wild-type TM4SF5 protein generally refers to the amino acid sequence found in the naturally-occurring TM4SF5 protein. The information on TM4SF5 protein can be obtained from the known databases, including GenBank of the National Institutes of Health, and may be, for example, GenBank Accession Number NP_003954(Gene ID: 9032), but is not limited. In cancer, TM4SF5 proteins induce epithelial-mesenchymal transition (EMT), which is involved in occurrence, invasion or metastasis of cancer, and causes the loss of contact inhibition of cells thereby leading to a multilayer growth (Lee S A et al., J Clin Invest 2008, 118(4):1354-66). Additionally, TM4SF5 proteins interact with integrin α 5 intracellularly to thereby activate the signaling process of FAK/c-Src/STAT3 and cause the expression and secretion of vascular endothelial growth factor (VEGF), an important factor in angiogenesis, thereby causing angiogenesis of vascular endothelial cells (Choi S et al., Blood 2009 113 (8):1845-55). Accordingly, any material which can inhibit the function of TM4SF5 can exhibit an anticancer effect (KR Patent No. 10-0934706), and thus the monoclonal antibody of the present invention, which binds specifically to TM4SF5 proteins, can be effectively used for the prevention and treatment of cancer.

In another aspect, the present invention provides a method for preparing the monoclonal antibody described above.

The monoclonal antibody of the present invention can be easily prepared using conventional monoclonal antibody production technology. For example, the method for preparing the monoclonal antibody may be performed by producing a hybridoma using B lymphocytes obtained from immunized animals (Koeher and Milstein, 1976, Nature, 256:495) or may be performed using phage display technology, but is not limited thereto.

An antibody library using a phage display is a method of expressing an antibody on the surface of a phage with the gene of the antibody directly obtained from B lymphocytes without the preparation of hybridoma. Many of the existing difficulties associated with the monoclonal antibody production via B-cell immortalization can be overcome by the phage display method. A conventional phage display method includes: 1) inserting an oligonucleotide with a random sequence into the region corresponding to the N-terminus of a phage coat protein pIII (or pIV); 2) expressing a fusion protein between a part of a natural-type coat protein and a polypeptide encoded by the oligonucleotide having a random sequence; 3) treating a receptor material that can bind to the polypeptide encoded by the oligonucleotide having a random sequence; 4) eluting peptide-phage particles bound to the receptors at a low pH condition or using a molecule with a binding competitiveness; 5) amplifying the eluted phage in a host cell by panning; 6) repeating the above steps to obtain a desired amount of phage; and 7) determining the sequence of an active peptide from the DNA sequence of the phage clones selected by panning.

Preferably, the method for preparing the inventive monoclonal antibody may be performed by a phage display method. A person skilled in the art can easily perform each of the above steps with reference to well-known phage display techniques disclosed in, for example, Barbas et al. (METHODS: A Companion to Methods in Enzymology 2:119, 1991 and J. Virol. 2001 July; 75(14):6692-9) and Winter et al. (Ann. Rev. Immunol. 12:433, 1994). Examples of the phage to be used for constructing the antibody library include filamentous phages such as fd, M13, f1, If1, Ike, Zj/Z, Ff, Xf, Pf1 and Pf3, but are not limited thereto. Also, examples of the vector to be used in the expression of a heterogeneous gene on the surface of the filamentous phages include phage vectors such as fUSE5, fAFF1, fd-CAT1 or fdtetDOG, or phagemid vectors such as pHEN1, pComb3, pComb8 or pSEX, but are not limited thereto. Further, examples of the helper phage to be used to provide a wild-type coat protein required for a successful re-infection of a recombinant phage include M13K07 and VSCM13, but are not limited thereto.

A polynucleotide encoding the hybridoma-derived monoclonal antibody or phase display clone can be readily isolated and sequenced using conventional procedures, for example, oligonucleotide primers designed to specifically amplify the heavy chain and light chain regions of interest from a hybridoma or phage template DNA may be used. Once the polynucleotide is isolated, it can be inserted into an expression vector, which is then transformed into a suitable host cell, and the desired monoclonal antibody can be obtained from the transformed host cell (i.e., transformants). Accordingly, the method for preparing the human monoclonal antibody may include amplifying an expression vector containing a polynucleotide encoding the human monoclonal antibody, but is not limited thereto.

In another aspect, the present invention provides a polynucleotide encoding the monoclonal antibody, an expression vector containing the polynucleotide, and a transformant having the expression vector introduced therein.

The monoclonal antibody is the same as described above.

An expression vector containing a polynucleotide encoding the monoclonal antibody according to the present invention may include, although not particularly limited thereto, a vector capable of replicating and/or expressing the polynucleotide in eukaryotic or prokaryotic cells, including mammalian cells (e.g., human-, monkey-, rabbit-, rat-, hamster-, mouse cells, etc.), plant cells, yeast cells, insect cells and bacterial cells (e.g., *E. coli*), and preferably, a vector, which contains at least one selective marker and is operably linked to a suitable promoter so that the polynucleotide can be expressed in a given host cell. For example, the vector may include the polynucleotide introduced into a phage-, plasmid-, cosmid-, mini-chromosome-, virus- or retrovirus vector, etc.

The expression vector containing the polynucleotide encoding the polynucleotide may be either an expression vector having the heavy chain or light chain of the monoclonal antibody, or an expression vector containing both polynucleotides encoding the heavy chain and light chain of the monoclonal antibody.

The transformants into which the expression vector of the present invention were introduced thereinto may include, although not limited thereto, bacterial cells such as *E. coli*, *Streptomyces* and *Salmonella typhimurium*; fungal cells such as yeast cells including *Pichia pastoris*; insect cells such as *Drosophila* or *Spodoptera* Sf9 cells; animal cells such as Chinese hamster ovary (CHO) cells, SP2/0 (mouse myeloma), human lymphoblastoid, COS, mouse myeloma (NSO), 293T, Bowes melanoma cells, HT-1080, baby hamster kidney (BHK) cells, human embryonic kidney (HEK) cells, PERC.6 (human retinal cells), and the like; and plant cells, which were transformed by the introduction of expression vectors.

As used herein, the term "introduction" refers to a method of delivering the vector containing the polynucleotide encoding the monoclonal antibody into a host cell. This introduction may be performed by various methods known in the art, including calcium phosphate-DNA co-precipitation, DEAE-dextran-mediated transfection, polybrene-mediated transfection, electroporation, microinjection, liposome fusion, lipofection and protoplast fusion. Additionally, transfection refers to a delivery of a desired material into a cell via infection using viral particles. In addition, the vector may be introduced into a host cell by gene bombardment. In the present invention, the term "introduction" may be used interchangeably with the term "transfection".

In another aspect, the present invention provides a composition containing the monoclonal antibody. The composition may be in the form of a pharmaceutical composition or a composition for diagnosis.

The composition may be a pharmaceutical composition or a composition for preventing or treating cancer.

The monoclonal antibody of the present invention binds specifically to TM4SF5, blocks effectively the TM4SF5-mediated signals, and inhibits the biological activities of TM4SF5, whereby it can be involved in the prevention and treatment of cancer. TM4SF5 and monoclonal antibody are the same as described above.

As used herein, the term "cancer" refers to any kind of cancer that can express TM4SF5 protein and may include, but are not limited to, for example, esophageal cancer, stomach cancer, colorectal cancer, rectal cancer, oral cancer, pharyngeal cancer, laryngeal cancer, lung cancer, colon cancer, breast cancer, cervical cancer, endometrial cancer, ovarian cancer, prostate cancer, testicular cancer, bladder cancer, renal cancer, liver cancer, pancreatic cancer, bone cancer, connective tissue cancer, skin cancer, brain cancer, thyroid cancer, leukemia, Hodgkin's disease, soft tissue sarcoma, lymphoma, multiple myeloma, or blood cancer.

As used herein, the term "prevention" may refer to all kinds of actions that can inhibit or delay the development of cancer by administering the composition, and the term "treatment" may refer to all actions that can restore or beneficially change the symptoms of cancer by administering the composition.

The pharmaceutical composition may further contain a pharmaceutically acceptable carrier.

As used herein, the term "pharmaceutically acceptable carrier" refers to a carrier or diluent that neither cause an irritation to an organism nor inhibit the biological activities and properties of the administered compound. Examples of the pharmaceutically acceptable carriers to be used to formulate the inventive composition in the form of liquid solutions, may include saline solution, sterile water, Ringer's solution, buffered saline solution, albumin injection solution, dextrose solution, maltodextrin solution, glycerol, ethanol, and a mixture of two or more thereof, and upon necessity, may also contain other conventional additives, such as antioxidants, buffers and bacteriostatic agents. Additionally, the composition may further contain diluents, dispersants, surfactants, binders and lubricants in order to formulate it into injectable formulations, such as aqueous solutions, suspensions and emulsions, pills, capsules, granules or tablets.

The pharmaceutical composition may be in the form of various oral or parenteral formulations. The pharmaceutical composition is formulated using conventional diluents or excipients, including fillers, extenders, binders, wetting agents, disintegrants, and surfactants. Solid formulations for oral administration include tablets, pills, powders, granules, capsules, etc. These solid formulations are prepared by mixing at least one compound with at least one excipient, e.g., starch, calcium carbonate, sucrose or lactose, gelatin, etc. In addition to simple excipients, lubricants such as magnesium stearate and talc may also be used. Additionally, liquid formulations for oral administration may include suspensions, solutions for internal use, emulsions, syrups, etc. In addition to the commonly-used simple diluents such as water and liquid paraffin, various excipients, e.g., wetting agents, sweetening agents, flavors, preservatives, etc., may be included. Formulations for parenteral administration include sterile aqueous solutions, non-aqueous solvents, suspending agents, emulsions, lyophilized agents, suppositories. Propylene glycol, polyethylene glycol, vegetable oils such as olive oil, injectable esters such as ethyl oleate, etc., may be used as non-aqueous solvents and suspending agents. Bases for suppositories may include witepsol, macrogol, tween 61, cacao butter, laurin butter, glycerinated gelatin, etc.

The pharmaceutical composition may be prepared in any one formulation selected from the group consisting of a tablet, a pill, powder, granules, a capsule, a suspension, a solution for internal use, an emulsion, a syrup, a sterile aqueous solution, a non-aqueous solution, a suspension, a lyophilized formulation, and a suppository.

The composition of the present invention may be administered in a pharmaceutically effective amount.

As used herein, the term "pharmaceutically effective amount" refers to an amount sufficient to treat diseases, at a reasonable benefit/risk ratio applicable to any medical treatment. The effective dosage level of the composition may be determined depending on the subject's type, severity of disease, sex and age of the subject, type of cancer, the activities of the drug, sensitivity to the drug, duration of administration, administration route, excretion rate, length of treatment, drugs used in combination with the composition, and other well-known factors in the medical field. The composition of the present invention may be administered alone or in combination with other therapeutic agents, and sequentially or simultaneously with conventional therapeutic agents. The composition can be administered in a single or multiple dosage form. It is important to administer the composition in a minimum amount that can exhibit the maximum effect without causing side effects, in view of all the above-described factors, and the dose can be easily determined by those skilled in the art.

Additionally, the composition may be a pharmaceutical composition for inhibiting metastasis of cancer.

The cancer is as described above. According to one embodiment of the present invention, the metastasis of cancer may be liver metastasis of cancer, but is not limited thereto.

As used herein, the term "metastasis" refers to a migration of cancer cells to a different part of the body and subsequent settlement and proliferation of the cancer cells. The anti-TM4SF5 monoclonal antibody of the present invention inhibits effectively the migration of liver cancer cells and thus the composition containing the monoclonal antibody can be used for the inhibiting the liver metastasis of cancer cells.

In an embodiment of the present invention, the anti-TM4SF5 antibodies #1, #27, #79, #88 and #92 of the present invention were shown to bind specifically to TM4SF5 (FIGS. 5A to 5E, 7, 8A to 8F and 10A to 10C), significantly reduce the transwell and cell motility of TM4SF5-overexpressing liver cancer cells (FIGS. 11 to 13), and reduce the proliferation of liver cancer cells in the absence of blood serum (FIGS. 14A and 14B), thus confirming that the pharmaceutical composition containing the antibody of the present invention can be effectively used for the prevention and treatment of cancer.

Additionally, the composition may be a pharmaceutical composition for preventing or treating liver fibrosis.

As used herein, the term "liver fibrosis" refers to a scarring process occurring after liver injury. Fibrosis itself causes no symptoms but can lead to portal hypertension cirrhosis or liver cancer.

The general details of the pharmaceutical composition are the same as described above.

Additionally, the composition may be a pharmaceutical composition for diagnosing cancer.

The diseases associated with the presence of expression or expression level of TM4SF5 or TM4SF5-mediated diseases can be diagnosed by detecting TM4SF5 using a composition containing the monoclonal antibody, which binds specifically to TM4SF5, and in particular, TM4SF5 can be used for cancer diagnosis because it is overexpressed in various types of cancer such as colorectal cancer, liver cancer, and pancreatic cancer.

In an embodiment of the present invention, the anti-TM4SF5 antibodies of the present invention specifically recognized TM4SF5, and that it had a much higher detection capability than the commercially available TM4SF5 polyclonal antibodies (FIGS. 5A to 5E, to 10C), thus indicating that the antibody of the present invention can be effectively used for the diagnosis of various cancer including liver cancer.

Additionally, the composition may be a pharmaceutical composition for diagnosing liver fibrosis.

It was reported that the expression of TM4SF5 was induced by TGF-β in hepatocytes thereby inducing liver fibrosis (FEBS J (2012) 279:625-635). Accordingly, TM4SF5, being a major factor inducing liver fibrosis, which is a precursor step to the development of liver cancer, and liver cancer, and thus liver fibrosis can be diagnosed by measuring the level of TM4SF5 using the antibodies of the present invention.

In another aspect, the present invention provides a kit for diagnosing cancer containing the monoclonal antibody for diagnosing cancer.

The composition and cancer are the same as described above. Additionally, the kit for diagnosing cancer may further include a composition containing at least one kind of constituting component suitable for the analysis, a solution, or a device.

In another aspect, the present invention provides a kit for diagnosing liver fibrosis containing the monoclonal antibody for diagnosing liver fibrosis.

The composition and cancer are the same as described above. Additionally, the kit for diagnosing liver fibrosis may further include a composition containing at least one kind of constituting component suitable for the analysis, a solution, or a device.

In another aspect, the present invention provides a method for treating cancer using the monoclonal antibody.

The monoclonal antibody and cancer are the same as described above. The method for treating cancer may be a method including administering a pharmaceutical composition containing the monoclonal antibody of the present invention and additionally a pharmaceutically acceptable carrier to a subject having or suspected of having cancer. The pharmaceutically acceptable carrier is the same as described above. Preferably, the method for treating cancer may be a method including administering a composition containing the monoclonal antibody of the present invention to a subject of having cancer. The subject includes mammals including cattle, pigs, sheep, chickens, dogs, and human, and birds, and includes without limitation any subject, in which the cancer can be treated by administering the composition of the present invention.

The composition may be administered in a pharmaceutically effective amount in a single or multiple dosage form. In particular, the composition may be administered in the form of a liquid, powder, aerosol, capsule, enteric coated tablet or capsule, or suppository. Additionally, the composition may be administered intraperitoneally, intravenously, intramuscularly, subcutaneously, intradermally, orally, topically, intranasally, intrapulmonarily or intrarectally, but is not limited thereto. However, when the composition is administered orally, the peptide is digested in the stomach, and thus, the oral composition should be formulated so that the active ingredient is coated or protected from decomposition in the stomach. Additionally, the pharmaceutical composition may be administered via any system which can deliver the active ingredient to a target cell.

Since the pharmaceutical composition of the present invention contains the monoclonal antibody of the present invention which binds specifically to TM4SF5, the administration of the pharmaceutical composition containing the monoclonal antibody in the body can inhibit or block the occurrence, proliferation or metastasis of cancer, or treat cancer by inhibiting the progresses thereof.

In another aspect, the present invention provides a method for inhibiting metastasis of cancer by administering the monoclonal antibody to a subject in need thereof.

The monoclonal antibody, TM4SF5 protein, metastasis, cancer and administration are the same as described above.

In another aspect, the present invention provides a method for treating liver fibrosis by administering the monoclonal antibody to a subject suspected of having liver fibrosis.

The details of the monoclonal antibody, liver fibrosis, and administration are the same as described above.

In another aspect, the present invention provides a method for diagnosing cancer including detecting the TM4SF5 protein in a biological sample, isolated from a subject suspected of having cancer, by an antigen-antibody reaction using the monoclonal antibody. The monoclonal antibody, cancer, subject, and TM4SF5 protein are the same as described above.

In the method for diagnosing cancer, the TM4SF5 protein can be detected by reacting the TM4SF5-specific monoclonal antibody with the biological sample isolated from the subject suspected of having cancer, and detecting the formation of an antigen-antibody complex, whereby cancer can be diagnosed.

Since TM4SF5 is overexpressed in various cancer cells, including the cells in liver cancer, colorectal cancer or pancreatic cancer, cancer can be diagnosed by comparing the expression level of TM4SF5 in the biological sample with that in a control group such as a normal cell or tissue, but is not limited thereto.

As used herein, the term "biological sample" may include a tissue, a cell, whole blood, serum, plasma, a tissue autopsy sample (e.g., brain, skin, lymph node, spinal cord, etc.), a cell culture supernatant, a ruptured eukaryotic cell, and a bacterial expression system, but is not limited thereto. These biological samples can be reacted with the monoclonal antibody in a manipulated or non-manipulated state in order to determine the presence of the TM4SF5 protein or the presence/absence of cancer.

As used herein, the term "antigen-antibody complex" refers to a conjugate between the TM4SF5 protein antigen in the sample and the monoclonal antibody recognizing the TM4SF5 protein antigen. The formation of this antigen-antibody complex can be detected by any method selected from the group consisting of a colorimetric method, an electrochemical method, a fluorimetric method, luminometry, a particle counting method, visual assessment, and a scintillation counting method, but is not limited thereto, and various methods may be used and applied.

In the present invention, various labels may be used to detect the antigen-antibody complex. Specific examples of the label may include, although not limited thereto, enzymes, fluorescent materials, ligands, luminescent materials, microparticles, and radioactive isotopes.

Examples of the enzymes that may be used as the detection label include acetylcholinesterase, alkaline phosphatase, β-D-galactosidase, horseradish peroxidase, and β-latamase. Examples of the fluorescent materials include fluorescein, $Eu^{3+}$, $Eu^{3+}$ chelate, cryptate, etc. Examples of the ligands include biotin derivatives, etc. Examples of the luminescent materials include acridinium ester, isoluminol derivatives, etc. Additionally, examples of the microparticles include colloidal gold, colored latex, etc. Examples of the radioactive isotopes include $^{57}Co$, $^{3}H$, $^{125}I$, and $^{125}I$-Bonton Hunter reagents.

Preferably, the antigen-antibody complex may be detected by an ELISA method. Examples of the ELISA method include a direct ELISA using a labeled antibody capable of recognizing an antigen attached to a solid support, an indirect ELISA using a labeled secondary antibody capable of recognizing a capture antibody in an antibody complex capable of recognizing an antigen attached to a solid support, a direct sandwich ELISA which uses another labeled antibody capable of recognizing an antigen in an antigen-antibody complex attached to a solid support, and an indirect sandwich ELISA, which includes reacting another antibody with an antigen in an antigen-antibody complex attached to a solid support and then using the labeled secondary antibody capable of recognizing the antibody, etc.

The monoclonal antibody may have a detection label. When the monoclonal antibody has no detection label, it can be captured and detected by treating with another antibody having a detection label.

In another aspect, the present invention provides a method for diagnosing liver fibrosis including detecting TM4SF5 protein in a biological sample isolated from a subject suspected of having liver fibrosis through an antigen-antibody reaction using the monoclonal antibody.

The details of liver fibrosis, TM4SF5 protein, an antigen-antibody reaction, etc., are the same as described above.

Specifically, when the level of TM4SF5 protein in the biological sample isolated from the subject suspected of having liver fibrosis is higher than that of normal group the subject may be diagnosed as having liver fibrosis, but is not limited thereto.

Hereinafter, the present invention will be described in more detail with reference to Examples. It is to be understood, however, that these examples are for illustrative purposes only and are not intended to limit the scope of the present invention.

Example 1: Preparation and Selection of Anti-TM4SF5 Antibody

Example 1-1: Panning by Phage Display

Figure 1C:
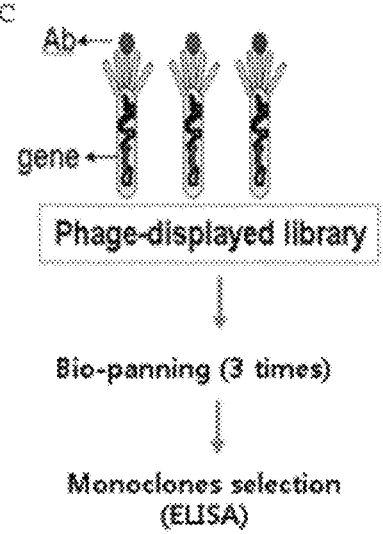
FIG. 1C shows a flow chart illustrating the antibody screening process of the present invention.

A TM4SF5 antigen protein including the amino acid region spanning from the $113^{th}$ to $157^{th}$ residues of TM4SF5 extracellular domain 2 (TM4SF5 EC2) was constructed. The C-terminus of the TM4SF5 EC2 protein was fused to a Myc protein and a human Fc protein to construct a fusion protein construct in the form of TM4SF5 EC2-hFc-Myc. The fusion protein including the TM4SF5 EC2 domain, AA 113-157, was expressed in HEK293E cells using the vector system for high expression of proteins in mammalian cells (KR Pat No. 10-110365), possessed by the present inventors, and purified. The overall screening process for the antigen proteins and antibodies used in the present invention is illustrated in FIGS. 1A and 1C. The process for screening the antibody library for the antigen proteins via panning was performed as follows.

Cells from the mouse scFv library were inoculated into 100 mL of 2xYT to an absorbance of 0.1 at OD 600 nm, and cultured at 37° C. at 250 rpm until they had the OD value of from 0.5 to 0.7.

Then, a helper phage VCSM13 (Stratagene) was superinfected with a 10-fold number of cells of the library at 37° C. for 30 minutes, and cultured at 250 rpm for 30 minutes. The infected cells were centrifuged at 3500 rpm for 10 minutes, and amplified in 200 mL of a freshly prepared 2xYTAK medium (0.1% ampicillin and 0.1% 70 mg/mL kanamycin) at 26° C. at 250 rpm overnight. The resultant was centrifuged at 6000 rpm for 20 minutes, and the supernatant, in which the phage was dissolved, was added with 4% (w/v) polyethylene glycol (PEG) and 3% NaCl, and precipitated on ice for 1 hour. The resultant was centrifuged at 4° C. at 8,000 rpm for 1 hour, and the phage was dissolved in 1 mL of phosphate-buffer saline (PBS). The resultant was centrifuged at 4° C. at 13,000 rpm for 10 minutes and used.

The TM4SF5 EC2-hFc-Myc antigens and hFc fragments as a control group were diluted in sodium carbonate buffer (pH 9.6) at a concentration of 5 μg/mL, and immobilized on the surface of an Immuno-96 MicroWell plate (Nunc, Denmark) at 4° C. On the next day, the immobilized antigens were washed twice with 200 μL of PBS and blocked with 200 μL of a blocking buffer (4% skim milk in PBS, MPBS) at room temperature for 2 hours. The library phage prepared above was mixed with a blocking buffer at 1:1 ratio, allowed to react in the wells where the hFc fragments were immobilized for 30 minutes, and the phages bound to the hFc fragments were removed. The phages which went through the subtraction process were allowed to react in the wells where the TM4SF5 EC2-hFc-Myc antigens were immobilized, washed 5 times with 200 μL of PBST (0.05% tween 20) for 2 minutes, and twice with 200 μL of PBS and removed non-specifically bound phages. The phages bound to the antigens above were eluted with 100 μL of 0.2M glycine-HCl (0.1% BSA, pH 2.5) for 10 minutes, and then immediately neutralized with 6 μL of 2 M Tris-HCl (pH 8.0). The eluted phages were transferred to 5 mL of ER2738 (OD 600 nm, 0.7), infected at 37° C. for 30 minutes and cultured at 200 rpm for 30 minutes. The cells infected with the phages were centrifuged at 3,500 rpm for 10 minutes, dissolved in 600 μL of a medium, aliquoted in the amount of 300 μL, respectively, and cultured in SOB medium at 30° C. overnight. The resulting cells were recovered with 2 mL of 15% glycerol. The recovered cells were infected again with the phages and the panning was performed as described above.

Example 1-2: Phage-ELISA Screening

Figure 2:
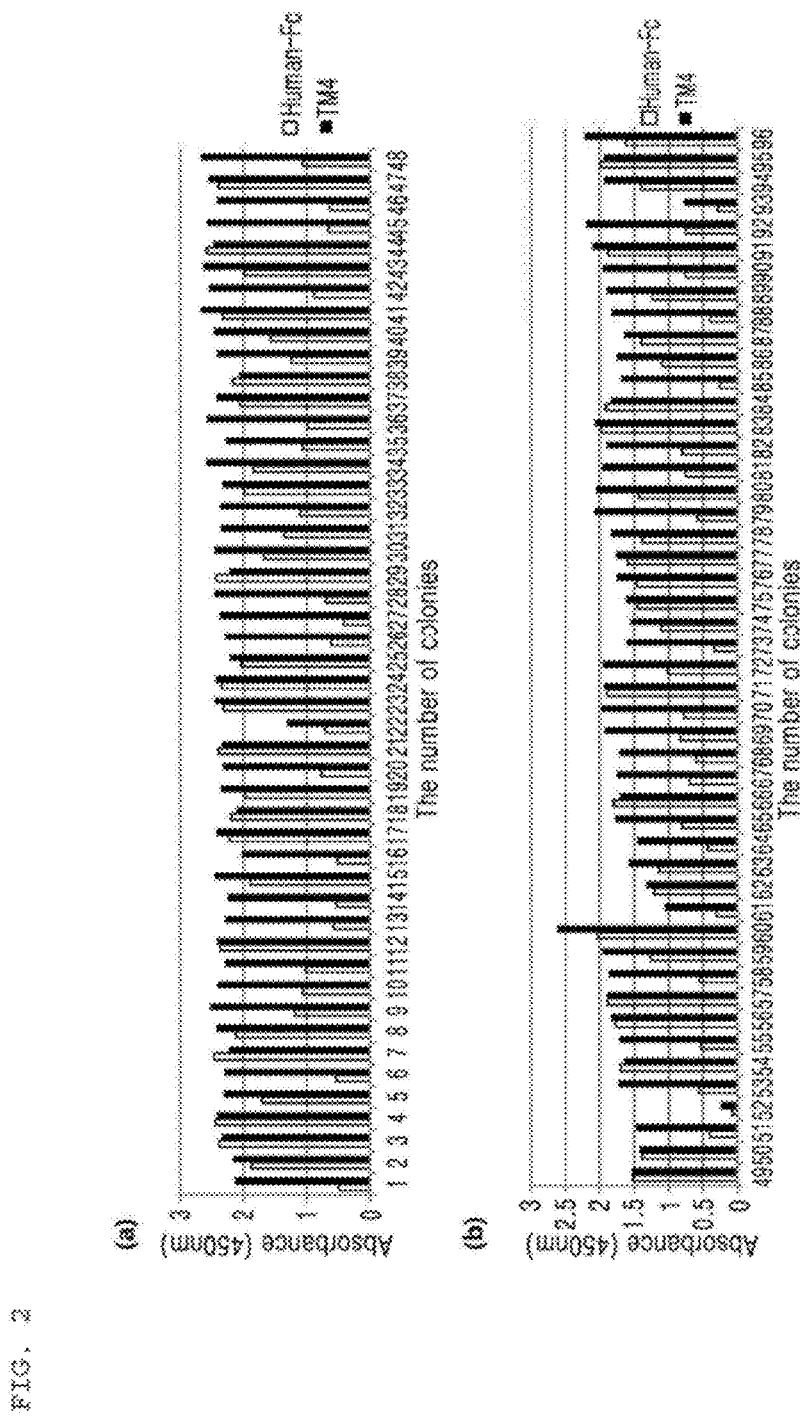
FIG. 2 shows the result of phage ELISA performed on the 96 clones panned from the HBX library, wherein, among them, 20 clones exhibited positive reactions to TM4SF5 EC2.

After the second panning, 96 colonies were randomly selected and cultured overnight on a deep well plate (Bioneer, Korea), where each well was loaded with 200 μL of 2xYTA medium. On the next day, 10 μL of the culture liquid was transferred into a new deep well plate added with 90 μL of a medium and cultured at 37° C. at 250 rpm for 6 hours. The resultant was added with 10 μL of the VCSM13 helper phage, superinfected at 37° C. for 30 minutes, and cultured at 250 rpm for 30 minutes. Then, the resultant was added with 100 μL of 2xYTAK medium (0.1% ampicillin and 0.2% kanamycin), and cultured at 26° C. at 250 rpm overnight. On the next day, the resultant was centrifuged at 2000 rpm for 10 minutes to obtain the phages. Meanwhile, in the Immuno-96 microwell plate, the hFc as a control group and the TM4SF5-EC2 antigens, which were immobilized on the surface of the plate at a concentration of 1 μg/mL in 100 μL of sodium carbonate buffer overnight, were washed twice with 200 μL of PBS, and reacted with 4% MPBST (skim milk in 0.05% PBST) at 37° C. for 1 hour. The phages were mixed with 4% MPBST at a 1:1 ratio for 30 minutes, and aliquoted in the amount of 100 μL to each of the blocked wells and allowed to react for 1 hour. To remove the non-specifically bound phages, the resultant was washed 4 times with 200 μL of PBST, and reacted with IgG-anti-M13-HRP (Pharmacia), which was diluted in 100 μL of 0.4% MPBST at a 1:2000 ratio, for 1 hour. The resultant was washed 5 times with 200 μL of PBST, and added with 100 μL of a TMB substrate reagent set (BD bioscience, USA), where substrates A and B were mixed at a 1:1 ratio, for color development. Then, the degree of color development was observed and the reaction was stopped by adding 50 μL of 2.5M $H_2SO_4$. The color development was measured at OD 450 nm by a microplate reader. Based on the results, 20 colonies of #1, #6, #13, #14, #16, #26, #27, #28, #45, #46, #51, #53, #55, #58, #68, #73, #79, #85, #88 and #92, which showed positive responses among the 96 colonies, were selected (FIG. 2).

Example 1-3: Sequence Analysis of Screened Clones

Figure 3:
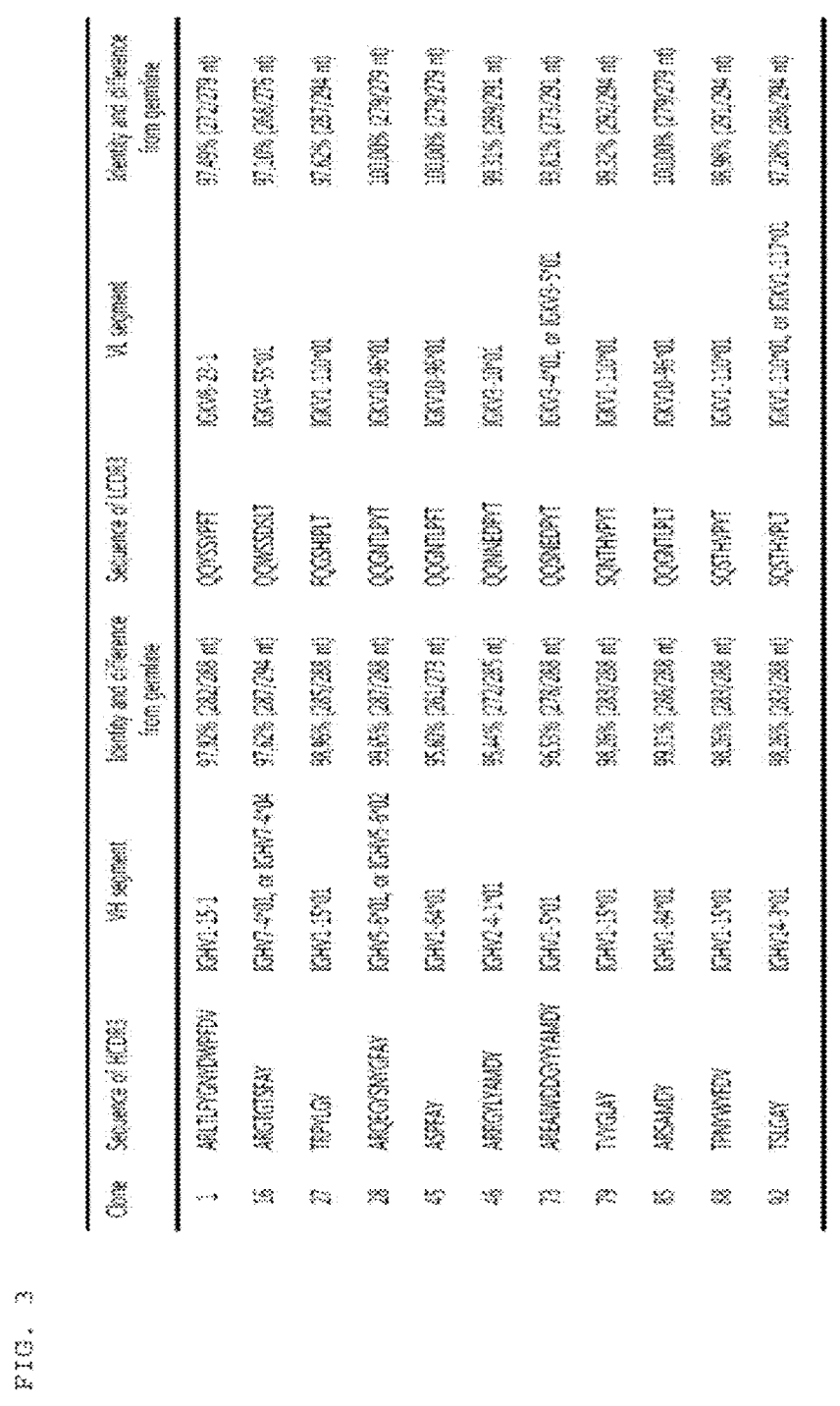
Figure 4:
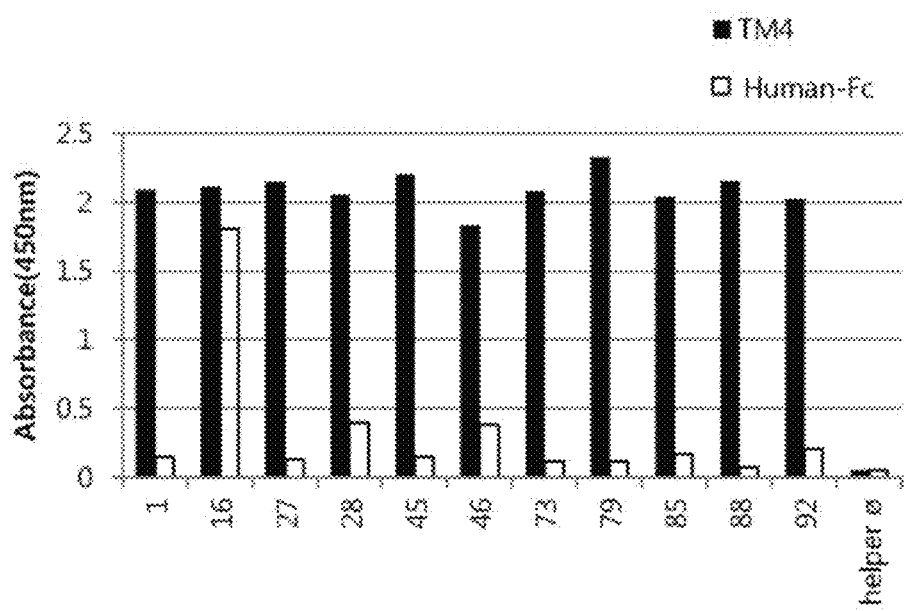
FIG. 4 shows the results of ELISA performed on the clones #1, #16, #27, #28, #45, #46, #73, #79, #85, #88 and #92 having mutually different sequences.
Figure 5E:
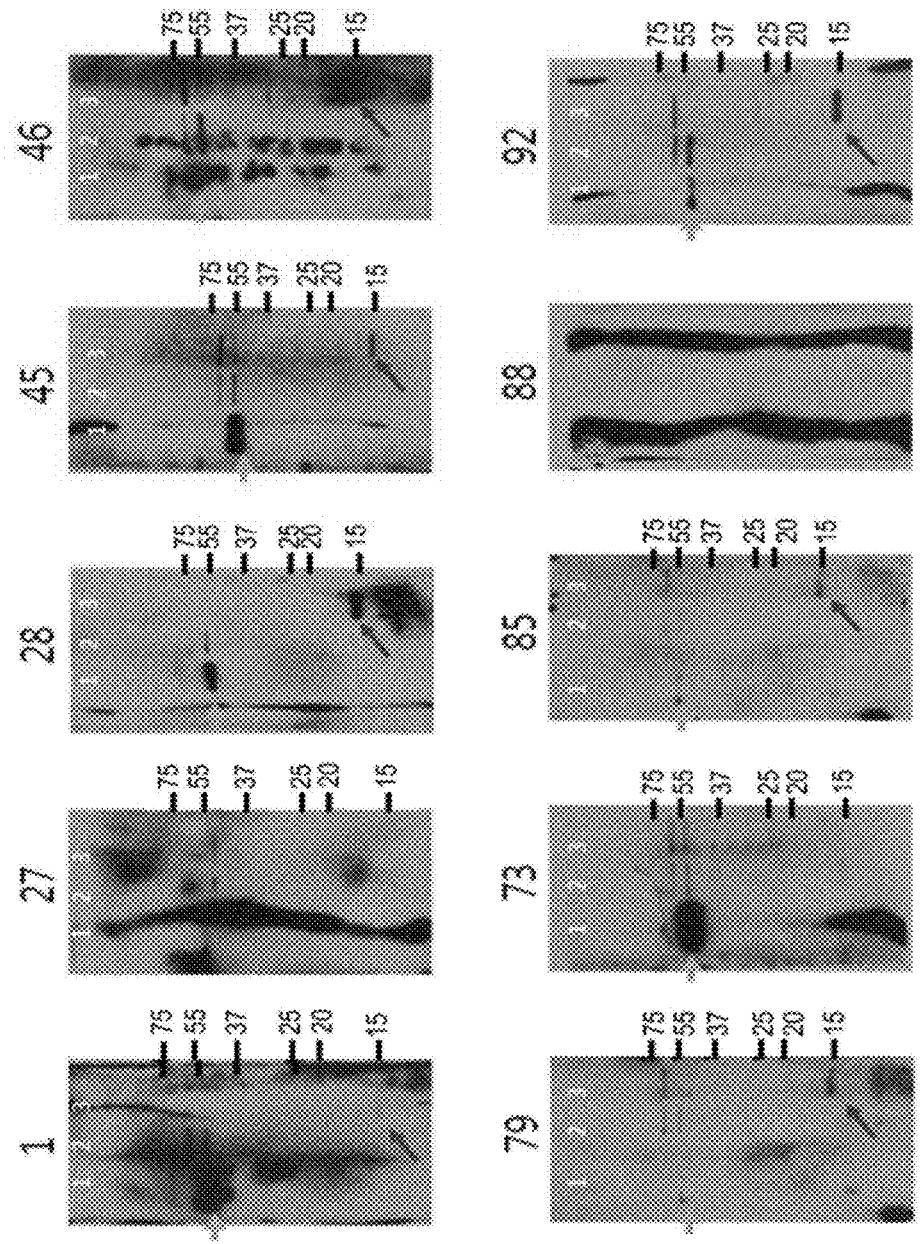

Upon analyses of the 20 colonies selected via phage-ELISA screening of Example 1-2 regarding their sequences and the sequences of their CDR3 regions, colonies #1 and #6 were confirmed to have the same sequence, and colonies #13, #14, #26, #51, #53, #55, #58, #68, and #73 were confirmed to have the same sequence. Based on the analyses, 11 different sequences were separated (FIG. 3). Among the colonies having the same sequence, colonies #1 and #73 were assigned as representative colonies, and the remaining 11 colonies with mutually different amino acid sequences were subjected to ELISA regarding the scFv, where the human-His-Fc-Myc was bound (FIG. 4), and the colony #16 showed a positive response to the control group, and thus colonies #1, #27, #28, #45, #46, #73, #79, #85, #88 and #92 were selected excluding the colony #16.

Of them, the selected monoclonal antibody #1 included an amino acid sequence for a heavy chain variable region represented by SEQ ID NO: 1, and an amino acid sequence for a light chain variable region represented by SEQ ID NO: 5; a polynucleotide sequence encoding for a heavy chain variable region represented by SEQ ID NO: 9, and a polynucleotide sequence encoding for a light chain variable region represented by SEQ ID NO: 10.

Additionally, the selected monoclonal antibody #27 included an amino acid sequence for a heavy chain variable region represented by SEQ ID NO: 11, and an amino acid sequence for a light chain variable region represented by SEQ ID NO: 13; a polynucleotide sequence encoding for a heavy chain variable region represented by SEQ ID NO: 17, and a polynucleotide sequence encoding for a light chain variable region represented by SEQ ID NO: 18.

Additionally, the selected monoclonal antibody #79 included an amino acid sequence for a heavy chain variable region represented by SEQ ID NO: 19, and an amino acid sequence for a light chain variable region represented by SEQ ID NO: 21; a polynucleotide sequence encoding for a heavy chain variable region represented by SEQ ID NO: 23, and a polynucleotide sequence encoding for a light chain variable region represented by SEQ ID NO: 24.

Additionally, the selected monoclonal antibody #88 included an amino acid sequence for a heavy chain variable region represented by SEQ ID NO: 25, and an amino acid sequence for a light chain variable region represented by SEQ ID NO: 27; a polynucleotide sequence encoding for a heavy chain variable region represented by SEQ ID NO: 29, and a polynucleotide sequence encoding for a light chain variable region represented by SEQ ID NO: 30.

Lastly, the selected monoclonal antibody #92 included an amino acid sequence for a heavy chain variable region represented by SEQ ID NO: 31, and an amino acid sequence for a light chain variable region represented by SEQ ID NO: 35; a polynucleotide sequence encoding for a heavy chain variable region represented by SEQ ID NO: 38, and a polynucleotide sequence encoding for a light chain variable region represented by SEQ ID NO: 39.

Example 1-4: Confirmation of the Binding Affinity of Anti-TM4SF5 Antibody to TM4SF5 and Selection The 10 different kinds of antibodies prepared in Example 1-3 were obtained from bacteria in the state of scFv-phage, and the lysates of liver cancer cells were subjected to western blot analysis, and the results are shown in FIG. 5C.

As a result, a total of 7 antibodies of #1, #28, #45, #46, #79, #85 and #92 were shown to have binding affinities to TM4SF5.

Additionally, the 10 different kinds of antibodies were converted into the scFv-Fc form and expressed in animal cells. In particular, the antibodies secreted extracellularly were collected in the state of a supernatant, and FACS analysis was performed to confirm the binding avidities of the antibodies in liver cancer cell lines.

The FACS analysis revealed that the monoclonal antibodies #1, #27, #79, #88 and #92 had relatively higher binding avidities to the TM4SF5 expressing cell line (Tp) than to that of the control cell line (Cp) (FIGS. 5A and 5B).

Based on the FACS analysis and western blot analysis, the monoclonal antibodies #1, #27, #79, #88 and #92 were selected again.

Figure 6:
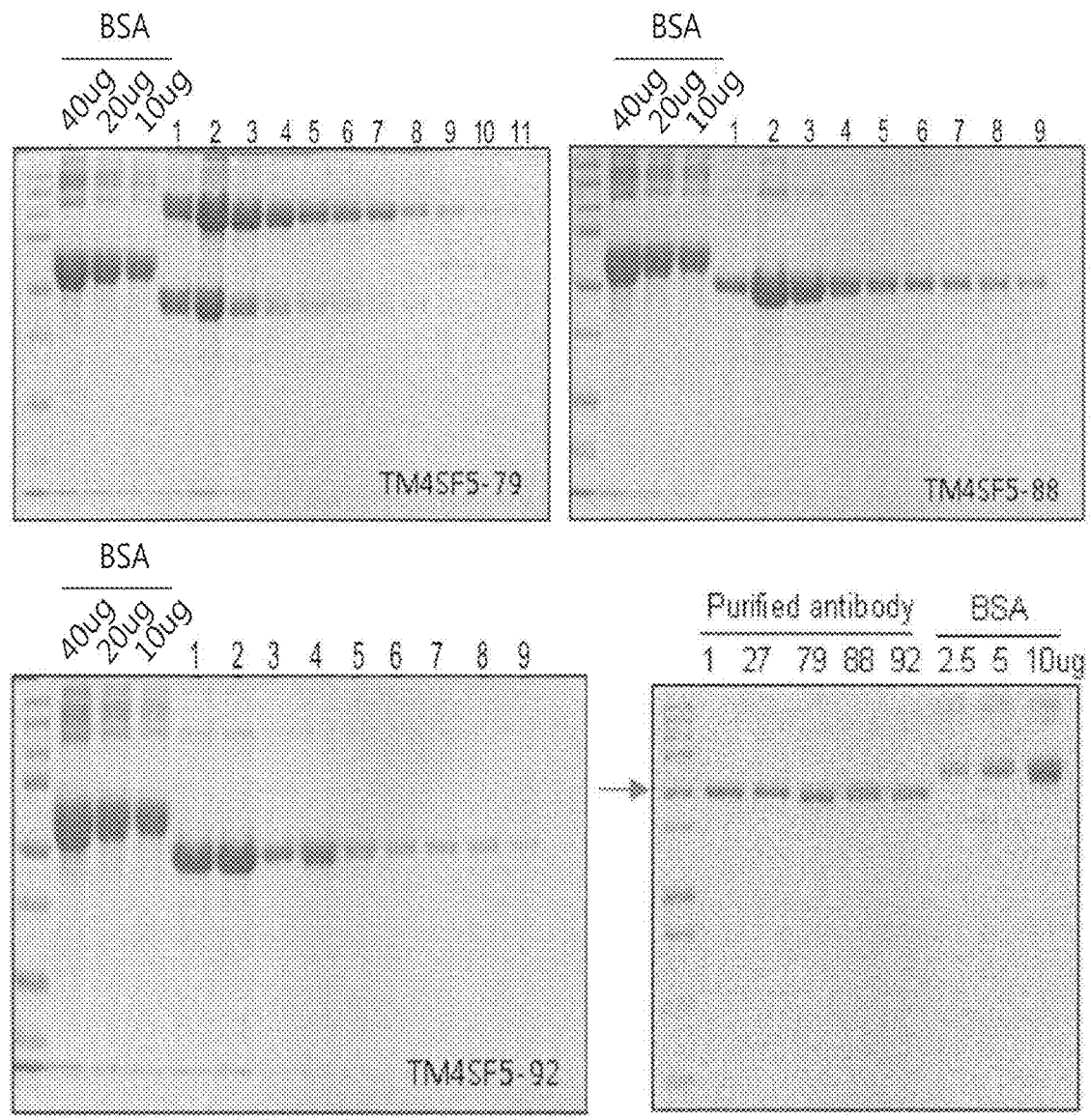
FIG. 6 shows the results of purification of the five kinds of antibodies (#1, #27, #79, #88, and #92) of the present invention by affinity chromatography, including the results of the antibodies #79, #88 and #92 obtained by affinity chromatography and the result of the five kinds of antibodies confirmed by gel electrophoresis after quantification.

Example 1-5: Production of Selected Anti-TM4SF5 Antibodies and Purification Thereof The five different antibodies #1, #27, #79, #88, and #92 selected from Example 1-4 were expressed in large scale in HEK293E cells and then purified. Specifically, the 2×10e7 of HEK293E cells (100 mm dish, 10 dishes) were transfected with an expression vector containing the polynucleotide encoding the antibodies, replaced with a serum-free medium, and supernatants were obtained 5 times at 3 day intervals. Then, the collected supernatants were purified with protein A excellose bead, and mean 2 mg each was obtained from each antibody (FIG. 6).

Example 2: Analysis of Binding Affinity of Anti-TM4SF5 Antibody

Figure 7:
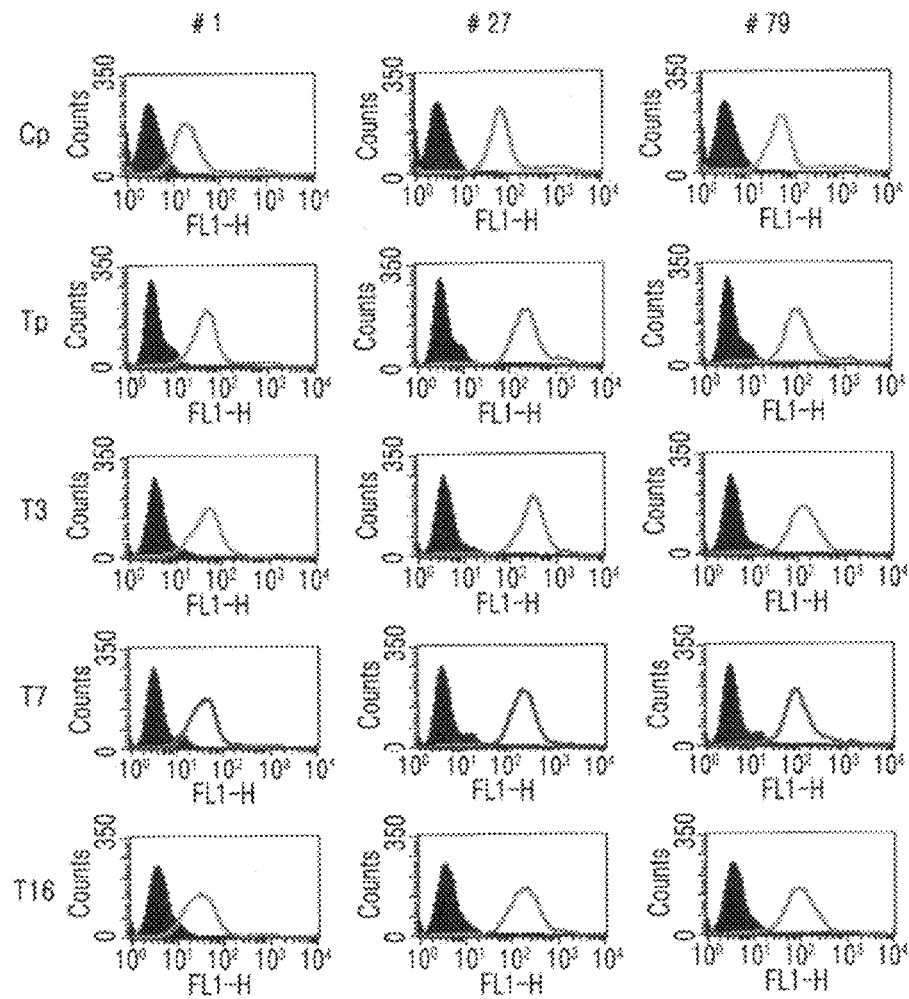
FIG. 7 shows the results of the antigen binding affinities of the anti-TM4SF5 antibodies (#1, #27 and #79) of the present invention for the control cell line (Cp), TM4SF5-overexpressing cell line (Tp), T3, T7 and T16 analyzed via FACS.
Figure 8B:
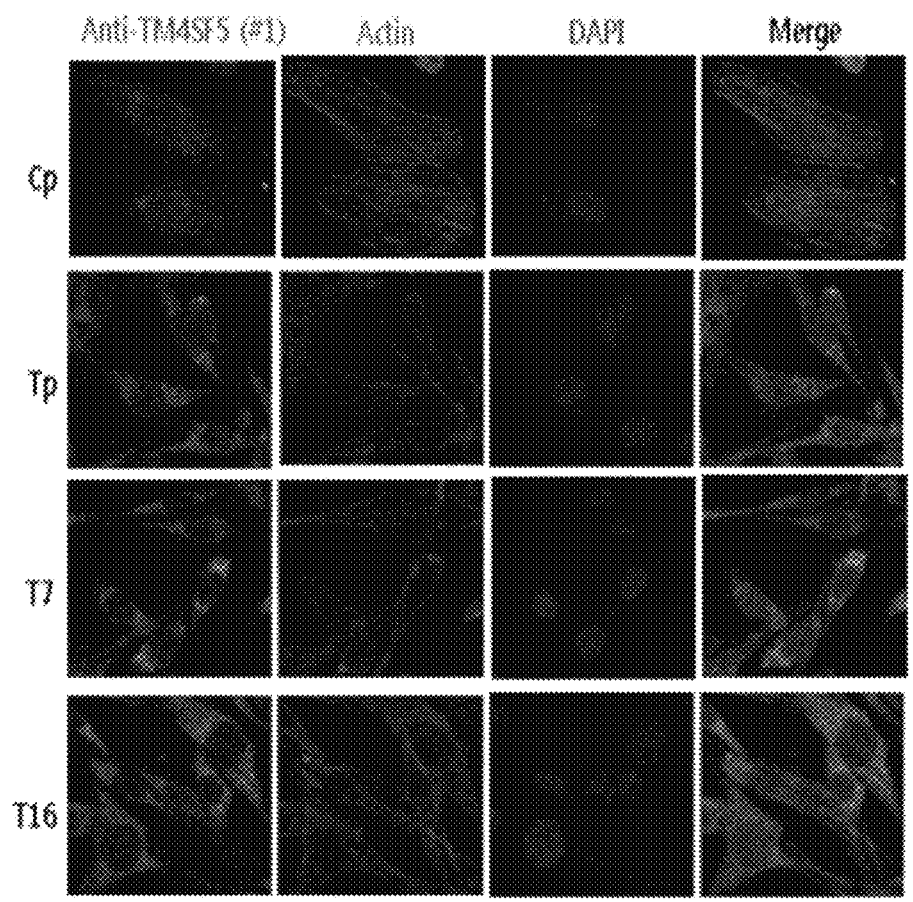
Figure 8F:
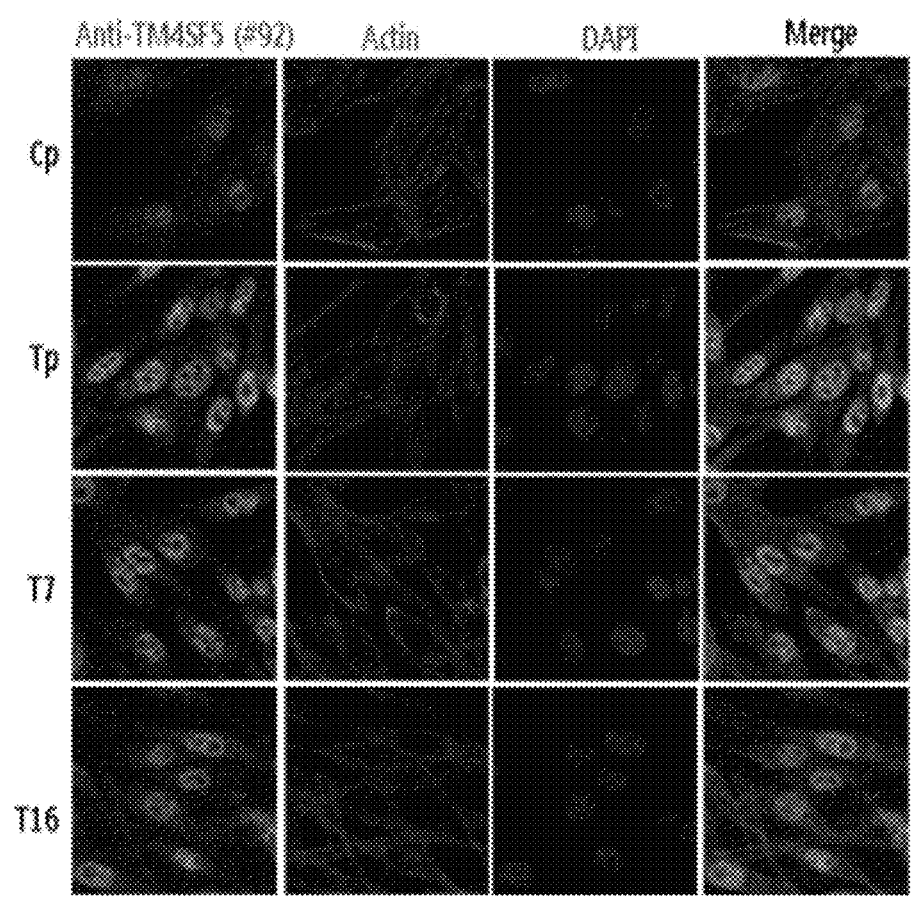

FACS experiments were performed for the TM4SF5-overexpressing SNU-449 liver cancer cell line (Tp, T3, T7, T16) and the control cell line (Cp). As a result, it was confirmed that the antibodies #1, #27 and #79 of the present invention distinctively bind to the TM4SF5-overexpressing cell line than to the control cell line (FIG. 7).

Additionally, the result of immunocytochemical experiments revealed that all the groups treated with the five kinds of antibodies of #1, #27, #79, #88 and #92 stained the TM4SF5-overexpressed liver cancer cells more distinctively than the control cells (FIGS. 8A to 8F). In particular, the group treated with the antibody #92 showed a peculiar pattern which did not appear in any of the other four antibodies, by which the nuclear membranes were stained, thus suggesting the possibility of the movement of TM4SF5 into nuclear membranes.

Figure 9:
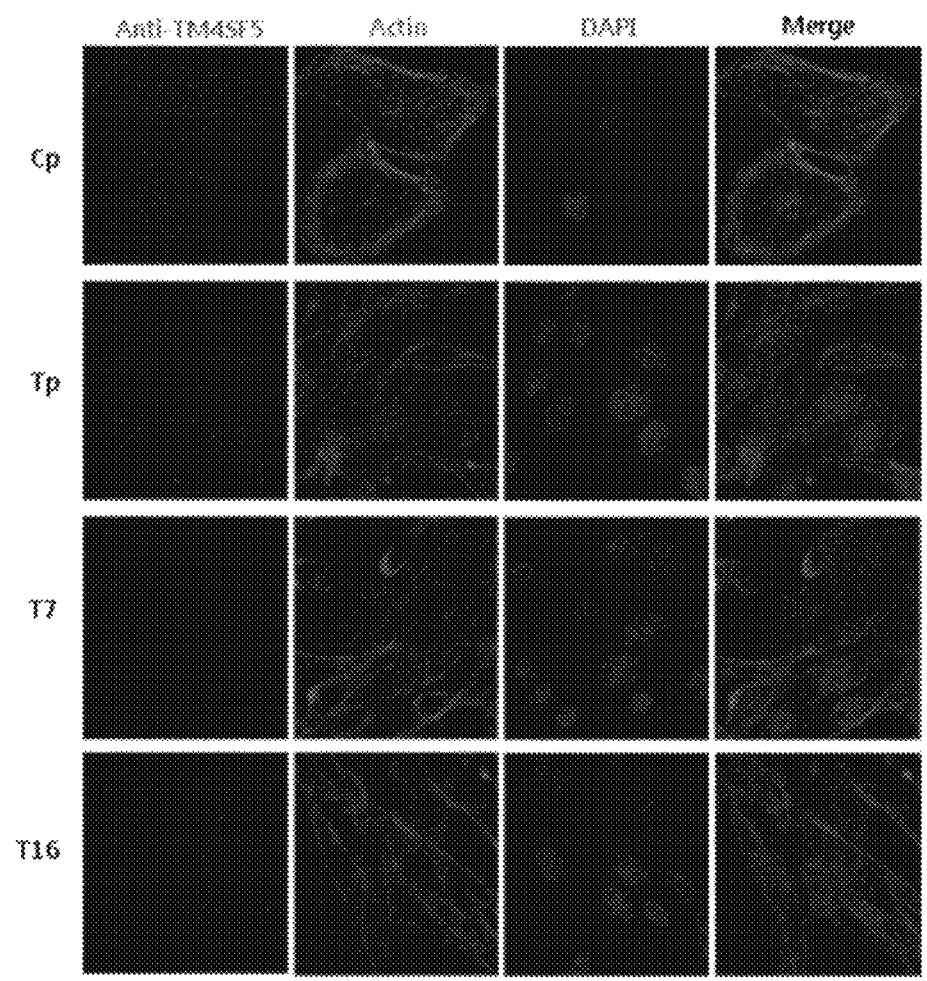
FIG. 9 shows the results of immunocytochemical analysis using the commercially available anti-human TM4SF5 polyclonal antibodies (Proteintech group 18239-1-AP).

Meanwhile, commercially available anti-TM4SF5 rabbit polyclonal antibodies (Proteintech group, cat no. 18239-1-AP) failed to recognize TM4SF5 under the same experimental conditions for the antibodies of the present invention, thus confirming the superior binding affinity of the antibodies of the present invention for TM4SF5 (FIG. 9).

Figure 10A:
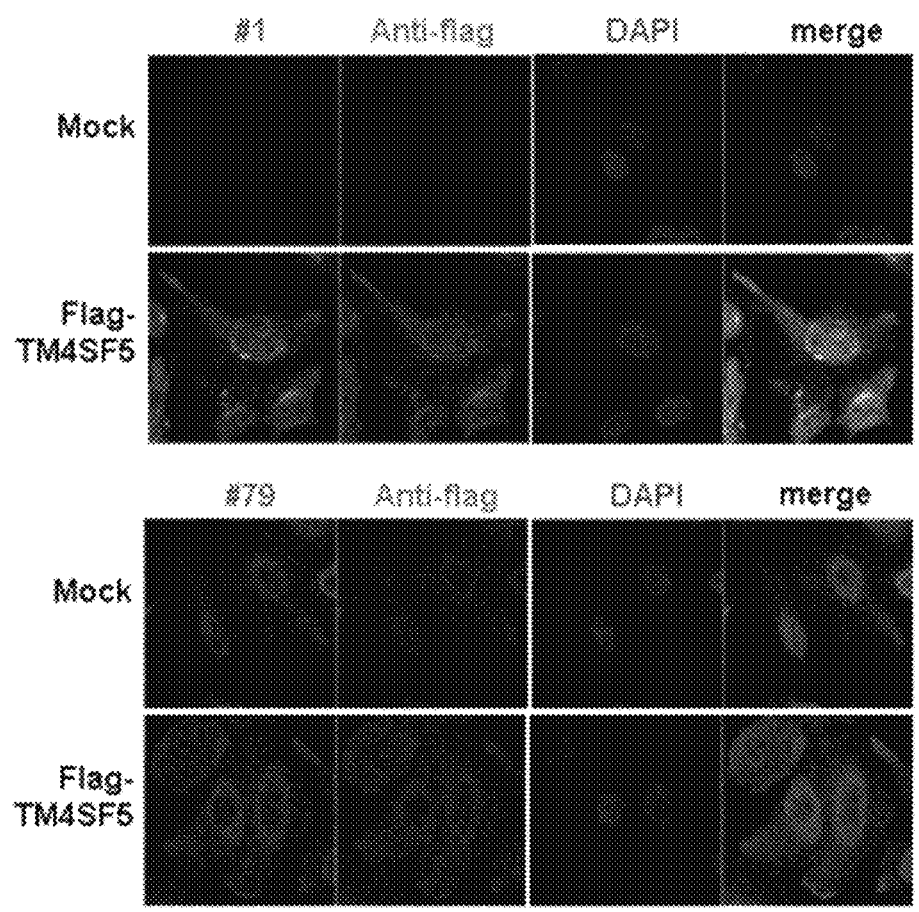

Additionally, when the Flag-tagged TM4SF5-overexpressing SNU-761 liver cancer cell line was co-stained with the anti-TM4SF5 antibodies of the present invention and anti-Flag antibodies it resulted in a co-localization (FIGS. 10A and 10B).

The results above indicate that the TM4SF5 antibodies of the present invention have superior activities capable of binding to TM4SF5. Furthermore, in the diagnosis of cancer cells, the strong binding affinities of the antibodies of the present invention indicate that they can bind with high sensitivity and specificity.

Example 3: Analysis of Target Inhibitory Effect of Anti-TM4SF5 Antibody

As it was reported that TM4SF5 promotes the proliferation of liver cancer cells and increases cell motility (J. Clin. Invest. (2008) 118:1354-1366; Carcinogenesis (2009) 30:1872-1879; J. Cell. Biochem. (2010) 111:59-66), the target inhibitory activities of anti-TM4SF5 antibodies #1, #27 and #79 of the present invention were analyzed via cell growth experiments, transwell assay, and wound healing assay.

(1) Transwell Assay

The effect of treatment with the antibodies of the present invention on cell invasion activity in a Tp cell, a TM4SF5-overexpressing liver cancer cell line, was analyzed. The TM4SF5-overexpressing liver cancer cell was pre-incubated with 20 μg/mL of the antibodies of the present invention, plated out in the transwell, and induced the movement of the cells for 48 hours. The migrated cells were then immobilized and stained with Crystal Violet, and the average value was obtained by counting under 200× magnification. As a result, it was observed that the treatment with the anti-TM4SF5 antibodies of the present invention inhibited the invasion of the TM4SF5-overexpressing liver cancer cells. Specifically, the antibodies #1, #27 and #79 of the present invention inhibited the invasion of the liver cancer cells by 83%, 56% and 49%, respectively (FIG. 11A), whereas the antibodies #88 and #92 of the present invention inhibited the infiltration by 73% and 46%, respectively (FIG. 11B).

Additionally, the effect of the antibody #1, a representative antibody of the present invention, on the decrease in cell migration using the Huh7 liver cancer cells was examined.

Specifically, 1×10e4 cells were pre-incubated with 30 μg/mL of the antibody and aliquoted into an insert. After adding 5% FBS to the lower chamber of the insert and incubating for 48 hours, the migrated cells were immobilized and stained. The number of cells observed under 200× high power field (HPF) view was counted to obtain the average value, and the result is shown in FIG. 12.

Figure 12:
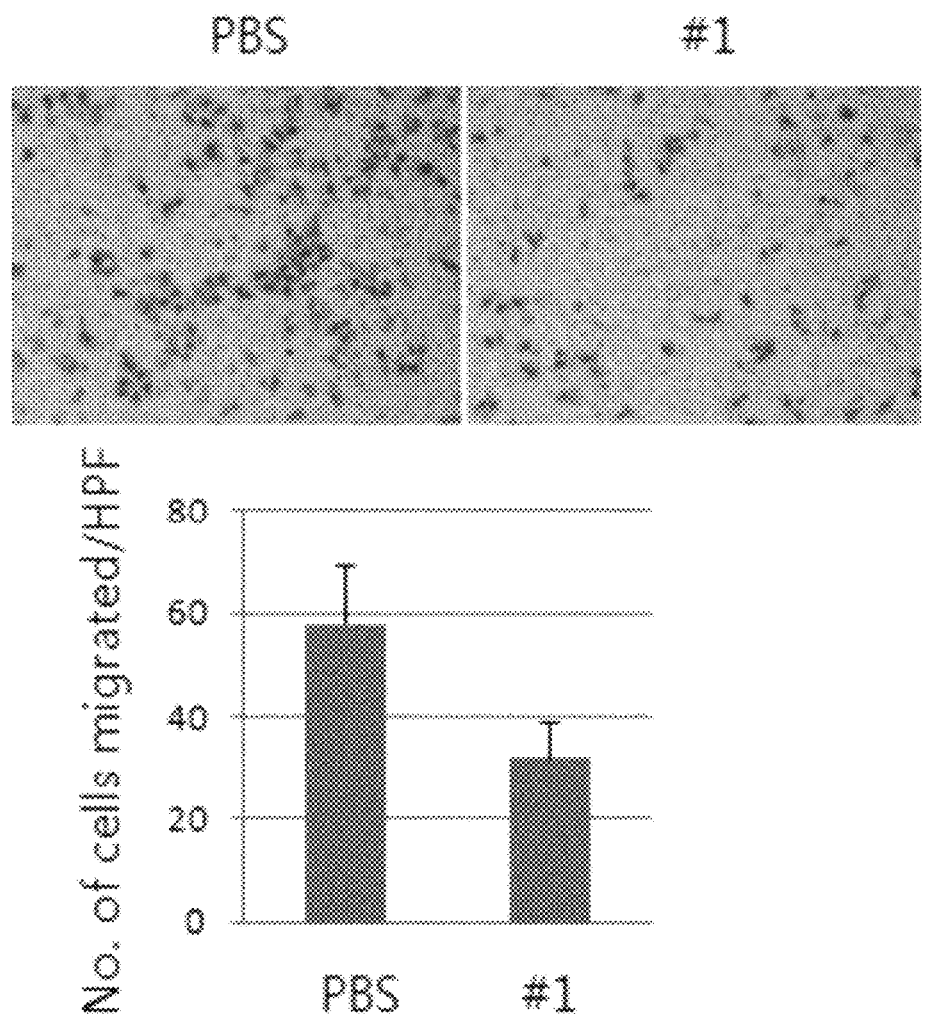
FIG. 12 shows the results of change in migration of Huh7 liver cancer cells by anti-TM4SF5 antibody #1, the representative anti-TM4SF5 antibody of the present invention.

As a result, as illustrated in FIG. 12, it was observed that the migration of the Huh7 cells, which intrinsically express the TM4SF5 protein, was decreased by about 45% by the treatment of the antibody #1, the representative antibody of the present invention.

(2) Wound Healing Assay

The effect of the anti-TM4SF5 antibodies on the migration of liver cancer cells was analyzed via wound healing assay. T16 cells, TM4SF5-overexpressing liver cancer cells, were plated out in a 96-well plate in a confluent state, scratched and then treated with the antibodies (20 μg/mL). Then, the degree of wound healing of the cancer cells were measured up to 48 hours. As a result, it was observed that the antibodies #1, #27, #79, #88 and #92 of the present invention showed an effect of decreasing wound healing (FIGS. 13A and 13B).

(3) Experiment of the Effect on Cell Growth

Additionally, the effect of the antibodies of the present invention on cell growth was confirmed. After plating out the Tp and T16 cell lines, TM4SF5-overexpressing liver cancer cell lines, on a 96-well plate, treated with the antibodies at a concentration of 20 μg/mL for 48 hours and 72 hours, respectively, and the degree of cell growth was measured based on colorimetric determination. The result revealed that the antibodies of the present invention did not show a distinctive inhibition of cell growth of liver cancer cell line in the presence of serum. However, the antibodies #1 and #79 of the present invention inhibited cell growth by about from 30% to 50% (FIG. 14A), and the antibodies #88 and #92 of the present invention inhibited cell growth by about 50% I the absence of serum (FIG. 14B). From the above results, it was confirmed that the antibodies of the present invention have the activities of inhibiting the growth of liver cancer cells.

The above results indicate that the antibodies of the present invention can bind specifically to TM4SF5 and effectively inhibit the biological activities of TM4SF5 such as EMT, thereby effectively blocking the proliferation, migration, and metastasis of cancer, thus being effectively used for preventing or treating cancer.

Example 4: Tissue Staining Using Anti-TM4SF5 Antibodies

Additionally, it was reported that the expression of TM4SF5 was induced by TGF-β in hepatocytes thereby inducing liver fibrosis (FEBS J (2012) 279:625-635). Accordingly, TM4SF5 is considered as a major factor inducing liver fibrosis as a precursor step to the development of liver cancer.

The induction of TM4SF5 by TGF-β treatment in human Chang hepatocytes was confirmed via RT-PCR and western blot experiments. When TM4SF5 was induced in Chang cells as such, it was confirmed via FACS analysis that TM4SF5 was recognized by #27, and the result is shown in FIG. 15A.

As a result, as shown in FIG. 15A, the anti-TM4SF5 antibodies were shown to effectively recognize the endogenous TM4SF5 proteins.

The CCl$_4$-treated mouse, a liver fibrosis-induced animal model with a severe liver damage and fibrosis caused by the CCl$_4$-treatment, was stained with the antibody #27, a representative antibody of the present invention.

First, the induction of liver fibrosis by CCl4 treatment was confirmed via Masson's Trichrome Staining (FIG. 15B).

Then, mouse tissues (tissues with liver fibrosis induced by CCl$_4$-treatment) were prepared into a paraffin sample, sectioned to have a thickness of from 4 μm to 5 μm and fixed to slides, deparaffinized with xylene, and subjected to ethanol (100%>90%>80%>70%) dehydration. Then, the tissues were dipped into 1 mM citrate buffer solution (pH 6.0), boiled for 10 minutes, and the tissues fixed to the slides cooled down at room temperature were allowed to react with 3% H$_2$O$_2$ for 10 minutes (hydrogen peroxidase in methanol). Then, the resulting tissues were blocked with 6% normal horse serum for 30 minutes, and reacted with the antibody #27 as the primary antibody at a concentration of 3 μg/mL (in 1% normal horse serum) at 4° C. overnight. Then, the resulting tissues were washed with PBS, reacted with a secondary antibody at a 1:100 ratio at room temperature for 1 hour (secondary antibody: Rabbit Anti-Human IgF(Fc), Fluorescein Conjugated (pierce #31535, 1.5 mg/mL), washed with PBS, stained with DAPI, and mounted to observe the result.

As a result, it was confirmed that the mouse liver in the control group, not treated with CCl$_4$, was not stained with the antibody #27, whereas the region with fibrosis in the CCl$_4$-treated mouse liver (liver damage induced) was stained with the antibody #27 (FIG. 15C). That is, the antibody #27 was shown to recognize the TM4SF5 which was expressed due to the liver damage.

Example 5: Characterization of TM4SF5-Binding Antibodies #27 and #79

The liver cancer cell surface binding activity of TM4SF5-Specific antibodies #27 and #79 was analyzed.

Figure 16A:
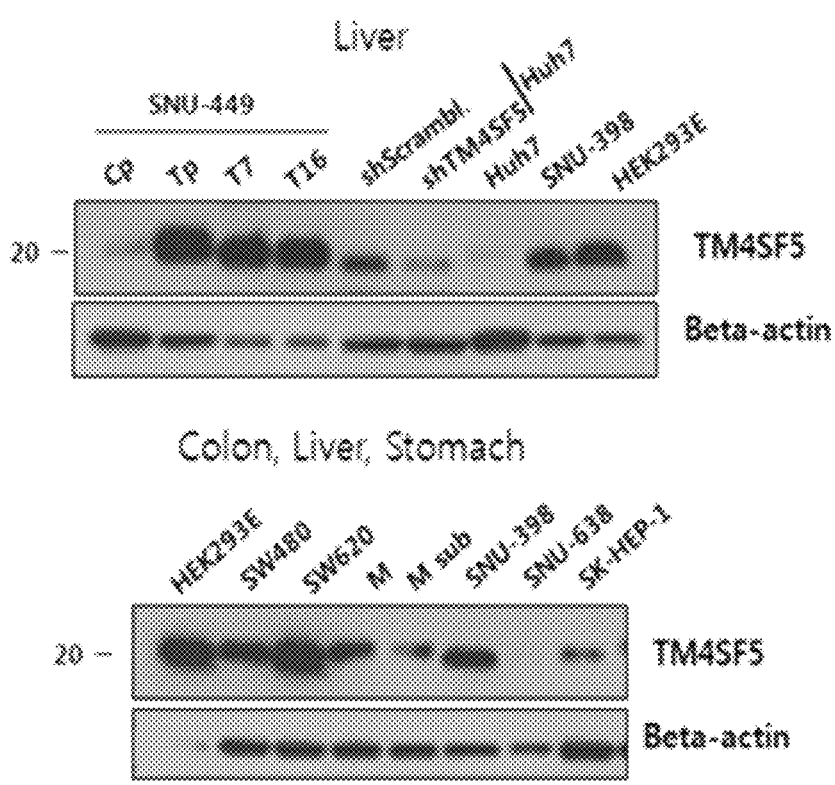

First, as a result of western blot analysis using rabbit polyclonal TM4SF5 antibody, TM4SF5 was shown to be expressed in various liver cancer cells and colorectal cancer cells (FIG. 16A).

Figure 16B:
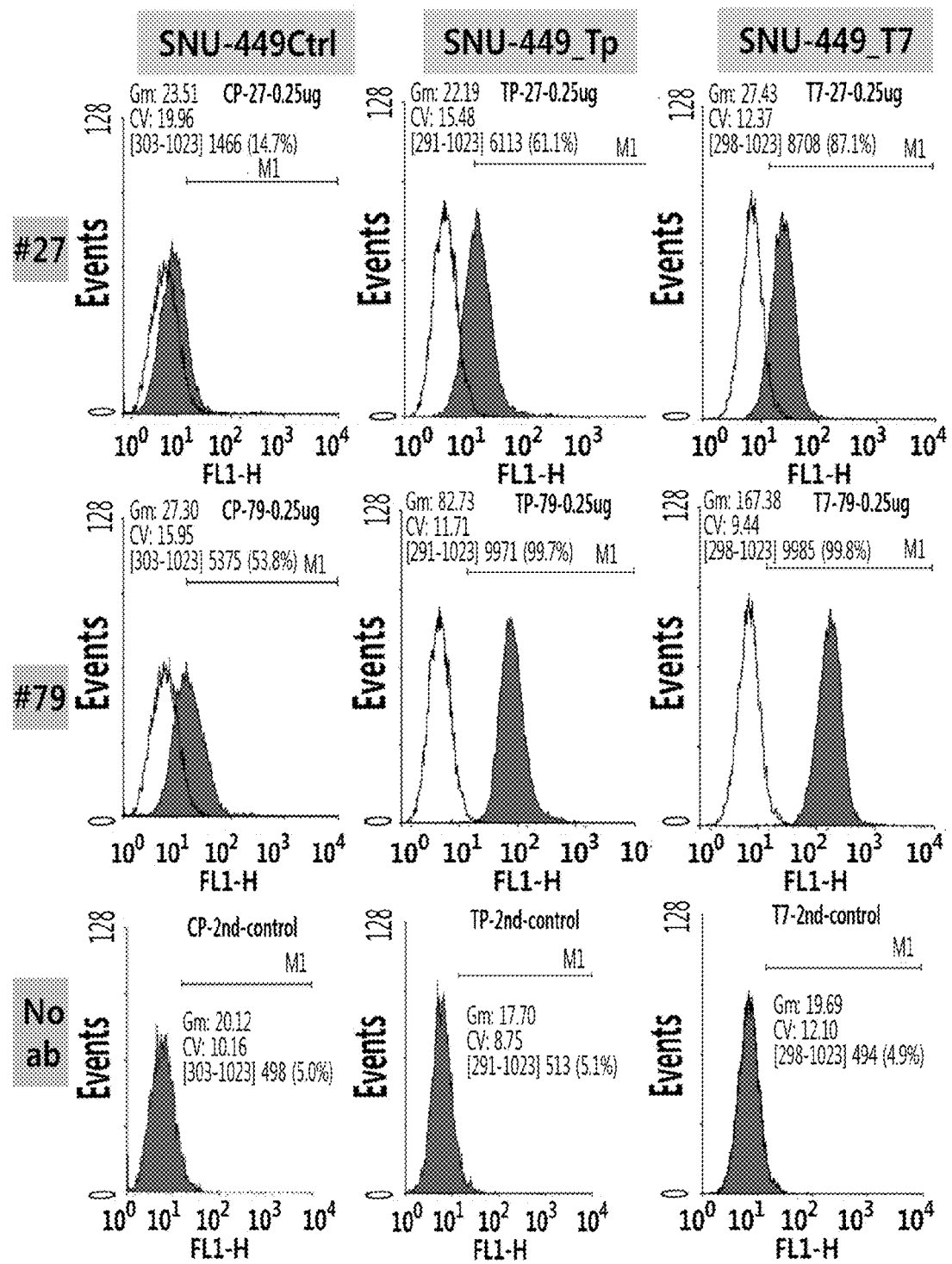
Figure 16C:
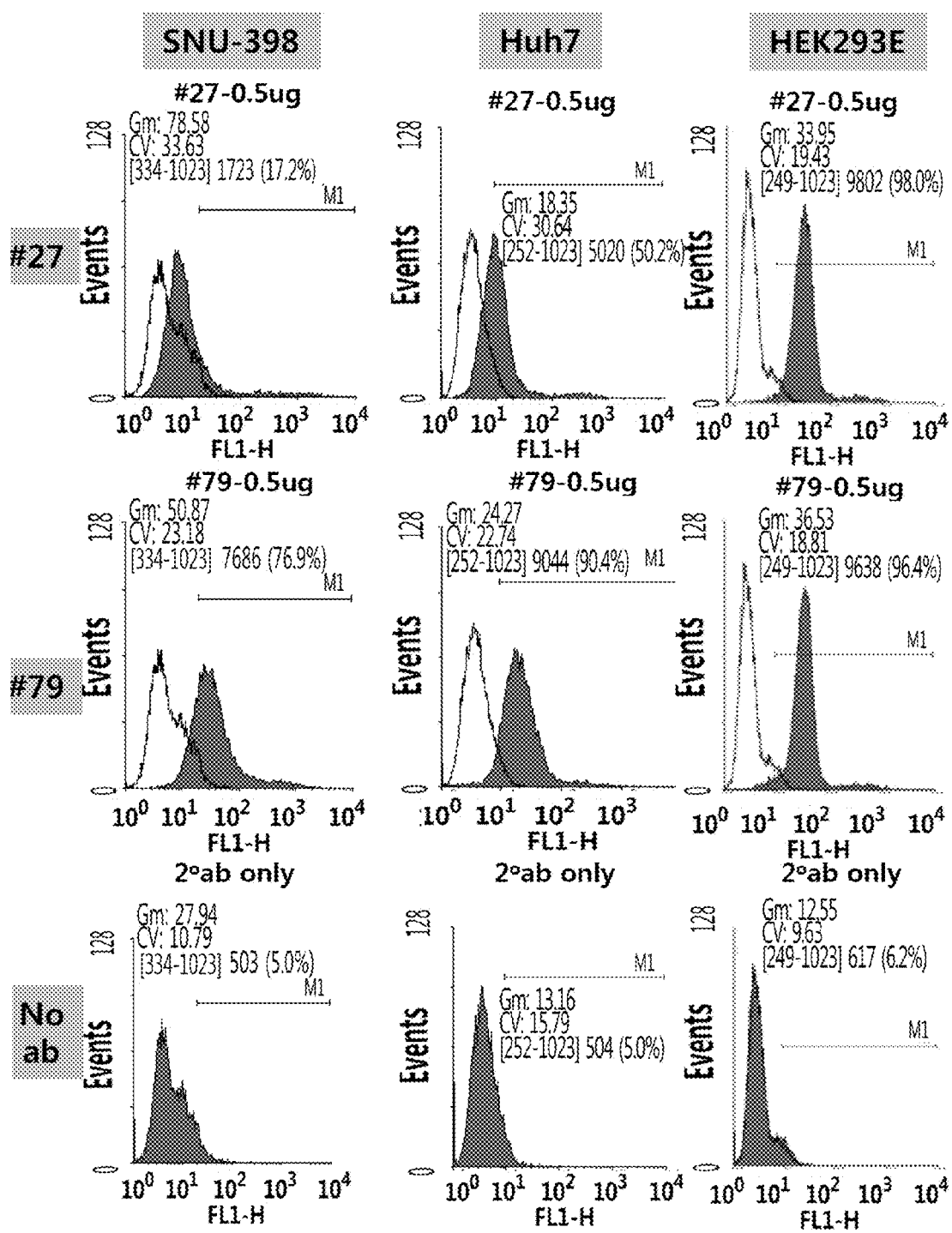

Additionally, the two different kinds antibodies were also shown to distinctively recognize TM4SF5 on the surfaces of various cancer cells (SNU-449Tp, SNU-449T7, Huh7, and SNU-398) and HEK293 cells via FACS analysis (FIGS. 16B and 16C).

Figure 16D:
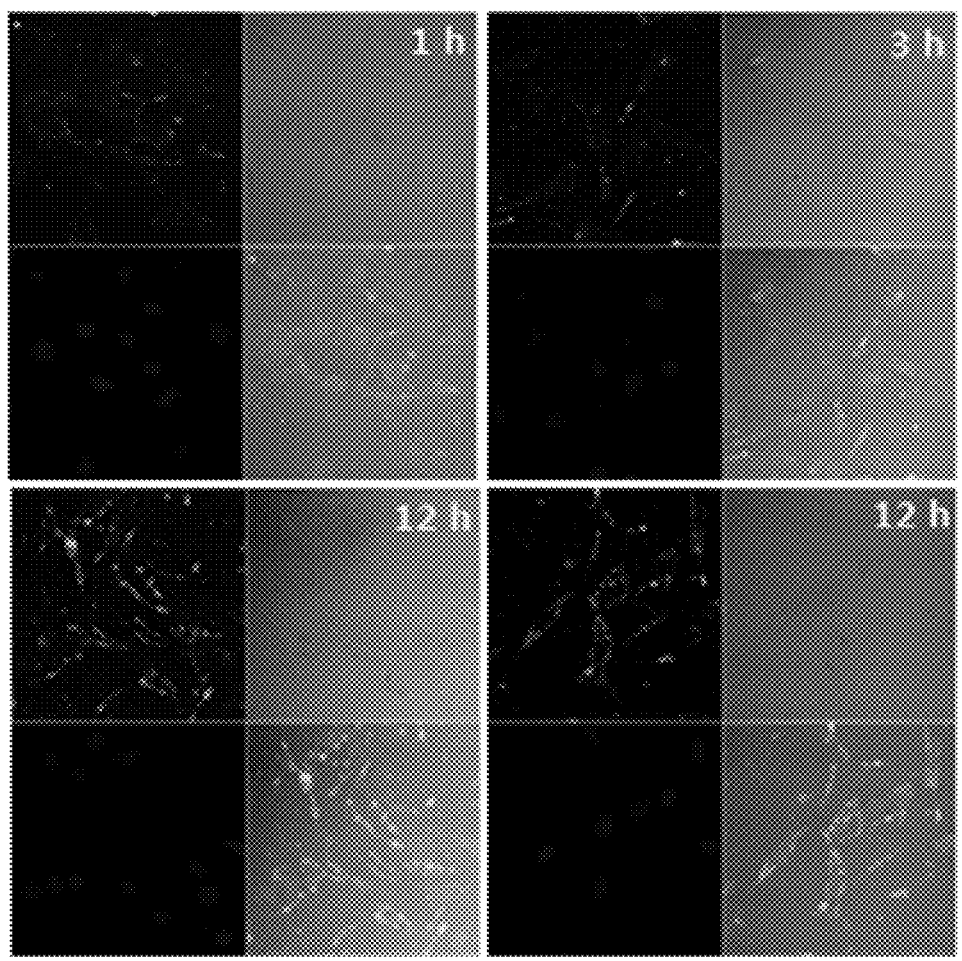

Additionally, the targeted TM4SF5 was shown to have a characteristic to be internalized through the antigen-antibody binding by antibody #27 via Internalization assay using immunocytochemistry (FIG. 16D).

Example 6: Neutralizing Effect of TM4SF5-Binding Antibodies #27 and #79

The target neutralizing effect/function-blocking effect of TM4SF5-specific antibodies #27 and #79 were analyzed.

First, the typical form of an antibody, where the linker between the heavy chain and the light chain is a single amino acid Alanine, forms the structure of a diabody. In the antibody format in the form of scFv-Fc to be used, a G4S linker (about 15 amino acids; (GGGGS)*3), which is a more general linker, appeared to be more suitable and thus the linker was modified to the G4S linker.

Figure 17A:
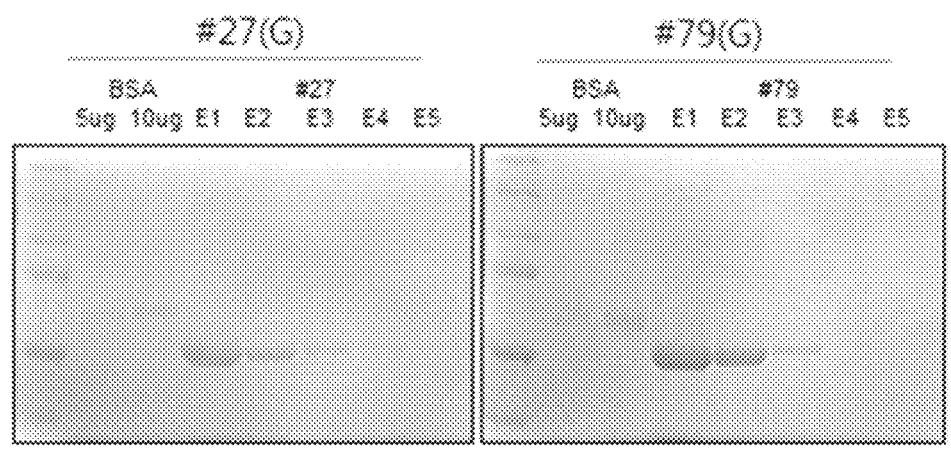
FIG. 17A shows the results of the expression/purification of #27(G) and #79(G), which are the linker-modified antibody forms of #27 and #79.

Specifically, after synthesizing the gene encoding the antibody, the gene was subcloned into an expression vector and transfected into HEK293E cells. Then, the transfected cells were cultured, and a conditioned medium was collected, and purified by protein A/G affinity column (FIG. 17A). From the above process, a total 1 mg of antibodies of #27 and #79 was obtained. The obtained antibodies #27 and #79 with modified linkers were assigned #27(G) and #79 (G), respectively.

Figure 17B:
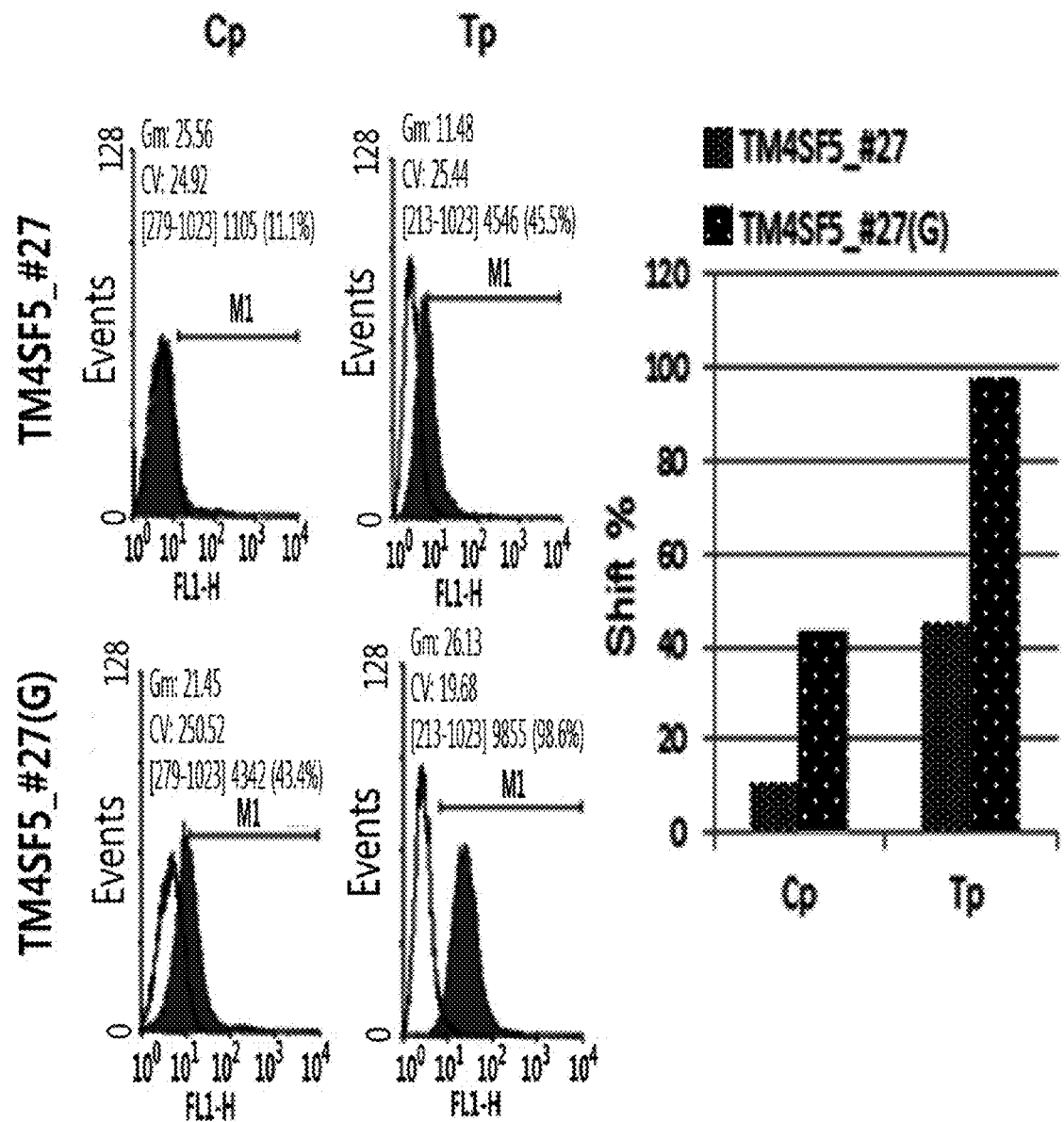
FIG. 17B shows the results of FACS analysis using antibody #27(G).

The results of FACS analysis on the TM4SF5-overexpressing liver cancer cell Tp and control cell Cp using the #27(G), it was confirmed that the binding capacity of the #27(G) was improved compared to that of the antibody #27 (FIG. 17B).

Then, the level of endogenous TM4SF5 proteins in various colorectal cell lines was analyzed via western blot and FACS using the #27(G) antibody.

Figure 17C:
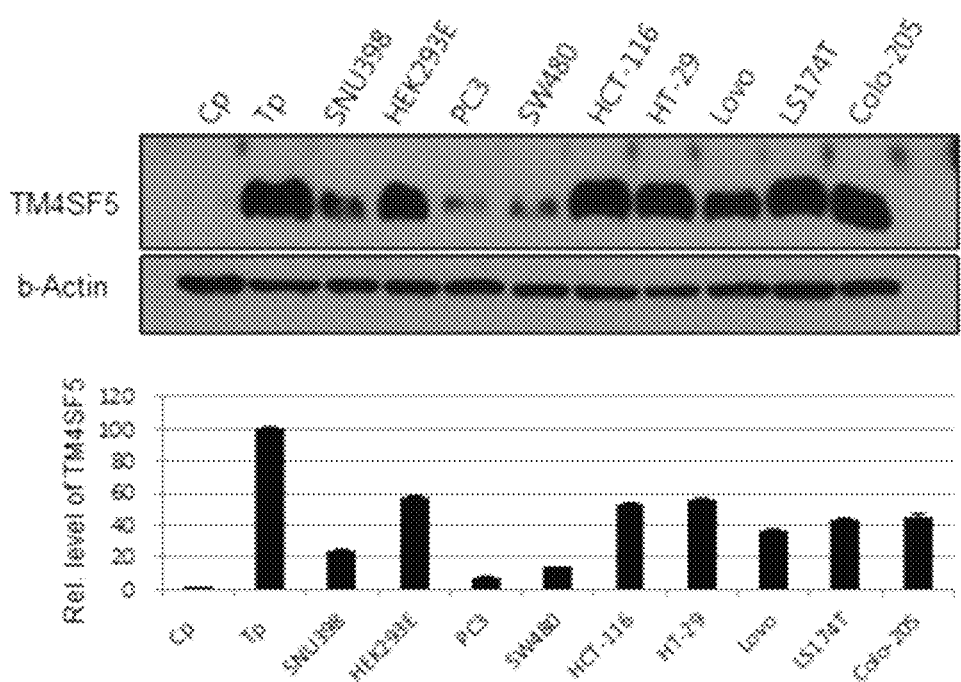
FIG. 17C shows the results of western blot analysis on the expression of endogenous TM4SF5 in various cancer cell lines using antibody #27(G).
Figure 17D:
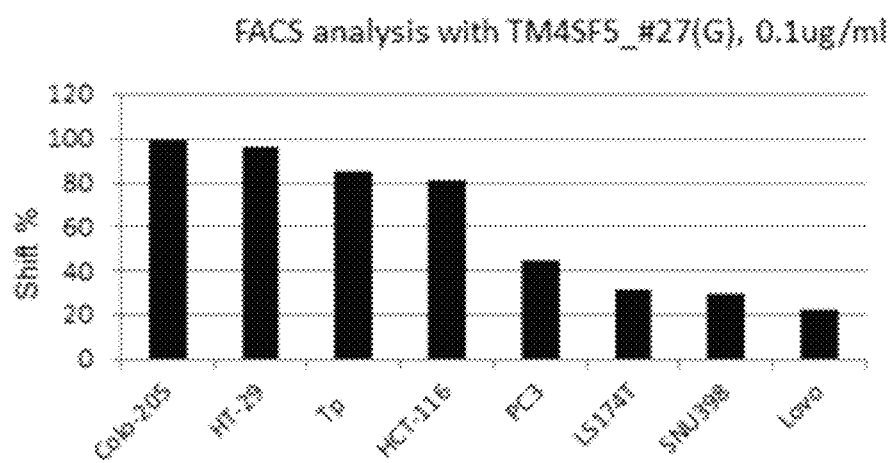
FIG. 17D shows the results of FACS analysis on the expression of TM4SF5 in various cell lines using antibody #27(G).

As a result, it was confirmed that the expression of TM4SF5 was higher in HCT116, HT29, LS174T, and Colo205 (colorectal cell lines) and relatively lower in Lovo, and SW480 (colorectal cell lines), and PC3 (prostate cancer cell line) (FIGS. 17C and 17D).

The function-blocking effects of the antibodies #27(G) and #79(G) were analyzed in the cancer cell lines, where the expression of TM4SF5 was confirmed, via proliferation assay and invasion/migration assay.

Figure 18A:
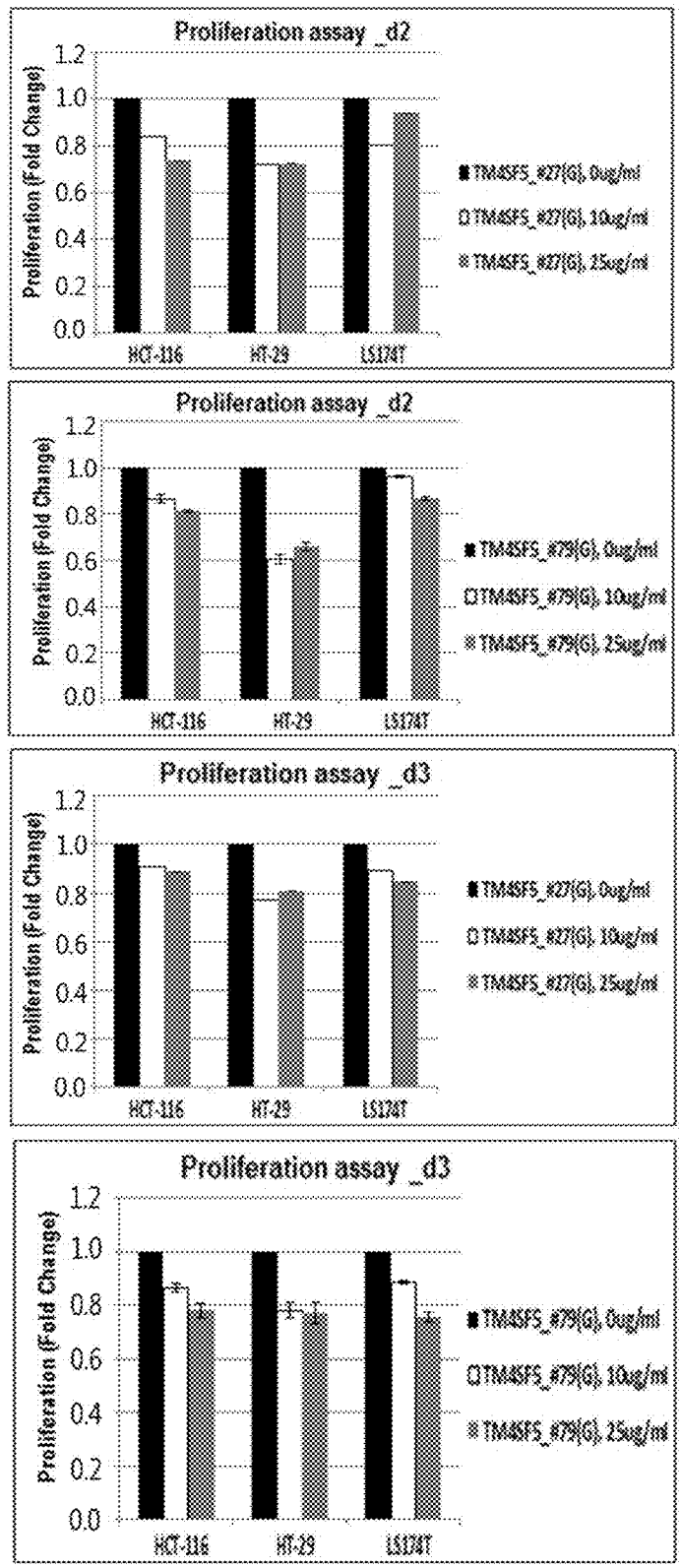

According to the results, HCT116, HT29, and LS174T cells showed a decrease in growth after treatment with the antibodies #27(G) and #79(G) at a concentration of 10 μg/mL or 25 μg/mL for from 48 hours to 72 hours (FIG. 18A), whereas the antibody treatment did not show any noticeable effect in the growth of PC3, SW480, Lovo, and Colo205 cells.

Figure 18B:
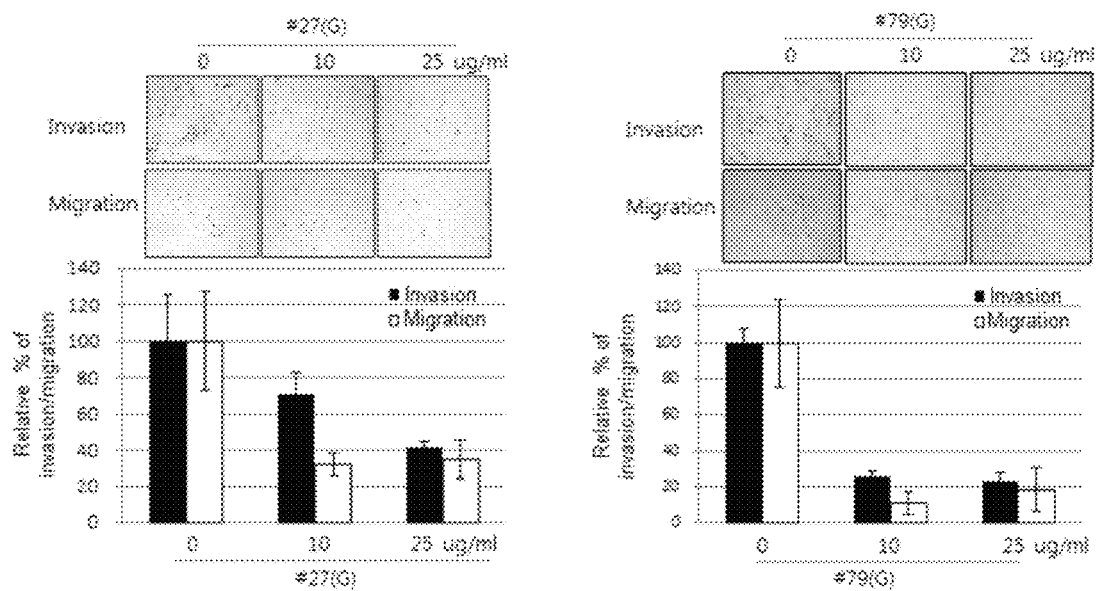
Figure 18C:
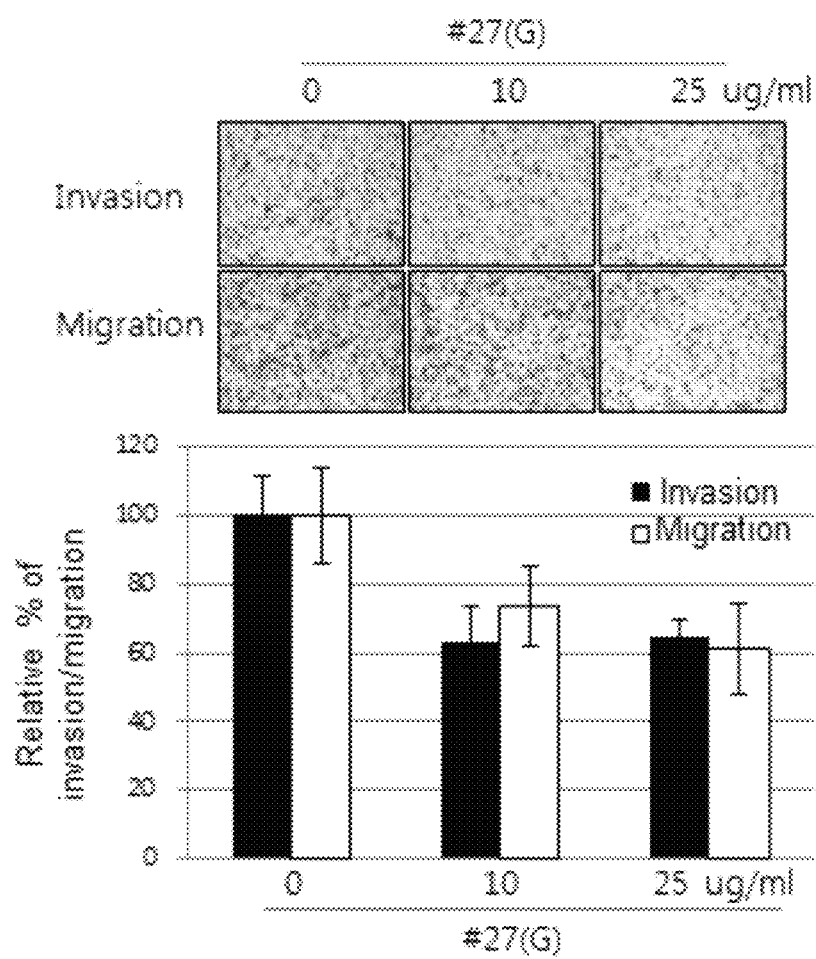

The result of a cell invasion/migration assay revealed that the HCT116 cells showed a 60% decrease in invasion and a 65% decrease in migration by the treatment with the antibody #27(G). The antibody #79(G) showed a similar effect (FIG. 18B). Additionally, the Colo205 cells showed a decrease of about 40% in the invasion and migration by the treatment with the antibody #27 (G) (FIG. 18C).

Example 7: Analysis of the Effects of TM4SF5-Specific Antibodies: ADCC-Inducing Effect by NK Cells The possible involvement of the antibodies #27(G) and #79(G) in the induction of the antibody-dependent cell-mediated cytotoxicity (ADCC) of cancer cells was analyzed.

ADCC is one of the representative anti-cancer effects being induced by therapeutic antibodies, and the principle of the anti-cancer effect includes binding of the therapeutic antibody to a target antigen on the surface of a cancer cell, recognizing of the binding by the effector cells (NK cells, macrophages, etc.) of an immune system, and subsequently lysing the target cancer cell by the activated effector cells.

In this Example, the possible involvement of the antibodies #27(G) and #79(G) in the lysis of TM4SF5-expressing cancer cells (target cells), which induced by the NK cells (effector cells) which express Fc receptor CD16 was analyzed via a colorimetric method.

Figure 19A:
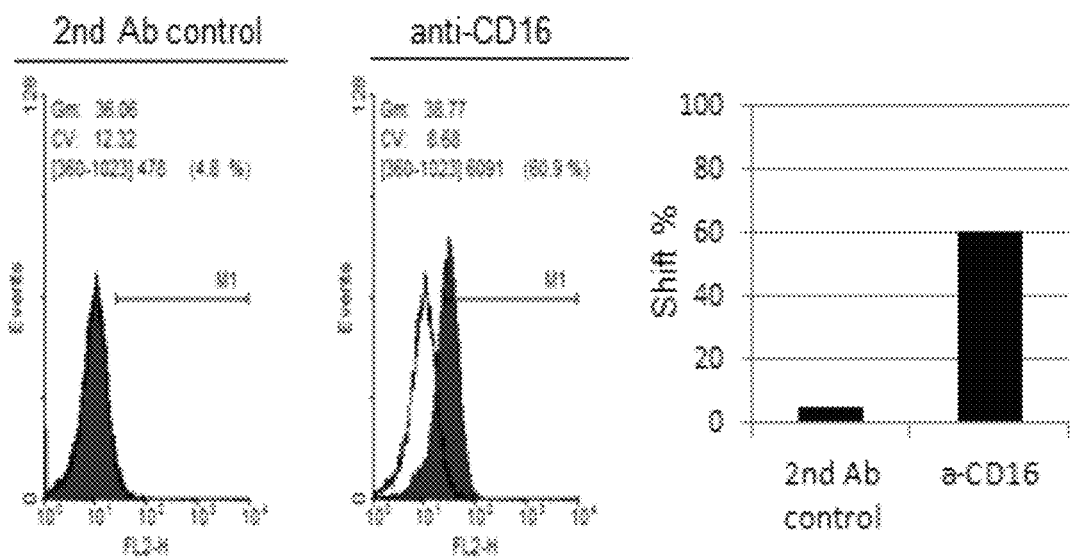

When the NK-92 cells (ATCC), where CD16 was retrovirally transduced, were cultured and analyzed via FACS method, it was confirmed that CD16 was apparently expressed (FIG. 19A).

Figure 19B:
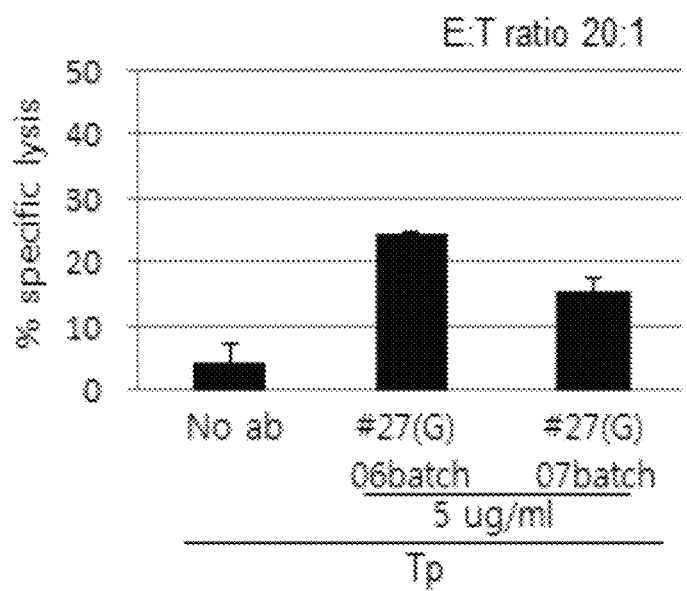
Figure 19C:
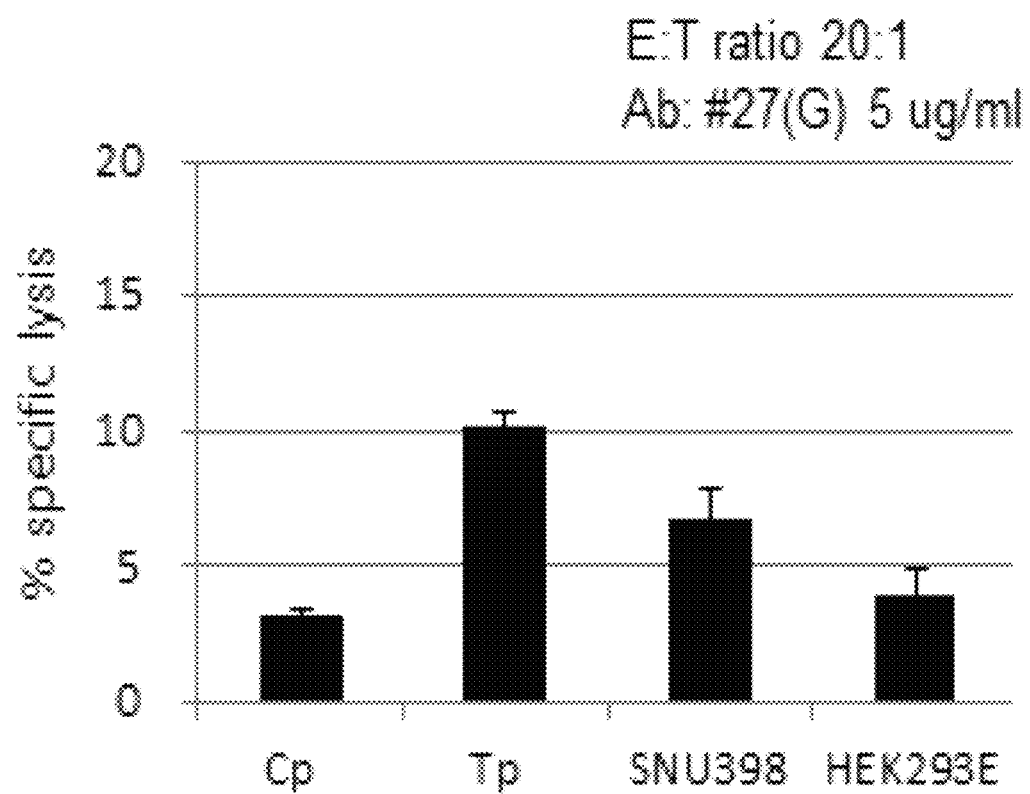

For the ADCC assay, the effector cell:target cell ratio, incubation time, etc., were determined via pilot experiments (the effector cell:target cell ratio=20:1, incubation time=12 h). TM4SF5-overexpressing liver cancer cell line (Tp) was treated with the antibody #27(G) (5 µg/mL), and it was confirmed that the antibody treatment resulted in about a 15%-20% ADCC induction (specific cell lysis %) (FIG. 19B). Additionally, in SNU-398 liver cancer cells, there was about a 7% ADCC induction by the treatment with the antibody #27 (FIG. 19C). In contrast, TM4SF5-negative (low) Cp cells and HEK293E cells showed no distinct ADCC (FIG. 19C).

Although HEK293E cells have a high level of TM4SF5 expression, there occurred no ADCC. Considering that HEK293E cells are not cancer cells but normal human embryonic kidney cells, it was suggested that the ADCC induction by the TM4SF5 target-specific antibodies was cancer-cell specific.

Figure 19D:
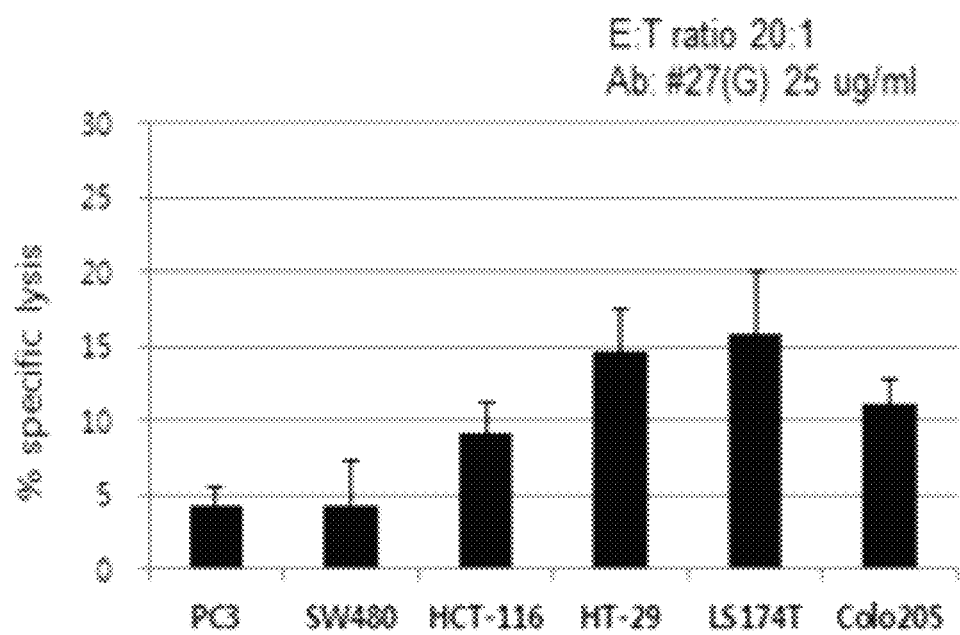

Additionally, the antibody #27(G) showed an 8%-16% ADCC induction in colorectal cancer cell lines of HCT116, HT29, LS174T, and Colo205, which exhibited the function-blocking effects, whereas the antibody #27(G) did not induce any distinct ADCC in SW480 and PC3 cells, which failed to exhibit the function-blocking effects (FIG. 19D).

Example 8: Analysis of TM4SF5-Specific Antibodies Inhibition of Liver Fibrosis

Experiments were performed by administering carbon tetrachloride ($CCl_4$), a liver fibrosis-inducing material, intraperitoneally to 5-week old BALB/C female mice. Olive oil for the control group and a mixture of 60% olive oil and 40% $CCl_4$ (0.4 mL/kg) for the experimental group were administered, respectively, and the experimental group was again subdivided into 3 groups of $CCl_4$-control group, $CCl_4$-#27 antibody group, and $CCl_4$-#79 antibody group.

Specifically, the Control group and $CCl_4$-Control of the experimental group were intraperitoneally administered with PBS on the first day and the fourth day, and the remaining experimental groups of $CCl_4$-#27 antibody, and $CCl_4$-#79 antibody groups were intraperitoneally administered with 5 µg of #27(G) antibody or 16 µg of #79(G) antibody, respectively, and in the morning on the sixth day, the Control group was administered with olive oil and all the experimental groups were administered with $CCl_4$. In the afternoon on the sixth day, PBS, 5 µg of #27(G) antibody or 16 µg of #79(G) antibody were administered in the same manner as on the first day, and on the eighth day and the eleventh day, again PBS, 5 µg of #27(G) antibody or 16 µg of #79(G) antibody were administered, thereby administering a total of 25 µg of #27(G) antibody per each mouse, or a total of 80 µg of #79(G) antibody per each mouse. 48 hours after the day of final administration, the eleventh day, they were dissected for observation.

Figure 20A:
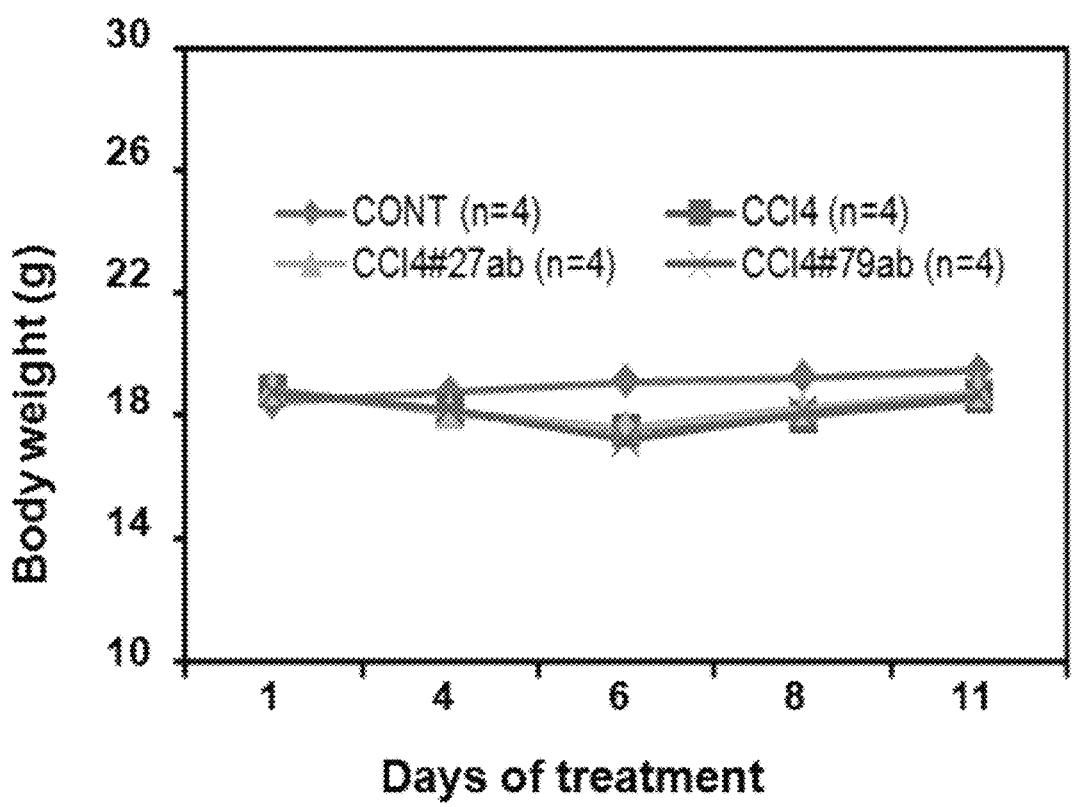
FIGS. 20A to 20B show a result that the TM4SF5-specific antibody can inhibit liver fibrosis.

FIG. 20A shows the result of body weight of the mice in Control group and the Experimental groups measured during the administration period. As shown in FIG. 20A, there were no significant decrease in body weights even when treated with #27(G) antibody or #79(G) antibody.

Figure 20B:
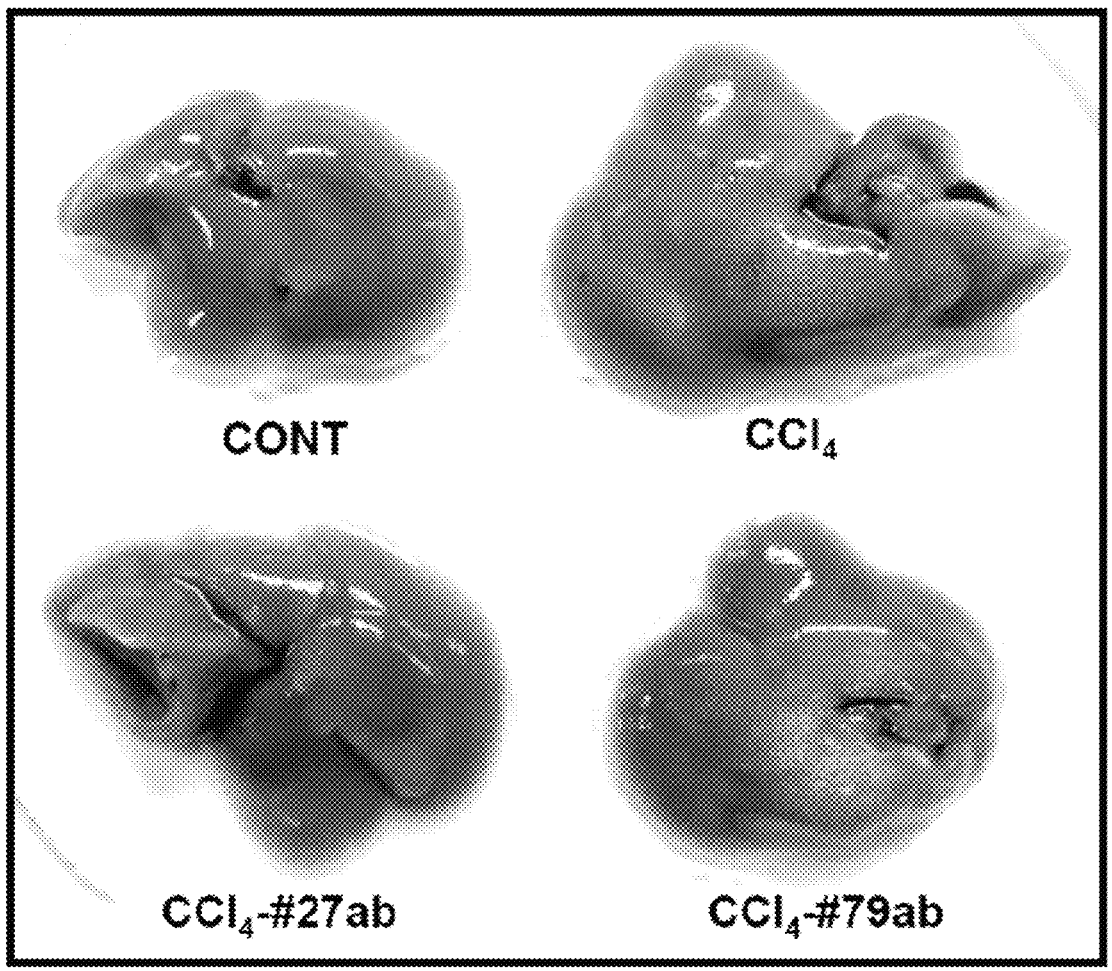

FIG. 20B shows the result of dissection of the mice in Control group and the Experimental groups. Specifically, a total of 16 mice consisting of 4 mice from the Control group administered with olive oil, and as Experimental groups, 4 mice from the $CCl_4$-Control, 4 mice from $CCl_4$-#27(G) antibody, or 4 mice from $CCl_4$-#79(G) antibody were dissected.

As a result, it was confirmed that the liver from the Control group administered with olive oil showed a red color similar to that of normal liver and its surface was smooth, whereas the liver from the $CCl_4$-Control showed a bit pale red, bigger in size, and had an overall uneven skin surface with white bumpy dots thus suggesting the occurrence of immune responses. The liver from the group administered with #27(G) antibody after administration with $CCl_4$ showed similarities in terms of color and surface to those of normal liver, suggesting that inhibitory effect of the antibody treatment against liver inflammation. The liver treated with #79(G) antibody showed a central region with a partially uneven surface having white bumpy dots but a smooth periphery, thus suggesting a partial inhibitory effect of the antibody against liver damage. That is, the #27(G) antibody showed a distinct inhibitory effect against inflammation (liver damage), whereas the 79(G) antibody showed a partial inhibitory effect.

From the foregoing, it was confirmed that the TM4SF5 antibodies of the present invention can be used for treatment and diagnosis of liver damage and liver fibrosis, which are precursor steps to liver cancer.

Example 9: In Vivo Tumor Growth Inhibition by TM4SF5-Specific Antibodies (1) Methods Nude mice (BALB/c-nude, 5 weeks old, male) were obtained from Japan SLC, Inc (Japan). SNU449Cp (control cells) (n=4) and SNU449T7 (TM4SF5-overexpressing stable cells) (n=15) were injected subcutaneously into the back of each mouse. In brief, $5 \times 10^6$ cells were resuspended in PBS and then mixed with Matrigel (BD Biosciences, Bedford, Mass. 01730, USA) on ice before injection. On 8th day, tumor-bearing mice injected with SNU449T7 cells were randomized into control and treatment groups (n=5 per group). #27(G) (5 ug/mouse) or #79(G) (16 ug/mouse) antibodies were intratumorally injected into each mouse at 2 or 3-day intervals (total 5 times). As a negative control, PBS (20 ul/mouse) was injected.

Figure 21A:
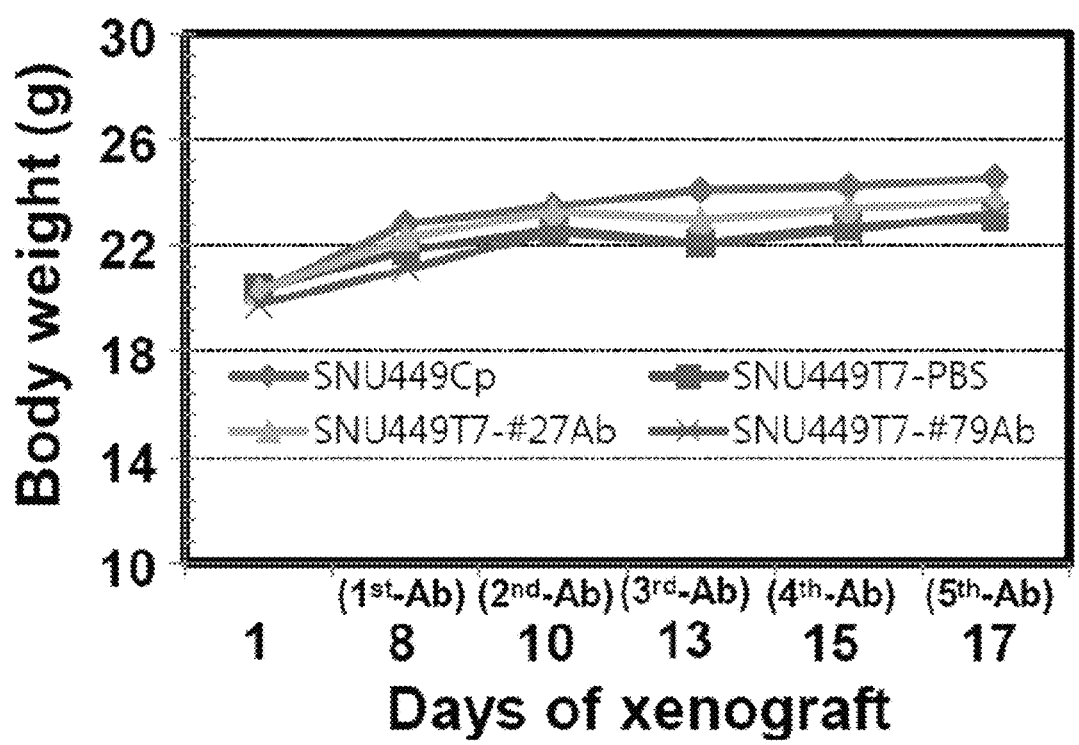
FIGS. 21A to 21C show a result that the TM4SF5-specific antibody can inhibit in vivo tumor growth.

Body weight and tumor volume were measured before antibody injection, and the result is shown in FIG. 21A.

The tumor volumes were calculated as follows: tumor volume=(a×b²)×½, where a was the width at the widest point of the tumor and b was the maximal width perpendicular to a. On 19th day, mice were sacrificed and photographed. The results are shown in FIG. 21B to C.

(2) Results

Figure 21B:
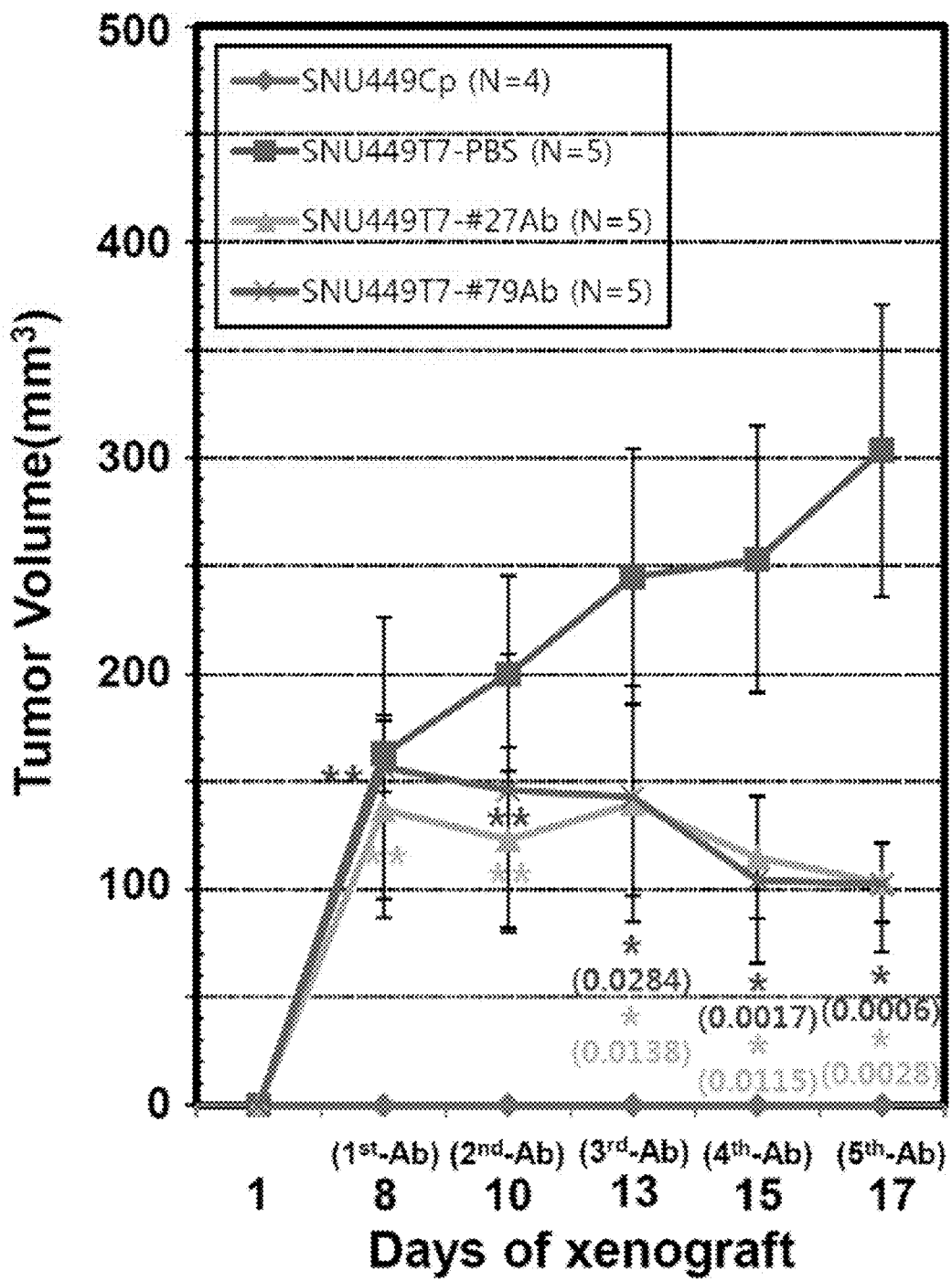
Figure 21C:
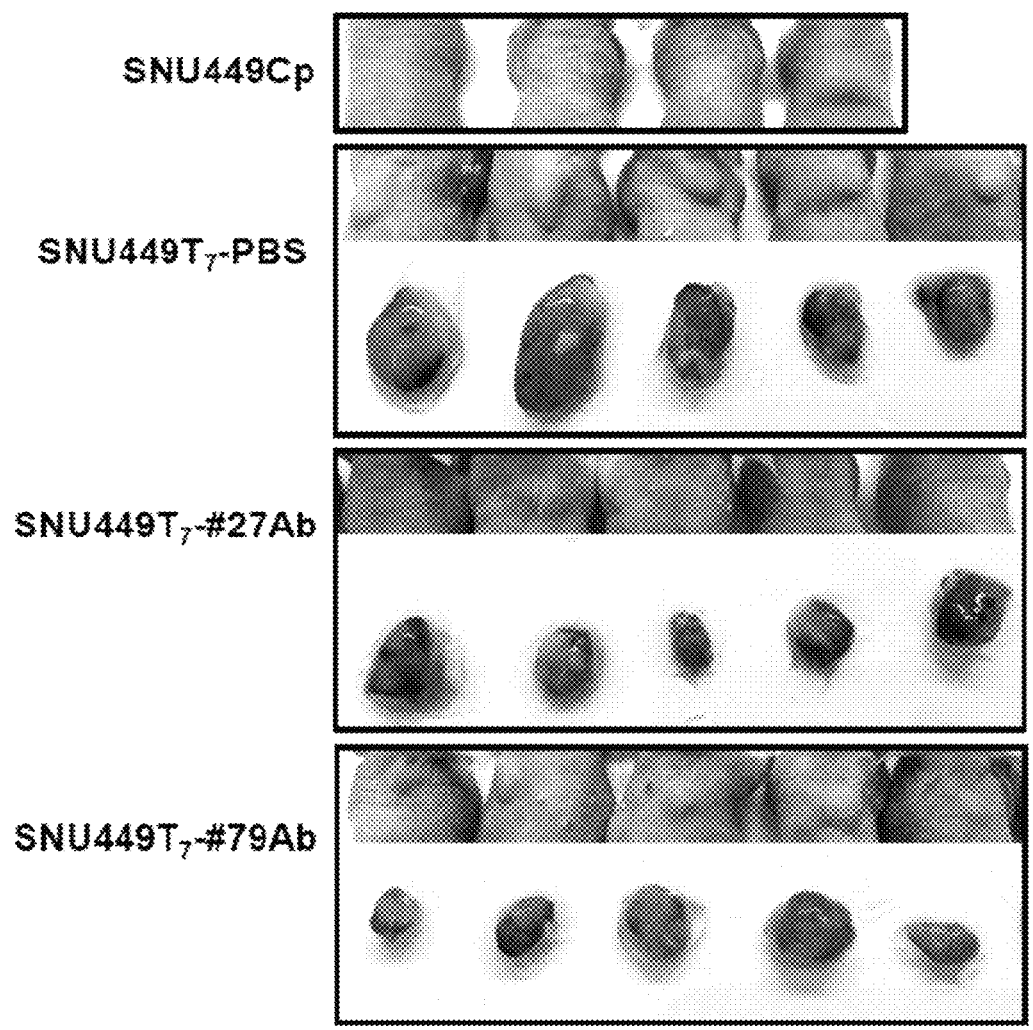

To evaluate the therapeutic efficacy in vivo, #27(G) and #79(G) antibodies were intratumorally injected into nude mice bearing TM4SF5-overexpressing SNU449T7 xenograft. #27(G) and #79(G) antibodies inhibited tumor growth in nude mice by 66% without affecting body weight, suggesting the potential anti-tumor activity of #27(G) and 79(G) antibodies (FIGS. 21A to 21C).

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A monoclonal antibody which specifically binds to human transmembrane 4 L six family member 5 (TM4SF5) protein, wherein the monoclonal antibody comprises:

(1) a heavy chain variable region comprising a heavy chain CDR1 comprising SEQ ID NO: 2; a heavy chain CDR2 comprising SEQ ID NO: 3; and a heavy chain CDR3 comprising SEQ ID NO: 4; and a light chain variable region comprising a light chain CDR1 comprising SEQ ID NO: 6; a light chain CDR2 comprising SEQ ID NO: 7; and a light chain CDR3 comprising SEQ ID NO: 8;

(2) a heavy chain variable region comprising a heavy chain CDR1 comprising SEQ ID NO: 2; a heavy chain CDR2 comprising SEQ ID NO: 3; and a heavy chain CDR3 comprising SEQ ID NO: 12; and a light chain variable region comprising a light chain CDR1 comprising SEQ ID NO: 14; a light chain CDR2 comprising SEQ ID NO: 15; and a light chain CDR3 comprising SEQ ID NO: 16;

(3) a heavy chain variable region comprising a heavy chain CDR1 comprising SEQ ID NO: 2; a heavy chain CDR2 comprising SEQ ID NO: 3; and a heavy chain CDR3 comprising SEQ ID NO: 20; and a light chain variable region comprising a light chain CDR1 comprising SEQ ID NO: 14; a light chain CDR2 comprising SEQ ID NO: 15; and a light chain CDR3 comprising SEQ ID NO: 22;
(4) a heavy chain variable region comprising a heavy chain CDR1 comprising SEQ ID NO: 2; a heavy chain CDR2 comprising SEQ ID NO: 3; and a heavy chain CDR3 comprising SEQ ID NO: 26; and a light chain variable region comprising a light chain CDR1 comprising SEQ ID NO: 14; a light chain CDR2 comprising SEQ ID NO: 15; and a light chain CDR3 comprising SEQ ID NO: 28; or
(5) a heavy chain variable region comprising a heavy chain CDR1 comprising SEQ ID NO: 32; a heavy chain CDR2 comprising SEQ ID NO: 33; and a heavy chain CDR3 comprising SEQ ID NO: 34; and a light chain variable region comprising a light chain CDR1 comprising SEQ ID NO: 36; a light chain CDR2 comprising SEQ ID NO: 15; and a light chain CDR3 comprising SEQ ID NO: 37.

2. The monoclonal antibody of claim 1, wherein the monoclonal antibody of (1) comprises:
a heavy chain variable region comprising SEQ ID NO: 1; and a light chain variable region comprising SEQ ID NO: 5.

3. The monoclonal antibody of claim 1, wherein the monoclonal antibody of (2) comprises:
a heavy chain variable region comprising SEQ ID NO: 11; and a light chain variable region comprising SEQ ID NO: 13.

4. The monoclonal antibody of claim 1, wherein the monoclonal antibody of (3) comprises:
a heavy chain variable region comprising SEQ ID NO: 19; and a light chain variable region comprising SEQ ID NO: 21.

5. The monoclonal antibody of claim 1, wherein the monoclonal antibody of (4) comprises:
a heavy chain variable region comprising SEQ ID NO: 25; and a light chain variable region comprising SEQ ID NO: 27.

6. The monoclonal antibody of claim 1, wherein the monoclonal antibody of (5) comprises:
a heavy chain variable region comprising SEQ ID NO: 31; and a light chain variable region comprising SEQ ID NO: 35.

7. A composition comprising the monoclonal antibody of claim 1.

8. A method for treating TM4SF5 expressing liver cancer, comprising administering the monoclonal antibody of claim 1 to a subject in need thereof.

9. A method for treating liver fibrosis, comprising administering the monoclonal antibody of claim 1 to a subject in need thereof.

10. A method for diagnosing transmembrane 4 L six family member 5 (TM4SF5) expressing cancer comprising
(i) contacting the monoclonal antibody of claim 1 with a biological sample isolated from a subject suspected of having cancer; and
(ii) detecting the formation of an antigen-antibody complex.

11. A method for diagnosing liver fibrosis comprising
(i) contacting the monoclonal antibody of claim 1 with a biological sample isolated from a subject suspected of having liver fibrosis; and
(ii) detecting the formation of an antigen-antibody complex.

12. A kit for diagnosing TM4SF5 expressing cancer comprising the monoclonal antibody of claim 1.

13. A kit for diagnosing liver fibrosis comprising the monoclonal antibody of claim 1.

14. A method for detecting an antigen-antibody complex, comprising
(i) contacting the monoclonal antibody of claim 1 with a biological sample isolated from a subject to produce an antigen-antibody complex; and
(ii) detecting the antigen-antibody complex.

15. A method for treating TM4SF5 expressing colon cancer, comprising administering the monoclonal antibody of claim 1 to a subject in need thereof.

16. A method for treating TM4SF5 expressing colorectal cancer, comprising administering the monoclonal antibody of claim 1 to a subject in need thereof.

* * * * *

SEQUENCE LISTING

```
<160> NUMBER OF SEQ ID NOS: 39

<210> SEQ ID NO 1
<211> LENGTH: 123
<212> TYPE: PRT
<213> ORGANISM: Artificial Sequence
<220> FEATURE:
<223> OTHER INFORMATION: a heavy chain variable region of TM4SF5
      antibody #1

<400> SEQUENCE: 1

Glu Val Gln Leu Gln Gln Phe Gly Ala Glu Leu Val Arg Pro Gly Ala
  1               5                  10                  15

Ser Val Thr Leu Ser Cys Lys Ala Ser Gly Tyr Thr Phe Thr Asp Tyr
             20                  25                  30

Glu Met His Trp Val Lys Gln Thr Pro Val His Gly Leu Glu Trp Ile
         35                  40                  45

Gly Ala Ile Asp Pro Glu Thr Gly Gly Thr Ala Tyr Asn Gln Lys Phe
     50                  55                  60

Lys Gly Lys Ala Ile Leu Thr Ala Asp Lys Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Arg Leu Thr Leu Phe Tyr Gly Asn Tyr Asp Trp Pro Phe Asp Val
            100                 105                 110

Trp Gly Thr Gly Thr Ser Val Thr Val Ser Ser
        115                 120

<210> SEQ ID NO 2
<211> LENGTH: 5
<212> TYPE: PRT
<213> ORGANISM: Artificial Sequence
<220> FEATURE:
<223> OTHER INFORMATION: CDR1 of a heavy chain variable region of TM4SF5
      antibody #1, 27, 79 and 88

<400> SEQUENCE: 2

Asp Tyr Glu Met His
  1               5

<210> SEQ ID NO 3
<211> LENGTH: 17
<212> TYPE: PRT
<213> ORGANISM: Artificial Sequence
<220> FEATURE:
<223> OTHER INFORMATION: CDR2 of a heavy chain variable region of TM4SF5
      antibody #1, 27, 79 and 88

<400> SEQUENCE: 3
```

```
Ala Ile Asp Pro Glu Thr Gly Gly Thr Ala Tyr Asn Gln Lys Phe Lys
 1               5                  10                  15

Gly

<210> SEQ ID NO 4
<211> LENGTH: 14
<212> TYPE: PRT
<213> ORGANISM: Artificial Sequence
<220> FEATURE:
<223> OTHER INFORMATION: CDR3 of a heavy chain variable region of TM4SF5
      antibody #1

<400> SEQUENCE: 4

Leu Thr Leu Phe Tyr Gly Asn Tyr Asp Trp Pro Phe Asp Val
 1               5                  10

<210> SEQ ID NO 5
<211> LENGTH: 107
<212> TYPE: PRT
<213> ORGANISM: Artificial Sequence
<220> FEATURE:
<223> OTHER INFORMATION: a light chain variable region of TM4SF5
      antibody #1

<400> SEQUENCE: 5

Asp Ile Val Met Thr Gln Ser Gln Lys Phe Met Ser Thr Ser Val Gly
 1               5                  10                  15

Asp Arg Val Ser Ile Thr Cys Lys Ala Ser Gln Asn Val Arg Thr Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Phe
                 85                  90                  95

Thr Phe Gly Ser Gly Thr Lys Leu Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: CDR1 of a light chain variable region of TM4SF5
      antibody #1

<400> SEQUENCE: 6

Lys Ala Ser Gln Asn Val Arg Thr Ala Val Ala
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: CDR2 of a light chain variable region of TM4SF5
      antibody #1

<400> SEQUENCE: 7

Trp Ala Ser Thr Arg His Thr
 1               5
```

<210> SEQ ID NO 8
<211> LENGTH: 9
<212> TYPE: PRT
<213> ORGANISM: Artificial Sequence
<220> FEATURE:
<223> OTHER INFORMATION: CDR3 of a light chain variable region of TM4SF5 antibody #1

<400> SEQUENCE: 8

Gln Gln Tyr Ser Ser Tyr Pro Phe Thr
 1               5

<210> SEQ ID NO 9
<211> LENGTH: 369
<212> TYPE: DNA
<213> ORGANISM: Artificial Sequence
<220> FEATURE:
<223> OTHER INFORMATION: a heavy chain variable region of TM4SF5 antibody #1

<400> SEQUENCE: 9
gaggtccagc tgcagcagtt tggggctgag ctggtgaggc ctggggcttc agtgacgctg      60
tcctgcaagg cttcgggcta cacatttact gactatgaaa tgcactgggt gaagcagaca     120
cctgtgcatg gcctggaatg gattggagct attgatcctg aaactggtgg tactgcctac     180
aatcagaagt tcaagggcaa ggccatactg actgcagaca atcctccag cacagcctac      240 atggagctcc gcagcctgac atctgaggac tctgcggtct atttctgtgc aagattgact     300
ctcttttacg gtaactacga ctggcccttc gatgtctggg gcacagggac ctcagtcacc     360
gtctcctca                                                             369

<210> SEQ ID NO 10
<211> LENGTH: 321
<212> TYPE: DNA
<213> ORGANISM: Artificial Sequence
<220> FEATURE:
<223> OTHER INFORMATION: a light chain variable region of TM4SF5 antibody #1

<400> SEQUENCE: 10
gacattgtga tgactcagtc tcaaaaattc atgtccacat cagttggaga cagggtcagc      60
atcacctgca aggccagtca gaatgttcgt actgctgtag cctggtatca acagaaacca     120
gggcagtctc ctaaactact gatttactgg gcatccaccc ggcacactgg agtccctgat     180
cgcttcacag gcagtggatc tgggacagat ttcactctca ccattagcaa tgtgcagtct     240
gaagacttgg cagattattt ctgtcagcaa tatagcagct atccattcac gttcggctcg     300
gggaccaaac tggaaataaa a                                               321

<210> SEQ ID NO 11
<211> LENGTH: 114
<212> TYPE: PRT
<213> ORGANISM: Artificial Sequence
<220> FEATURE:
<223> OTHER INFORMATION: a heavy chain variable region of TM4SF5 antibody #27

<400> SEQUENCE: 11

Gln Val Gln Leu Gln Gln Phe Gly Ala Glu Leu Val Arg Pro Gly Ala
 1               5                  10                  15

Ser Val Thr Leu Ser Cys Lys Ala Ser Gly Tyr Thr Phe Thr Asp Tyr
            20                  25                  30

```
Glu Met His Trp Val Lys Gln Thr Pro Val His Gly Leu Glu Trp Ile
            35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Pro Tyr Leu Gly Tyr Trp Gly Gln Gly Thr Thr Val Thr Val
            100                 105                 110

Ser Ser

<210> SEQ ID NO 12
<211> LENGTH: 5
<212> TYPE: PRT
<213> ORGANISM: Artificial Sequence
<220> FEATURE:
<223> OTHER INFORMATION: CDR3 of a heavy chain variable region of TM4SF5
      antibody #27

<400> SEQUENCE: 12

Pro Tyr Leu Gly Tyr
 1               5

<210> SEQ ID NO 13
<211> LENGTH: 112
<212> TYPE: PRT
<213> ORGANISM: Artificial Sequence
<220> FEATURE:
<223> OTHER INFORMATION: a light chain variable region of TM4SF5
      antibody #27

<400> SEQUENCE: 13

Asp Ala Val Val Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Leu Thr Phe Gly Ala Gly Thr Lys Leu Glu Leu Lys
            100                 105                 110

<210> SEQ ID NO 14
<211> LENGTH: 16
<212> TYPE: PRT
<213> ORGANISM: Artificial Sequence
<220> FEATURE:
<223> OTHER INFORMATION: CDR1 of a light chain variable region of TM4SF5
      antibody #27, 79 and 88

<400> SEQUENCE: 14

Arg Ser Ser Gln Ser Leu Val His Ser Asn Gly Asn Thr Tyr Leu His
 1               5                  10                  15

<210> SEQ ID NO 15
```

```
<211> LENGTH: 7
<212> TYPE: PRT
<213> ORGANISM: Artificial Sequence
<220> FEATURE:
<223> OTHER INFORMATION: CDR2 of a light chain variable region of TM4SF5
      antibody #27, 79, 88 and 92

<400> SEQUENCE: 15

Lys Val Ser Asn Arg Phe Ser
 1               5

<210> SEQ ID NO 16
<211> LENGTH: 9
<212> TYPE: PRT
<213> ORGANISM: Artificial Sequence
<220> FEATURE:
<223> OTHER INFORMATION: CDR3 of a light chain variable region of TM4SF5
      antibody #27

<400> SEQUENCE: 16

Phe Gln Gly Ser His Ile Pro Leu Thr
 1               5

<210> SEQ ID NO 17
<211> LENGTH: 342
<212> TYPE: DNA
<213> ORGANISM: Artificial Sequence
<220> FEATURE:
<223> OTHER INFORMATION: a heavy chain variable region of TM4SF5
      antibody #27

<400> SEQUENCE: 17
caggtccagc tgcagcagtt tggggctgag ctggtgaggc ctggggcttc agtgacgctg     60
tcctgcaagg cttcgggcta cacatttact gactatgaaa tgcactgggt gaagcagaca    120
cctgtgcatg gcctggaatg gattggagct attgatcctg aaactggtgg tactgcctac    180
aatcagaagt tcaagggcaa ggccatactg actgcagaca atcctccag cacagcctac     240 atggagctcc gcagcctgac atctgaggac tctgccgtct attactgtac aagaccctac    300
ttggggtact ggggtcaagg aaccacggtc accgtctcct ca                       342

<210> SEQ ID NO 18
<211> LENGTH: 336
<212> TYPE: DNA
<213> ORGANISM: Artificial Sequence
<220> FEATURE:
<223> OTHER INFORMATION: a light chain variable region of TM4SF5
      antibody #27

<400> SEQUENCE: 18
gatgctgtgg tgacccaaac tccactctcc ctgcctgtca gtcttggaga tcaagcctcc     60
atctcttgca gatctagtca gagccttgta cacagtaatg gaaacaccta tttacattgg    120
taccttcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatattccg    300
ctcacgttcg gtgctgggac caagctggag ctgaaa                              336

<210> SEQ ID NO 19
<211> LENGTH: 114
<212> TYPE: PRT
<213> ORGANISM: Artificial Sequence
<220> FEATURE:
<223> OTHER INFORMATION: a heavy chain variable region of TM4SF5
``` antibody #79

<400> SEQUENCE: 19

```
Gly Val Gln Leu Gln Gln Ser Gly Ala Glu Leu Val Arg Pro Gly Ala
 1               5                   10                  15

Ser Val Lys Leu Ser Cys Lys Ala Ser Gly Tyr Thr Phe Thr Asp Tyr
             20                  25                  30

Glu Met His Trp Val Lys Gln Thr Pro Val His Gly Leu Glu Trp Ile
         35                  40                  45

Gly Ala Ile Asp Pro Glu Thr Gly Gly Thr Ala Tyr Asn Gln Lys Phe
     50                  55                  60

Lys Gly Lys Ala Ile Leu Thr Ala Asp Lys Ser Ser Ser Thr Ala Tyr
 65                  70                  75                  80

Met Glu Leu Arg Ser Leu Thr Ser Glu Asp Ser Ala Val Tyr Tyr Cys
             85                  90                  95

Thr Val Tyr Gly Leu Ala Tyr Trp Gly Gln Gly Thr Leu Val Thr Val
            100                 105                 110

Ser Ala
```

<210> SEQ ID NO 20
<211> LENGTH: 5
<212> TYPE: PRT
<213> ORGANISM: Artificial Sequence
<220> FEATURE:
<223> OTHER INFORMATION: CDR3 of a heavy chain variable region of TM4SF5 antibody #79

<400> SEQUENCE: 20

```
Tyr Gly Leu Ala Tyr
 1               5
```

<210> SEQ ID NO 21
<211> LENGTH: 112
<212> TYPE: PRT
<213> ORGANISM: Artificial Sequence
<220> FEATURE:
<223> OTHER INFORMATION: a light chain variable region of TM4SF5 antibody #79

<400> SEQUENCE: 21

```
Asp Val Val Met Thr Gln Thr Pro Leu Ser Leu Pro Val Ser Leu Gly
 1               5                   10                  15

Asp Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Asn
             85                  90                  95

Thr His Val Pro Tyr Thr Phe Gly Gly Gly Thr Lys Leu Glu Leu Lys
            100                 105                 110
```

<210> SEQ ID NO 22
<211> LENGTH: 9
<212> TYPE: PRT
<213> ORGANISM: Artificial Sequence
<220> FEATURE:

<223> OTHER INFORMATION: CDR3 of a light chain variable region of TM4SF5
      antibody #79

<400> SEQUENCE: 22

Ser Gln Asn Thr His Val Pro Tyr Thr
  1               5

<210> SEQ ID NO 23
<211> LENGTH: 342
<212> TYPE: DNA
<213> ORGANISM: Artificial Sequence
<220> FEATURE:
<223> OTHER INFORMATION: a heavy chain variable region of TM4SF5
      antibody #79

<400> SEQUENCE: 23
ggggttcagc tgcagcagtc tggggctgag ctggtgaggc ctggggcttc agtgaagctg      60
tcctgcaagg cttcgggtta cacatttact gactatgaaa tgcactgggt gaagcagaca     120
cctgtgcatg gcctggaatg gattggagct attgatcctg aaactggtgg tactgcctac     180
aatcagaagt tcaagggcaa ggccatactg actgcagaca atcctccag cacagcctac      240 atggagctcc gcagcctgac atctgaggac tctgccgtct attactgtac cgtttacggc     300
ttggcttact ggggccaagg gactctggtc actgtctctg ca                         342

<210> SEQ ID NO 24
<211> LENGTH: 336
<212> TYPE: DNA
<213> ORGANISM: Artificial Sequence
<220> FEATURE:
<223> OTHER INFORMATION: a light chain variable region of TM4SF5
      antibody #79

<400> SEQUENCE: 24
gatgttgtta tgacccaaac tccactctcc ctgcctgtca gtcttggaga tcaagcctcc      60
atctcttgca gatctagtca gagccttgta cacagtaatg aaacacccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaaatac acatgttcca     300
tacacgttcg gaggggggac caagctggag ctgaaa                                336

<210> SEQ ID NO 25
<211> LENGTH: 116
<212> TYPE: PRT
<213> ORGANISM: Artificial Sequence
<220> FEATURE:
<223> OTHER INFORMATION: a heavy chain variable region of TM4SF5
      antibody #88

<400> SEQUENCE: 25

Gln Val Gln Leu Gln Gln Phe Gly Ala Glu Leu Val Arg Pro Gly Ala
  1               5                  10                  15

Ser Val Lys Leu Ser Cys Lys Ala Ser Gly Tyr Thr Phe Thr Asp Tyr
                 20                  25                  30

Glu Met His Trp Val Lys Gln Thr Pro Val His Gly Leu Glu Trp Ile
             35                  40                  45

Gly Ala Ile Asp Pro Glu Thr Gly Gly Thr Ala Tyr Asn Gln Lys Phe
         50                  55                  60

Lys Gly Lys Ala Thr Leu Thr Ala Asp Lys Ser Ser Ser Thr Ala Tyr
 65                  70                  75                  80

```
Met Glu Leu Arg Ser Leu Thr Ser Glu Asp Ser Ala Val Tyr Tyr Cys
                85                  90                  95

Thr Pro Asn Tyr Trp Tyr Phe Asp Val Trp Gly Ala Gly Thr Ser Val
            100                 105                 110

Thr Val Ser Ser
        115

<210> SEQ ID NO 26
<211> LENGTH: 7
<212> TYPE: PRT
<213> ORGANISM: Artificial Sequence
<220> FEATURE:
<223> OTHER INFORMATION: CDR3 of a heavy chain variable region of TM4SF5
      antibody #88

<400> SEQUENCE: 26

Asn Tyr Trp Tyr Phe Asp Val
 1               5

<210> SEQ ID NO 27
<211> LENGTH: 112
<212> TYPE: PRT
<213> ORGANISM: Artificial Sequence
<220> FEATURE:
<223> OTHER INFORMATION: a light chain variable region of TM4SF5
      antibody #88

<400> SEQUENCE: 27

Asp Ala Val Val Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Leu Lys
            100                 105                 110

<210> SEQ ID NO 28
<211> LENGTH: 9
<212> TYPE: PRT
<213> ORGANISM: Artificial Sequence
<220> FEATURE:
<223> OTHER INFORMATION: CDR3 of a light chain variable region of TM4SF5
      antibodies #88

<400> SEQUENCE: 28

Ser Gln Ser Thr His Val Pro Tyr Thr
 1               5

<210> SEQ ID NO 29
<211> LENGTH: 348
<212> TYPE: DNA
<213> ORGANISM: Artificial Sequence
<220> FEATURE:
<223> OTHER INFORMATION: a heavy chain variable region of TM4SF5
      antibodies #88
```

-continued

<400> SEQUENCE: 29

```
caggtccagc tgcagcagtt tggggctgag ctggtgaggc ctggggcttc agtgaagctg      60
tcctgcaagg cttcgggcta cacatttact gactatgaaa tgcactgggt gaagcagaca     120
cctgtgcatg gcctggaatg gattggagct attgatcctg aaactggtgg tactgcctac     180
aatcagaagt tcaagggcaa ggccacactg actgcagaca atcctccag cacagcctac      240
atggagctcc gcagcctgac atctgaggac tctgccgtct attactgtac ccctaactac     300
tggtacttcg atgtctgggg cgcagggacc tcagtcaccg tctcctca                  348
```

<210> SEQ ID NO 30
<211> LENGTH: 336
<212> TYPE: DNA
<213> ORGANISM: Artificial Sequence
<220> FEATURE:
<223> OTHER INFORMATION: a light chain variable region of TM4SF5
      antibodies #88

<400> SEQUENCE: 30

```
gatgctgttg tgacccaaac tccactctcc ctgcctgtca gtcttggaga tcaagcctcc      60
atctcttgca gatctagtca gagccttgta cacagtaatg aaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tacacgttcg gaggggggac caagctggag ctgaaa                               336
```

<210> SEQ ID NO 31
<211> LENGTH: 113
<212> TYPE: PRT
<213> ORGANISM: Artificial Sequence
<220> FEATURE:
<223> OTHER INFORMATION: a heavy chain variable region of TM4SF5
      antibodies #92

<400> SEQUENCE: 31

```
Glu Val Gln Leu Gln Gln Ser Val Ala Asp Leu Val Arg Pro Gly Ala
  1               5                  10                  15

Ser Val Lys Leu Ser Cys Thr Ala Ser Gly Phe Asn Ile Glu Asn Thr
             20                  25                  30

Tyr Met His Trp Val Lys Gln Arg Pro Glu Gln Gly Leu Glu Trp Ile
         35                  40                  45

Gly Arg Ile Asp Pro Ala Asn Gly Asn Thr Lys Tyr Ala Pro Lys Phe
     50                  55                  60

Gln Asp Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Thr Ser Leu Gly Ala Tyr Trp Gly Gln Gly Thr Leu Val Thr Val Ser
            100                 105                 110

Ala
```

<210> SEQ ID NO 32
<211> LENGTH: 5
<212> TYPE: PRT
<213> ORGANISM: Artificial Sequence
<220> FEATURE:
<223> OTHER INFORMATION: CDR1 of a heavy chain variable region of TM4SF5
      antibodies #92

<400> SEQUENCE: 32

Asn Thr Tyr Met His
  1               5

<210> SEQ ID NO 33
<211> LENGTH: 17
<212> TYPE: PRT
<213> ORGANISM: Artificial Sequence
<220> FEATURE:
<223> OTHER INFORMATION: CDR2 of a heavy chain variable region of TM4SF5
      antibodies #92

<400> SEQUENCE: 33

Arg Ile Asp Pro Ala Asn Gly Asn Thr Lys Tyr Ala Pro Lys Phe Gln
  1               5                  10                  15

Asp

<210> SEQ ID NO 34
<211> LENGTH: 4
<212> TYPE: PRT
<213> ORGANISM: Artificial Sequence
<220> FEATURE:
<223> OTHER INFORMATION: CDR3 of a heavy chain variable region of TM4SF5
      antibodies #92

<400> SEQUENCE: 34

Leu Gly Ala Tyr
  1

<210> SEQ ID NO 35
<211> LENGTH: 112
<212> TYPE: PRT
<213> ORGANISM: Artificial Sequence
<220> FEATURE:
<223> OTHER INFORMATION: a light chain variable region of TM4SF5
      antibodies #92

<400> SEQUENCE: 35

Asp Ala Val Leu Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Leu Thr Phe Gly Ala Gly Thr Lys Leu Glu Ile Lys
            100                 105                 110

<210> SEQ ID NO 36
<211> LENGTH: 16
<212> TYPE: PRT
<213> ORGANISM: Artificial Sequence
<220> FEATURE:
<223> OTHER INFORMATION: CDR1 of a light chain variable region of TM4SF5
      antibodies #92

<400> SEQUENCE: 36

```
Arg Ser Ser Gln Ser Ile Val His Ser Asn Gly Asn Thr Tyr Leu Glu
  1               5                  10                  15

<210> SEQ ID NO 37
<211> LENGTH: 9
<212> TYPE: PRT
<213> ORGANISM: Artificial Sequence
<220> FEATURE:
<223> OTHER INFORMATION: CDR3 of a light chain variable region of TM4SF5
      antibodies #92

<400> SEQUENCE: 37

Ser Gln Ser Thr His Val Pro Leu Thr
  1               5

<210> SEQ ID NO 38
<211> LENGTH: 339
<212> TYPE: DNA
<213> ORGANISM: Artificial Sequence
<220> FEATURE:
<223> OTHER INFORMATION: a heavy chain variable region of TM4SF5
      antibodies #92

<400> SEQUENCE: 38
gaggttcagc tgcagcagtc tgtggcagac cttgtgaggc caggggcctc agtcaagttg      60
tcctgcacag cttctggctt caacattgaa aacacctata tgcactgggt gaaacagagg     120
cctgaacagg gcctggagtg gattggaagg attgatcctg cgaatggtaa tactaaaatt     180
gccccgaagt tccaggacaa ggccactata actgcagaca tcctccaa cacagcctac      240 ctgcagctca gcagcctgac atctgaggac actgccgtct attactgtac tagcctaggc     300
gcttactggg gccaagggac tctggtcact gtctctgca                            339

<210> SEQ ID NO 39
<211> LENGTH: 336
<212> TYPE: DNA
<213> ORGANISM: Artificial Sequence
<220> FEATURE:
<223> OTHER INFORMATION: a light chain variable region of TM4SF5
      antibodies #92

<400> SEQUENCE: 39
gatgctgttc tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
ctcacgttcg gtgctgggac caagctggaa atcaaa                               336
```